(12) United States Patent
Thor et al.

(10) Patent No.: US 12,279,984 B2
(45) Date of Patent: Apr. 22, 2025

(54) ANKLE FOOT ORTHOSIS

(71) Applicant: THORWEAR INC., San Diego, CA (US)

(72) Inventors: Arni Thor, Coronado, CA (US); Zoe Bornhorst, San Diego, CA (US); Pei Hsuan Li, San Diego, CA (US); Marina Gurria Diaz, San Diego, CA (US); Efrain Navarrete, San Diego, CA (US); Kelly McGee, San Diego, CA (US)

(73) Assignee: THORWEAR INC., San Diego, CA (US)

( * ) Notice: Subject to any disclaimer, the term of this patent is extended or adjusted under 35 U.S.C. 154(b) by 262 days.

(21) Appl. No.: 17/853,871

(22) Filed: Jun. 29, 2022

(65) Prior Publication Data

US 2023/0000655 A1 Jan. 5, 2023

Related U.S. Application Data

(60) Provisional application No. 63/216,747, filed on Jun. 30, 2021.

(51) Int. Cl.
*A61F 5/01* (2006.01)
*A61L 15/08* (2006.01)
*A61L 15/14* (2006.01)

(52) U.S. Cl.
CPC ............. *A61F 5/0113* (2013.01); *A61L 15/08* (2013.01); *A61L 15/14* (2013.01)

(58) Field of Classification Search
CPC .. A61F 5/01–0104; A61F 5/0111–0116; A61F 5/0127; A61F 5/0193;
(Continued)

(56) References Cited

U.S. PATENT DOCUMENTS 2,949,111 A 8/1960 Ruotoistenmaki
4,646,726 A 3/1987 Westin et al.
(Continued)

FOREIGN PATENT DOCUMENTS

EP 0270661 6/1987
EP 2932944 10/2015
(Continued)

OTHER PUBLICATIONS

Written Opinion of the International Searching Authority for PCT/US2020/047228 dated Dec. 2, 2020.
(Continued)

*Primary Examiner* — Michelle J Lee
(74) *Attorney, Agent, or Firm* — Garson & Gutierrez, PC

(57) ABSTRACT

Ankle foot orthoses (AFO) and methods of customizing an AFO. In one embodiment, the AFO includes a carbon fiber strut that includes a carbon fiber foot plate; a formable layer that is coupled with the carbon fiber foot plate, the formable layer being formable from an initial shape to a formed shape; an inner boot, where the formable layer being formed into the formed shape is configured to be formed around geometry of portions of the inner boot; and a moldable calf piece that is configured to be attached to the carbon fiber strut. The AFO may also include a strapping system that is coupled between the moldable calf piece and the inner boot. Methods of manufacturing and customizing the aforementioned AFO are also disclosed.

12 Claims, 56 Drawing Sheets

(58) Field of Classification Search
CPC .. A61F 5/0195; A61F 5/04; A61F 5/05; A61F 5/058; A61F 5/05841; A61F 5/0585; A61F 5/14; A61F 13/06; A61F 13/064–067; A43B 7/00; A43B 7/14–1445; A43B 7/18; A43B 7/20; A43B 13/00; A43B 13/02; A43B 13/12; A61L 15/07; A61L 15/08; A61L 15/14

See application file for complete search history.

(56) References Cited

U.S. PATENT DOCUMENTS

| | | | |
|---|---|---|---|
| 5,776,090 | A | 7/1998 | Bergmann et al. |
| 5,817,041 | A | 10/1998 | Bader |
| 5,897,515 | A | 4/1999 | Willner et al. |
| 6,110,135 | A | 8/2000 | Madow et al. |
| 6,146,344 | A | 11/2000 | Bader |
| 6,146,349 | A | 11/2000 | Rothschild et al. |
| 6,676,618 | B2 | 1/2004 | Andersen |
| 6,945,947 | B2 | 9/2005 | Ingimundarson et al. |
| 7,077,818 | B2 | 7/2006 | Ingimundarson et al. |
| 7,266,910 | B2 | 9/2007 | Ingimundarson |
| 7,270,644 | B2 | 9/2007 | Ingimundarson |
| 7,354,413 | B2 | 4/2008 | Fisher |
| 7,513,880 | B2 | 4/2009 | Ingimundarson et al. |
| 7,749,423 | B2 | 7/2010 | Bader |
| 7,753,864 | B2 | 7/2010 | Beckwith et al. |
| 7,766,851 | B2 | 8/2010 | Lindh et al. |
| 8,021,316 | B2 | 9/2011 | Franke et al. |
| 8,323,224 | B2 | 12/2012 | Shlomovitz |
| 8,403,872 | B2 | 3/2013 | Franke et al. |
| 8,540,655 | B2 | 9/2013 | Franke et al. |
| 9,121,673 | B2 | 9/2015 | Popovici |
| 9,192,504 | B2 | 11/2015 | Andrews et al. |
| 9,211,208 | B2 | 12/2015 | Blum et al. |
| 9,326,880 | B2 | 5/2016 | Szczepanski |
| 9,433,522 | B2 | 9/2016 | Bader |
| 9,526,651 | B2 | 12/2016 | Kozasa et al. |
| 9,562,742 | B2 | 2/2017 | Popovici |
| 9,788,987 | B2 * | 10/2017 | Vollbrecht ............ A61F 5/0111 |
| 9,855,161 | B1 | 1/2018 | Bonaroti |
| 9,889,035 | B2 | 2/2018 | Jordan et al. |
| 9,901,475 | B2 | 2/2018 | Jordan et al. |
| 9,980,847 | B2 | 5/2018 | Andrews et al. |
| 10,052,221 | B2 | 8/2018 | Albertsson et al. |
| 10,105,252 | B2 | 10/2018 | Bader |
| 10,561,514 | B2 | 2/2020 | Romo et al. |
| 12,156,825 | B2 * | 12/2024 | Gunnsteinsson ..... A61F 5/0111 |
| 2005/0234378 | A1 | 10/2005 | Ingimundarson et al. |
| 2007/0038169 | A1 | 2/2007 | Alon et al. |
| 2007/0073202 | A1 | 3/2007 | Bader |
| 2007/0100268 | A1 | 5/2007 | Fisher |
| 2008/0077066 | A1 | 3/2008 | Lewis |
| 2008/0300525 | A1 | 12/2008 | Shlomovitz |
| 2009/0287128 | A1 | 11/2009 | Ingimundarson et al. |
| 2013/0072841 | A1 | 3/2013 | Bader |
| 2013/0131569 | A1 | 5/2013 | Blum et al. |
| 2014/0276318 | A1 | 9/2014 | Faux |
| 2014/0276320 | A1 | 9/2014 | Faux et al. |
| 2014/0378881 | A1 | 12/2014 | Wagner |
| 2015/0065934 | A1 | 3/2015 | Bader |
| 2015/0119781 | A1 | 4/2015 | Ponce |
| 2015/0148725 | A1 | 5/2015 | Johnsson et al. |
| 2015/0150709 | A1 | 6/2015 | Ljubimir et al. |
| 2015/0265450 | A1 | 9/2015 | Rodgers |
| 2015/0320581 | A1 | 11/2015 | Causse |
| 2016/0074199 | A1 | 3/2016 | Bader |
| 2016/0213552 | A1 | 7/2016 | Lindsay |
| 2016/0220406 | A1 | 8/2016 | Bader |
| 2017/0165094 | A1 * | 6/2017 | Voskuilen ............ A61F 5/0111 |
| 2017/0165095 | A1 | 6/2017 | Romo et al. |
| 2017/0216071 | A1 | 8/2017 | Bader |
| 2017/0348132 | A1 | 12/2017 | Cooney |
| 2018/0333285 | A1 | 11/2018 | Thor et al. |
| 2020/0375776 | A1 * | 12/2020 | Thor ..................... A61F 5/14 |
| 2022/0183869 | A1 * | 6/2022 | Morris .................. A43B 13/28 |
| 2022/0378597 | A1 * | 12/2022 | Thor ..................... A61F 5/0111 |

FOREIGN PATENT DOCUMENTS

| | | |
|---|---|---|
| EP | 3301680 | 9/2017 |
| GB | 2375962 | 12/2002 |
| GB | 25355612 | 8/2016 |
| GB | 2556317 | 5/2018 |
| GB | 2571963 | 9/2019 |
| GB | 2571965 | 9/2019 |
| RU | 2277394 | 6/2006 |
| WO | 2001034071 | 5/2001 |
| WO | 2004066890 | 8/2004 |
| WO | 2008001394 | 1/2008 |
| WO | 2009139019 | 11/2009 |
| WO | 2011029837 | 3/2011 |
| WO | 2014001793 | 1/2014 |
| WO | 2017103621 | 6/2017 |
| WO | 2017134429 | 8/2017 |
| WO | 2017207532 | 12/2017 |
| WO | 2017212242 | 12/2017 |
| WO | 2019175589 | 9/2019 |
| WO | 2019175592 | 9/2019 |

OTHER PUBLICATIONS

Written Opinion of the International Searching Authority for PCT/US2022/035611 dated Oct. 24, 2022.

* cited by examiner

ANKLE FOOT ORTHOSIS

PRIORITY

This application claims the benefit of priority to U.S. Provisional Patent Application Ser. No. 63/216,747 of the same title, filed Jun. 30, 2021, the contents of which being incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE DISCLOSURE

Field of the Disclosure

The present disclosure relates generally to the field of the correction of disorders of the lower limbs by use of braces and other devices to correct alignment or provide support and in one exemplary aspect, to ankle foot orthoses and methods for manufacturing and using the same.

Description of Related Art

Drop foot is a gait abnormality which is typically caused by irritation or damage to the fibular nerve, and/or paralysis of the muscles in the anterior portion of the lower leg. Additionally, a significant portion of patients presenting with drop foot often have other comorbidities that may require a customized version of an ankle foot orthoses ("AFO") to appropriately treat the condition. The primary reasons for why a patient may need a custom AFO device are: (1) frontal plane instability; (2) plantar flexion contracture; (3) size/weight/activity restrictions; and/or (4) anatomical causes. However, receiving a custom made AFO device can be challenging for several reasons and options for dynamic treatment are limited. These main challenges include: (1) design complexity in building a custom device; (2) the large amount of time that it takes to build a custom AFO device; and (3) the cost and difficulty in getting approval for reimbursement by an insurance company. Additionally, clinicians are often limited in material options, oftentimes choosing a thermoplastic design over, for example, carbon fiber due to the complexity of fabrication which often leads to suboptimal treatment. Historically, custom made AFO devices have been produced in individual clinics, however in recent years, these fabrications have been largely transferred to custom fabrication centers which leads to issues of longer lead times to fit the patient, higher costs associated with shipping casts and braces back and forth, as well as a lack of communication between the patient and the fabricators of the AFO device resulting in, inter alia, increased fitting issues.

Accordingly, there remains a salient need for an orthotic device that addresses the foregoing problems by providing a dynamic carbon fiber device that can be easily custom made to a patient's model or measurements and physical limitations in a clinical setting that can be manufactured in short amount of time while the patient waits for the AFO to be customized. Ideally, such AFO devices can be made during a single clinical visit while providing the dynamic properties and low strength to weight ratio of carbon fiber that has been traditionally difficult to achieve. Finally, such AFO devices will be cost effective to manufacture, while addressing the challenges of multiplanar stability, fit, plantar flexion contracture and variable level of support in all planes of movement.

SUMMARY

The present disclosure satisfies the foregoing needs by providing, inter alia, an AFO device that address some or all of the foregoing deficiencies as well as methods of their manufacture and methods of their use.

In one aspect, an ankle foot orthosis (AFO) is disclosed. In one embodiment, the AFO includes a carbon fiber strut that includes a carbon fiber foot plate; a formable layer that is coupled with the carbon fiber foot plate, the formable layer being formable from an initial shape to a formed shape; an inner boot, where the formable layer being formed into the formed shape is configured to be formed around geometry of portions of the inner boot; and a moldable calf piece that is configured to be attached to the carbon fiber strut In one variant, the AFO also includes a strap made of webbing material that is coupled between the moldable calf piece and the inner boot.

In another variant, the strap includes a stopper at an end portion of the strap, the stopper being received on an external surface of the inner boot, the strap being fed through a slot disposed in the inner boot.

In yet another variant, the inner boot includes a recess positioned around the slot disposed in the inner boot, the recess configured to receive the stopper of the strap.

In yet another variant, the stopper is oriented orthogonal to the webbing material of the strap, the webbing material having two layers of webbing material, one layer of the two layers being oriented in a first direction of the stopper, the second layer of the two layers being oriented in a second direction of the stopper, the second direction being opposite from the first direction.

In yet another variant, the inner boot includes a posterior slot, the posterior slot being disposed at a posterior portion of the inner boot and a back strap that has a first end attached to an inner surface of the inner boot, the back strap being routed through the posterior slot, the back strap being routed around a posterior edge of the carbon fiber foot plate, and a second end of the back strap being coupled with an underside of the carbon fiber foot plate.

In yet another variant, the second end of the back strap is received within a recess that is disposed on the underside of the carbon fiber foot plate.

In yet another variant, the AFO includes a dorsum strap made of webbing material, the dorsum strap being received within two dorsum strap slots disposed on the inner boot.

In yet another variant, the two dorsum strap slots are disposed at an angle greater than zero degrees (0°) and less than ninety degrees (90°) with respect to a bottom plane of the inner boot.

In yet another variant, the dorsum strap has a stopper disposed at one end of the dorsum strap, the stopper configured to be received on an external surface of the inner boot adjacent one of the two dorsum strap slots.

In yet another variant, the stopper is oriented orthogonal to the webbing material of the dorsum strap, the webbing material made up of two layers of webbing material, one layer of the two layers being oriented in a first direction of the stopper, the second layer of the two layers being oriented in a second direction of the stopper, the second direction being opposite from the first direction.

In yet another variant, the AFO further includes a spiral strap made of webbing material that is coupled between the moldable calf piece and the inner boot.

In yet another variant, the spiral strap is received within a mid-foot/fore foot strap slot that is disposed within the inner boot.

In yet another variant, the AFO further includes a calcaneus strap, the calcaneus strap being disposed between the spiral strap and the inner boot.

In yet another variant, the calcaneus strap is received within a calcaneus strap slot that is disposed within the inner boot.

In another aspect, methods of customizing the aforementioned AFO's are disclosed. In one embodiment, the method includes generating a cast model of a patient's lower leg; forming an inner boot around the cast model; and forming a formable layer of a carbon fiber foot plate either around the formed inner boot while the inner boot is placed around the cast model or directly around the cast model.

In one variant, the forming of the inner boot around the cast model further includes: inserting one or more plugs within one or more slots located on the inner boot; heating the inner boot using a heat source, the heating of the inner boot allowing for the inner boot to be shaped around the cast model; and removing the one or more plugs from the one or more slots located on the inner boot. The use of the one or more plugs prevents deformation of the one or more slots located on the inner boot.

In another variant, the method includes attaching a calf shell to a carbon fiber strut that is attached to the carbon fiber foot plate; placing the attached calf shell around the cast model; heating the attached calf shell using a heat source; and forming the heated calf shell around the cast model.

In yet another variant, the method includes inserting a spiral strap comprising a stopper within one or more slots located on the inner boot such that the stopper of the spiral strap is received on an external surface of the inner boot.

In yet another variant, the method includes inserting a key located on the spiral strap into a key hole located on the calf shell.

In yet another aspect, support strap configurations for use with the aforementioned ankle foot orthoses are disclosed.

In yet another aspect, soft goods for use with the aforementioned ankle foot support structures or AFO's are disclosed.

In yet another aspect, methods of manufacturing the aforementioned ankle foot support structures or AFO's are disclosed.

Other features and advantages of the present disclosure will immediately be recognized by persons of ordinary skill in the art with reference to the attached drawings and detailed description of exemplary implementations as given below.

BRIEF DESCRIPTION OF THE DRAWINGS

FIG. 1X-2 is a bottom view of a wearer's foot illustrating points of contact for the helical strap and midfoot strap in one exemplary implementation, in accordance with the principles of the present disclosure.

FIG. 1X-3 is a perspective view of a wearer's foot illustrating the helical strap and midfoot strap in combination with integrated padding, in accordance with the principles of the present disclosure.

FIG. 1X-4 is a bottom view and perspective view of a wearer's foot illustrating placement of the helical strap and midfoot strap of FIG. 1R, in accordance with the principles of the present disclosure.

FIG. 1X-5 is a bottom view and perspective view of a wearer's foot illustrating points of contact for the helical strap and midfoot strap in another exemplary implementation, in accordance with the principles of the present disclosure.

FIG. 1X-6 is a bottom view and perspective view of a wearer's foot illustrating points of contact for the helical strap and midfoot strap in yet another exemplary implementation, in accordance with the principles of the present disclosure.

DETAILED DESCRIPTION

Figure 1A:
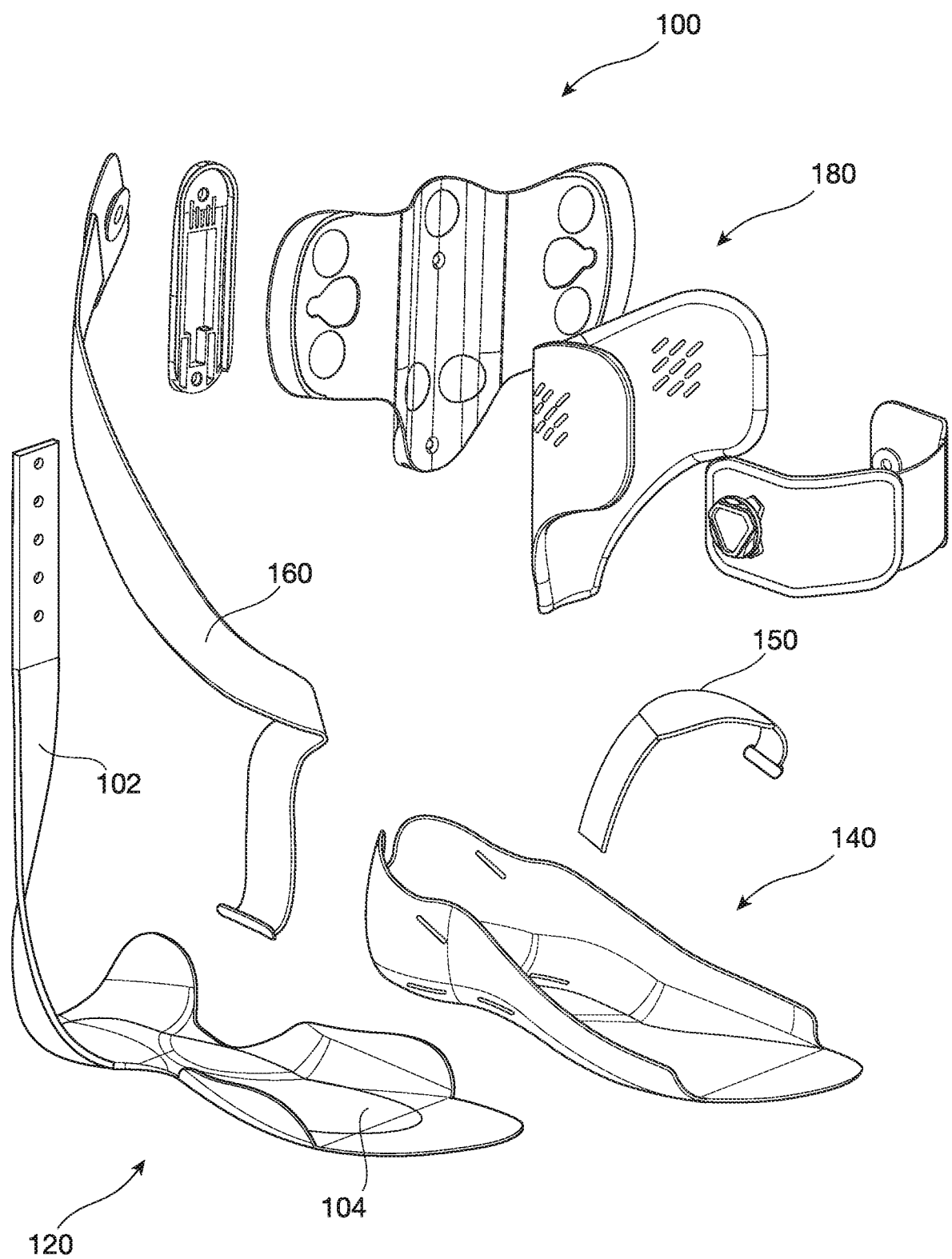
FIG. 1A is an exploded perspective view of a posterior AFO, in accordance with the principles of the present disclosure.

Implementations of the present technology will now be described in detail with reference to the drawings, which are provided as illustrative examples to enable those skilled in the art to practice the technology. Notably, the figures and examples below are not meant to limit the scope of the present disclosure to any single implementation or implementations, but other implementations are possible by way of interchange of, substitution of, or combination with some or all of the described or illustrated elements. Wherever convenient, the same reference numbers will be used throughout the drawings to refer to same or like parts.

In some embodiments, numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention. Unless a contrary meaning is explicitly stated, all ranges are inclusive of their endpoints, and open-ended ranges are to be interpreted as bounded on the open end by commercially feasible embodiments.

Furthermore, while specific embodiments are illustrated and discussed, it would be readily apparent to one of ordinary skill given the contents of the present disclosure that various features illustrated and described within certain embodiments may be bodily incorporated into other disclosed embodiments. For example, various features disclosed within, for example, FIGS. 1A-1X-6 may be readily incorporated into other disclosed variants including, for example, those variants shown with respect to FIGS. 2A-3I and vice versa. Additionally, the customization methodologies illustrated in FIGS. 4A-4Q may be utilized with any of the ankle foot orthoses (AFO) shown with respect to FIGS. 1A-3I with proper adaptation, as would be understood by one of ordinary skill, given the contents of the present disclosure. Finally, it would be readily understood to one of ordinary skill given the contents of the present disclosure that the soft goods illustrated in FIGS. 5A-13C may be utilized in combination with the AFO's shown in FIGS. 1A-3I, and/or alternatively from the inner boots 140 illustrated in FIGS. 1A, 1G-1I, 1K-1P, 1S, 1T, 2A-2C and 3A-3I. These and other variants would be readily apparent to one of ordinary skill given the contents of the present disclosure.

Exemplary Ankle Foot Support Structures—

Referring now to FIG. 1A, one exemplary ankle foot orthoses (AFO) 100 is shown and described in detail. As discussed herein, the terms posterior, anterior, lateral and medial are used to describe the positioning of certain features of the AFO devices 100 described herein. The use of these terms is synonymous with the use of those terms with respect to the anatomy of the wearer and would be understood as such given the contents of the present disclosure. The AFO 100 illustrated in FIG. 1A is also known as a posterior AFO in that the strut assembly 120 illustrated in, for example, FIG. 1A is designed to exit the foot plate 104 near the hind foot of the wearer of the AFO 100 where the strut 102 spirals around the ankle of the wearer and extends upward posterior to the wearer's lower leg. As illustrated in FIG. 1A, the strut 102 exits on the lateral side of the foot plate 104, although it would be appreciated that alternative variants may exit on the medial side of the foot plate 104. Such a variant would be dependent upon the physical condition of the wearer that the AFO 100 is intended for. The AFO 100 may also consist of an inner boot assembly 140, a spiral support strap assembly 160 (also known as a so-called "helix band"), and a calf piece assembly 180.

Figure 1B:
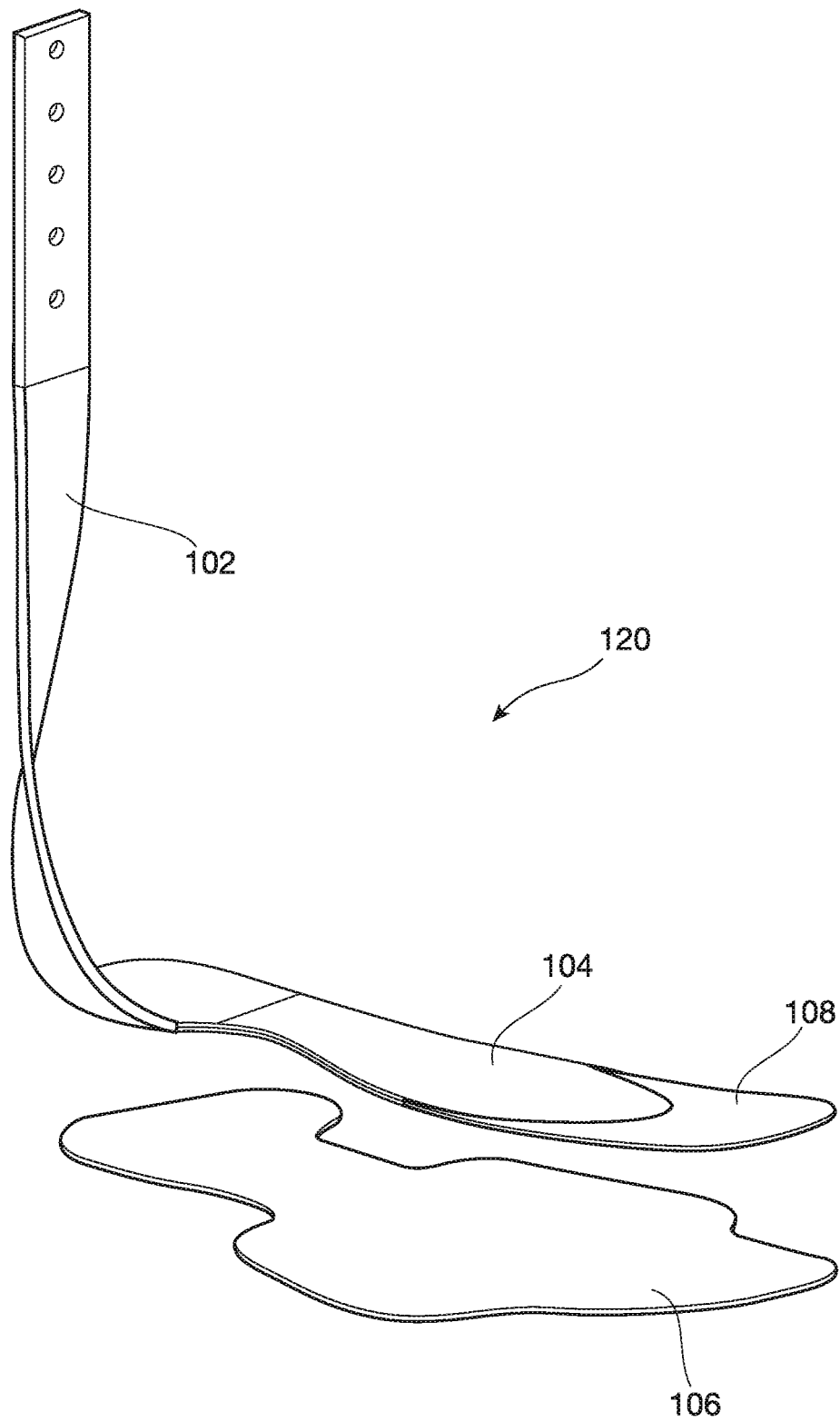
FIG. 1B is an exploded perspective view of the strut and footplate of the AFO shown in FIG. 1A, in accordance with the principles of the present disclosure.

Referring now to FIGS. 1B-1E, various features of the strut assembly 120 are shown and described in detail. As shown in FIG. 1B, the strut assembly 120 may include a strut 102 that may be manufactured from carbon fiber material and a foot plate 104 that may also be constructed from carbon fiber. The trimmable toe area 108 of the foot plate 104 may be made from, for example, fiber glass. One beneficial function for the trimmable toe area 108 is to allow for the trimming of the foot plate assembly 110 to enable the foot plate assembly 110 to accommodate a variety of differing foot sizes. The formable layer 106 of the strut assembly 120 may be manufactured from, for example, a thermoplastic material or other formable or moldable materials which enables for trimming (again to accommodate a wide variety of differing anatomies) as well as the ability for this formable layer 106 to be molded around the foot of a wearer thereby providing for additional support to the wearer (as shown in, for example, FIG. 1E). As shown in FIG. 1B, the formable layer 106 may be positioned underneath the foot plate 104, although it would be readily appreciated that the formable layer 106 may be positioned above the foot plate 104 in some implementations. The formable layer 106 may be modified into a variety of shapes to capture more (or less) foot area for a given wearer of the AFO 100 as one beneficial function of the AFO 100 is to enable a single design (or a limited subset of designs) to accommodate a wide variety of user anatomies.

Figure 1C:
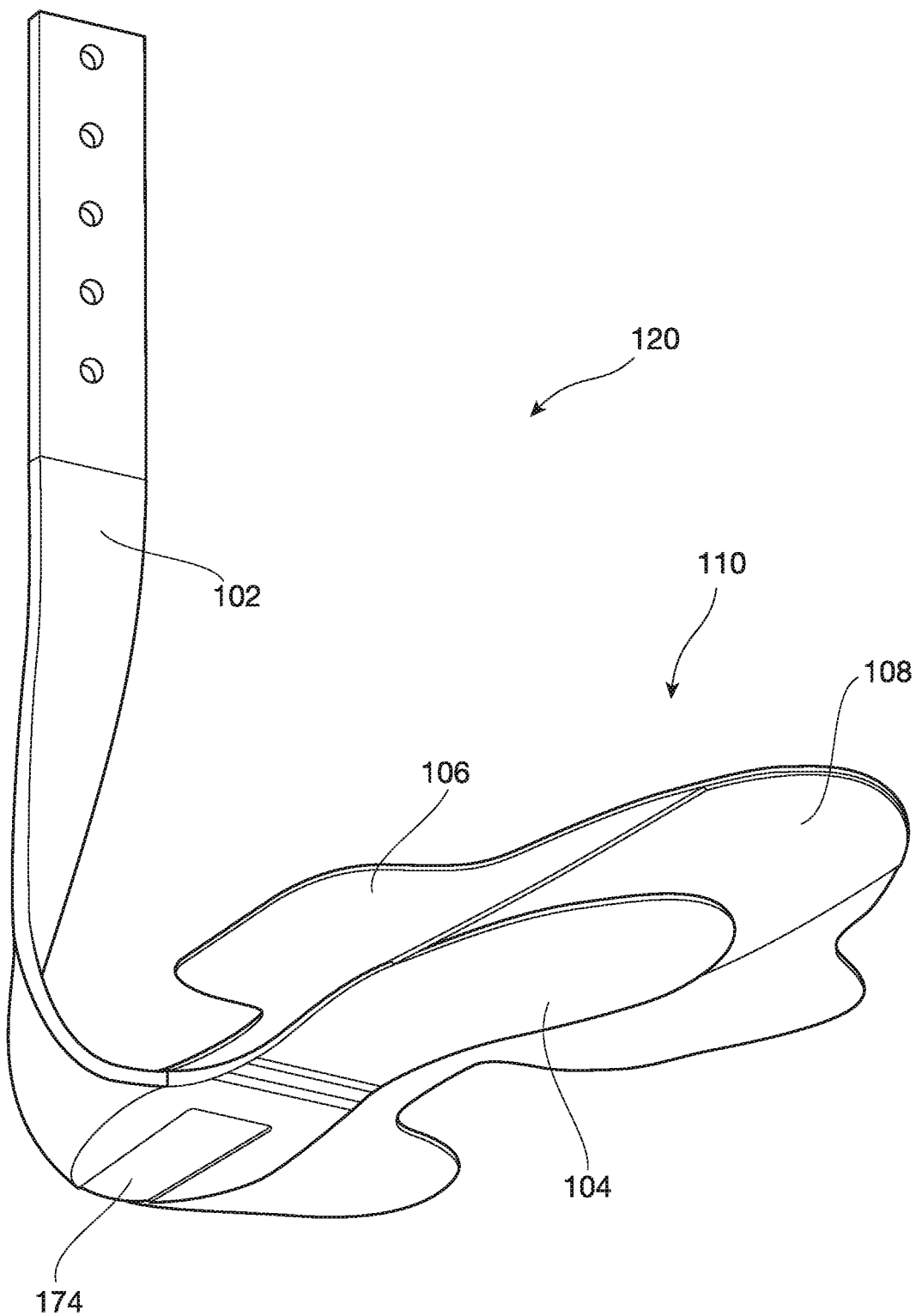
FIG. 1C is a bottom perspective view of the strut and footplate of the AFO shown in FIG. 1A, in accordance with the principles of the present disclosure.
Figure 1D:
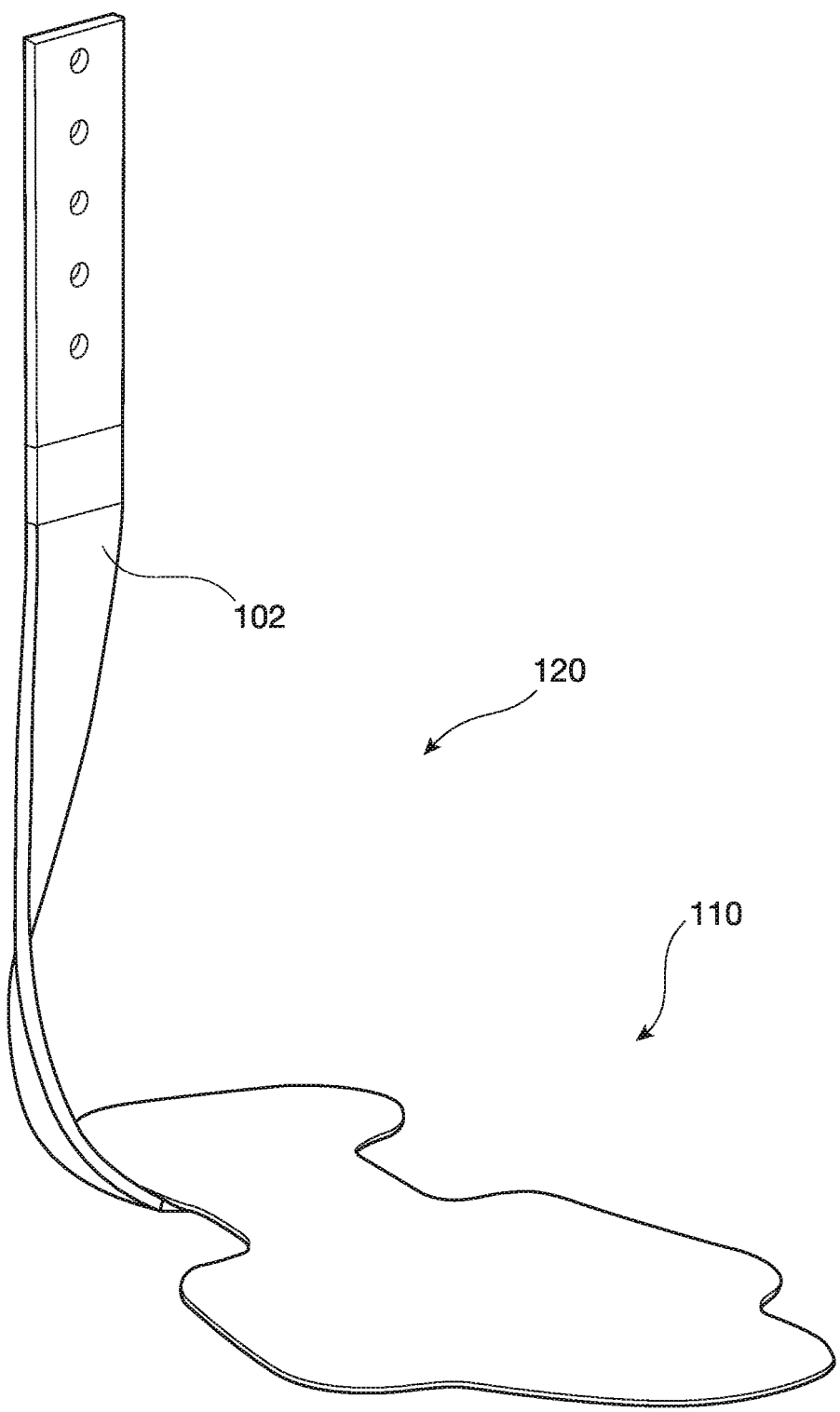
FIG. 1D is a top perspective view of the strut and footplate of the AFO shown in FIG. 1A, in accordance with the principles of the present disclosure.

Referring now FIGS. 1C and 1D, the strut assembly 120 may be manufactured using a variety of different methodologies. The foot plate 104 may also include a recess 174 to accommodate the strap (154, FIG. 4H) that is used to secure the inner boot 142 to the strut assembly 120. For example, in one exemplary methodology, the foot plate 104, the trimmable toe area 108, and the formable layer 106 may be assembled into a double-sided tool where resins are added, and heat and pressure are applied. See also FIG. 1V. Such a manufacturing methodology may be advantageous in that the entire foot plate assembly 110 for the strut assembly 120 may be manufactured in a single step. Such a methodology enables for precise tolerances to be maintained on the bonding and layering of, for example, the carbon fiber, thermoplastic and fiberglass materials. As but another non-limiting manufacturing methodology, the foot plate 104 and trimmable toe area 108 may be pressed (and/or bonded) together in a first processing step. The formable layer 106 may then be over molded over the top, over the bottom, and/or on the edges of the foot plate 104/trimmable toe area 108 layers and/or around the entire foot plate 104 or a combination of the foregoing techniques. See also FIG. 1W. In some implementations, attachment geometries may be added to the foot plate 104 and/or trimmable toe area 108 to ensure that the formable layer 106 adheres properly during over molding thereby creating the final foot plate assembly 110. For example, the foot plate 104 may include a lip on the edge of the foot plate 104 and/or holes located throughout the foot plate 104 which allows the formable layer 106 to strongly bond around the foot plate 104. In some implementations, the formable layer 106 may be separately molded from other portions of the foot plate assembly 110 and glued or otherwise attached to the foot plate assembly 110. Other manufacturing methodologies may be envisioned given the contents of the present disclosure.

Figure 1E:
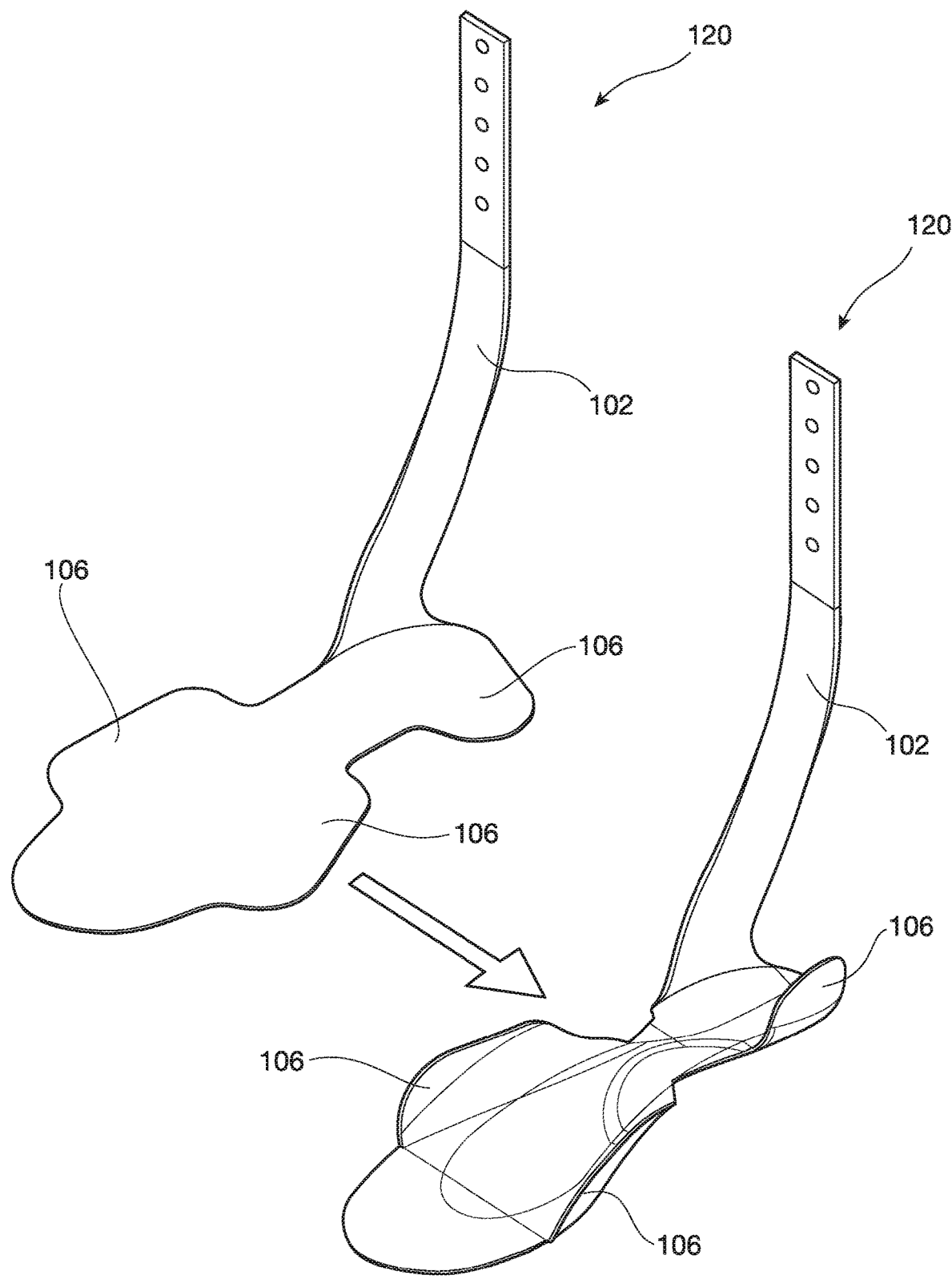
FIG. 1E are perspective views of the strut and footplate of the AFO shown in FIG. 1A illustrating the formability of the footplate, in accordance with the principles of the present disclosure.

Regardless of the specific manufacturing methodology chosen, such methodologies enable the foot plate 104 to be universal (or near universal) to a variety of different anatomies, while the formable 106 and trimmable toe area 108 layers may accommodate a wide variety of users and can be adjusted for a particular anatomy outside of a traditional manufacturing setting. Such methodologies enable quick, easy and consistent adjustments to be made as compared with a custom carbon fiber AFO that needs to be produced in a manufacturing setting. In other words, the AFO 100 of the present disclosure may be much more efficient to produce for a particular wearer as compared with a carbon fiber footplate that must be molded into shape based on a particular user's anatomy. FIG. 1E illustrates the formable layer 106 being molded post-production so that this formable layer 106 can be shaped around a user's foot.

Figure 1F:
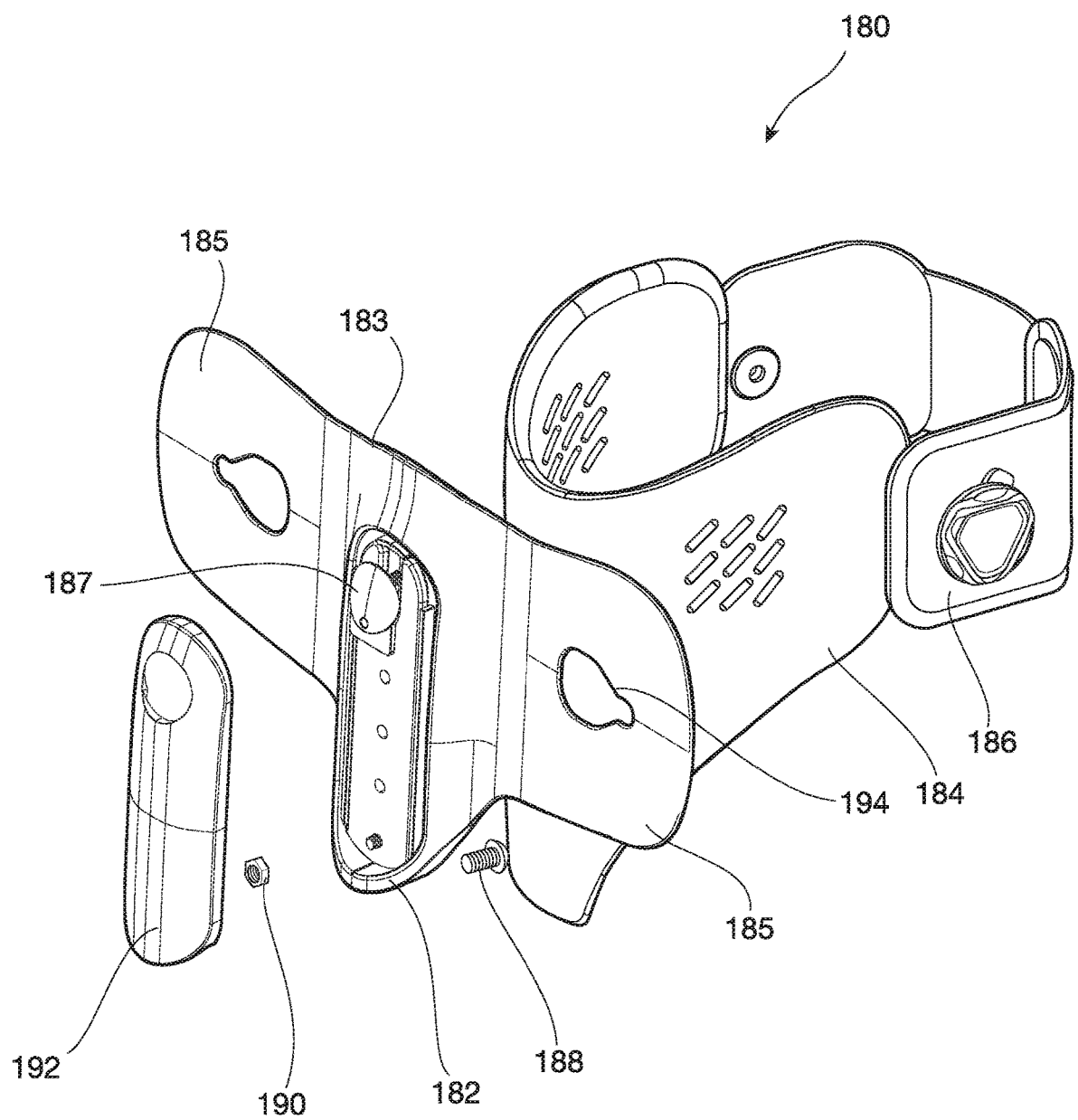
FIG. 1F is an exploded perspective view of the calf piece of the AFO shown in FIG. 1A, in accordance with the principles of the present disclosure.

Referring now to FIG. 1F, an exploded view of an exemplary calf piece assembly 180 is shown and described in detail. As shown, the calf piece assembly 180 includes a calf strap 186 with a rotary tensioning mechanism that helps secure the calf piece assembly 180 around the calf of a wearer of the AFO 100. In some implementations, the calf strap 186 may include strapping with, for example, hook and loop fasteners such that the calf strap 186 may be tightened around, for example, a D-ring located on the calf shell 182. The calf piece assembly 180 may also include a calf shell 182 and a liner 184. The calf piece assembly 180 may be secured to the strut 102 via, for example, the use of one or more threaded bolts 188 and one or more nuts 190 or other attachment mechanisms. The calf piece assembly 180 may also include a head/nut cover 192 for covering a portion of the strut 102 and, for example, the nut 190/bolt 188 which attaches the calf piece assembly 180 to the strut 102. A removable cap 187 may also cover a keyhole 170 located on the back of the calf piece assembly 180. The keyhole 170 may serve as an attachment point for the spiral strap (164, FIG. 1K). When the spiral strap is not being used, the removable cap 187 may remain in place on the calf shell 182. However, when the spiral strap is being used, the removable cap 187 may be removed from the calf shell 182 exposing the keyhole 170.

In some implementations, the calf shell 182 may be manufactured from a heat-formable thermoplastic that is over-molded around a cold formable material such as, for example, aluminum. In such an implementation, the calf piece assembly 180 may be adjustable in circumference enabling the calf piece assembly 180 to fit a wide variety of anatomies making the calf piece assembly 180 universal in nature. In such an implementation, the areas around the keyholes 194 and the portion of the calf piece assembly 180 that interfaces with the strut 102 may be non-deformable in nature, especially in implementations in which the calf piece assembly 180 (and in particular, the calf shell 182) are heated in order to mold the calf piece assembly 180 into shape in order to adapt to a specific anatomy for the wearer. In some implementations, the calf piece assembly 180 can be molded into shape without requiring the application of heat. For example, an aluminum stay may be over molded with a flexible polymer. In such an implementation, an aluminum stay (or bending irons) can be bent to shape using, for example, the hands of a certified clinician without necessarily requiring the application of heat to the calf shell 182.

In some implementations, the liner 184 may include a thermoplastic layer that is disposed inside of the liner 184 which can be bent to shape using, for example, heat. The thermoplastic layer may be placed in the middle of the back of the liner 184 which allows the liner 184 to be customizable to accommodate a wide variety of differing anatomies. The liner 184 may also be utilized as a guide when shaping the thermoplastic (and/or cold formable materials) located in the calf piece 182. The calf piece 182 may also be manufactured from a high temperature thermoplastic that is over molded with a lower temperature thermoplastic in areas that need to be formed. For example, the main body portion 183 of the calf piece 182 (as well as areas surrounding the key holes 194 in some implementations) may be primarily formed from a high temperature thermoplastic, while other portions of the calf piece 182 such as the wing portions 185 of the calf piece 182 may be primarily manufactured from a thermoplastic. Such an implementation may enable the calf piece assembly 180 to be formed to accommodate a wide variety of user anatomies using, for example, heat for the shaping of the calf piece 182. The liner 184 may be attached to the calf shell 182 using, for example, hook and loop fasteners, magnets on the liner 184 and/or shell 182, snap fits, and/or injection molded hooks that are permanently molded into the calf shell 182 or snapped into the calf shell 182 after forming the calf piece assembly 180. Other attachment methodologies may be utilized as well with the primary goal being the alignment of the liner 184 to the calf shell 182. FIG. 1F also illustrates a calf shell 182 that is designed in a generic relatively flat shape so that a clinician can mold the calf shell 182 to fit a variety of anatomical shapes as described elsewhere herein.

Figure 1G:
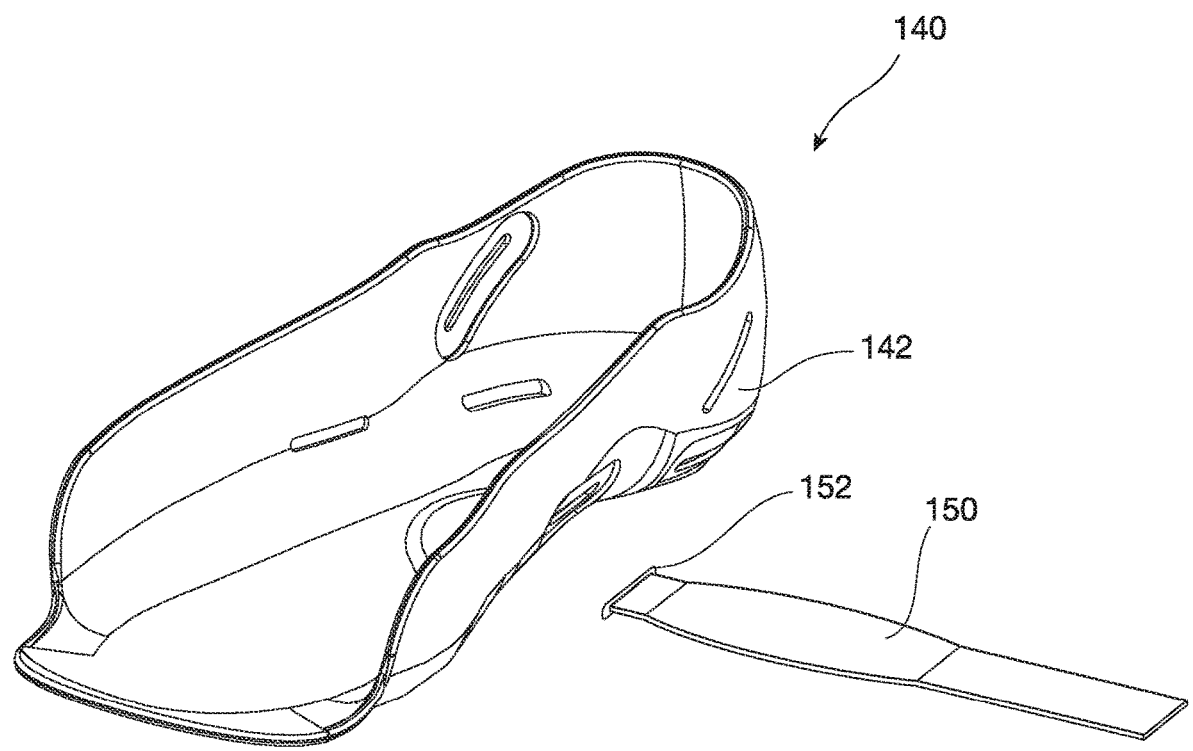
FIG. 1G is a perspective view of an inner boot with dorsum strap for use with the AFO of FIG. 1A, in accordance with the principles of the present disclosure.
Figure 1H:
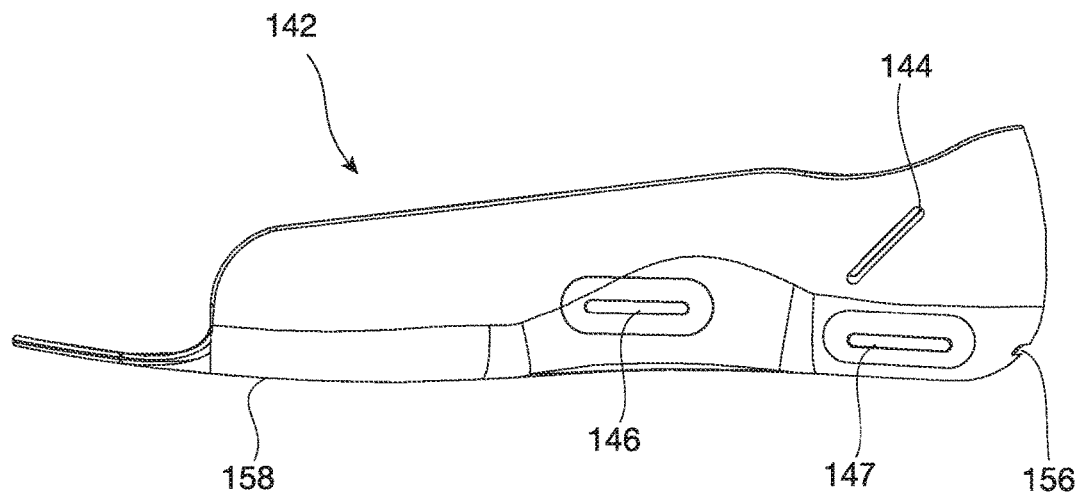
FIG. 1H is a side elevation view of the inner boot of FIG. 1G, in accordance with the principles of the present disclosure.
Figure 1I:
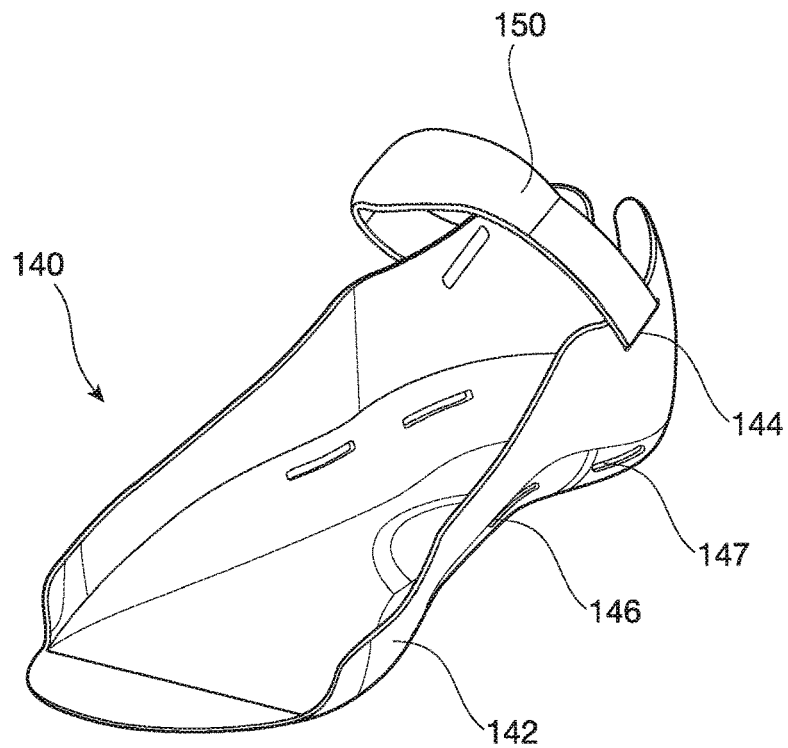
FIG. 1I is a perspective view of the inner booth with dorsum strap installed for use with the AFO of FIG. 1A, in accordance with the principles of the present disclosure.

Referring now to FIGS. 1G-1I, an implementation of the inner boot assembly 140 is shown and described in detail. The inner boot assembly 140 may consist of an inner boot 142 as well as a dorsum strap 150. The inner boot 142 may consist of a thermoformable polymer in some implementations. For example, the inner boot 142 may be constructed from polyethylene or a co-polymer polypropylene which has moderate rigidity, excellent formability, and good stress crack resistance. Direct attachment of straps, such as the dorsum strap 150, to the inner boot 142 involves the utilization of slots 144, 146, 147 on the inner boot 142. Plugs manufactured from, for example, silicone or other suitable materials may be inserted into the slots 144, 146, 147 during heat forming of the inner boot 142 to prevent the distortion of these slots 144, 146, 147 during the heat forming process.

The inner boot 142 may be attachable to the foot plate 104 via, for example, the formable layer 106 located on the foot plate 104. Other methodologies may include the use of hook and loop fasteners, rivets or snap fit mechanisms, the molding of a thin strap onto the foot plate 104 (or inner boot 142) and/or a moldable foot plate with a mechanism to lock down the strap/inner boot, thereby resulting in the anchoring of the inner boot 142 to the foot plate 104. Referring now to FIGS. 1R through 1T, one such attachment methodology is illustrated. FIG. 1R illustrates an attachment point 173 for the strap 175 illustrated in FIG. 1S. The attachment point 173 may allow the strap 175 to be attached to the foot plate 104 using an adhesive, hook and loop fasteners, screws, snap fit features, and/or other means of attachment. The strap 175 may then be routed around the edge of the foot plate 104 as shown in FIG. 1S, where it is anchored to the inner boot 142 at anchor point 177 as shown in FIG. 1T at the posterior plantar surface of the inner boot 142.

In some implementations, such as that shown in FIG. 1H, the inner boot 142 may also include a posterior slot 156. The back strap (154, FIG. 4H) may be secured to the interior bottom surface of the inner boot 142 (e.g., near the hind foot region for the wearer of the inner boot 142). The back strap (154, FIG. 4H) may be secured to the inner boot 142 using, for example, a pressure sensitive adhesive (PSA), rivets, bolts, sewing and other types of attachment mechanisms for securing the back strap (154, FIG. 4H) to the inner boot 142. The back strap (154, FIG. 4H) may be threaded through the posterior slot 156 and around the posterior portion of the foot plate 104. The back strap (154, FIG. 4H) may be trimmed to length so that the end of the back strap 154 fits within the recess 174 of the foot plate 104. The back strap (154, FIG. 4H) may be secured to the underside of the foot plate 104 using PSA, rivets, bolts, sewing and other types of attachment mechanisms for securing the back strap (154, FIG. 4H) to the foot plate 104. The length of the back strap (154, FIG. 4H) may be adjustable to enable, for example, a heel wedge or other lifting components to be inserted between the inner boot 142 and the foot plate 104. The use of a heel wedge or other lifting components may be dependent upon the specific requirements for the wearer of the AFO 100. The underside of the inner boot 142 may also include an attachment point 158 at an anterior portion of the inner boot 142. The purpose of this attachment point 158 is to secure the inner boot 142 to the foot plate 104 and to ensure the inner boot 142 is in correct alignment. This alignment of the inner boot 142 within the AFO 100 may be critical dependent upon a given patient's anatomy and needs and will also ensure that the inner boot 142 does not shift when worn by the patient.

As perhaps best viewed with respect to FIG. 1H, the inner boot 142 may include a plurality of slots 144, 146, 147. For example, as illustrated in FIG. 1H, the inner boot 142 may include a pair of dorsum strap slots 144, a pair of mid-foot/fore foot strap slots 146, and a pair of calcaneus strap slots 147. The mid-foot/fore foot strap slots 146 and calcaneus strap slots 147 are oriented such that the longest dimension for these slots 146, 147 runs generally parallel with the bottom plane of the inner boot 142, while the dorsum strap slots 144 are oriented at an angle with respect to the bottom plane of the inner boot 142. This angle may be between 0° and 90°, may be between 30° and 60°, or may be approximately 45°. As shown in FIG. 1I, the dorsum strap 150 is threaded through one of the dorsum strap slots 144 such that the stopper 152 on the dorsum strap 150 is situated on the interior surface of the inner boot 142. As a brief aside, and in some implementations, the dorsum strap 150 may consist of two layers of webbing material. When the two layers of webbing material are routed into the stopper 152, one layer will protrude upwards into the stopper 152, while the other layer will protrude downwards into the stopper 152. The stopper 152 itself may be manufactured using a thermoplastic polyurethane (TPU) that is molded around the two layers of webbing for the dorsum strap 150. In some implementations, a single layer of webbing may be utilized in a similar fashion by having portions of the webbing protrude upwards into the stopper 152, while other portions of the webbing may protrude downwards into the stopper 152.

In some implementations, the stopper 152 may be positioned within a cavity feature located around the dorsum strap slots 144 to reduce the amount that the stopper 152 protrudes into the interior of the inner boot 142. The dorsum strap 150 is then routed over the top of the inner boot 142 where it is routed through the opposing dorsum strap slot 144. After being routed through the opposing dorsum strap slot 144, the dorsum strap 150 may be tightened around the foot of the wearer of the inner boot 142 using, for example, hook and loop fasteners although other fastening mechanisms such as buttons, hooks and the like may be utilized in alternative variants.

In some implementations, the respective stoppers 162 located on the spiral strap 164 and the calcaneus strap 165 may be constructed and function similar to the stopper 152 located on the dorsum strap 150 as described supra. However, in some implementations, the calcaneus strap 165 and the spiral strap 164 enter from the exterior of the calcaneus strap slot 146 and the mid-foot/fore foot strap slot 147, respectively such that the respective stoppers 162 are positioned on the exterior surface of the inner boot 142. In some implementations, the positioning of the straps 164, 165 may be reversed such that the spiral strap 164 and the calcaneus strap 165 enter from the exterior of the calcaneus strap slot 147 and the mid-foot/fore foot strap slot 146, respectively. In some implementations, the spiral strap 164 may be longer than the calcaneus strap 165. In such an implementation, the spiral strap 164 may be routed between the inner boot 142 and the calf piece assembly 180, while the calcaneus strap 165 may be routed between the inner boot 142 and the spiral strap 164.

The spiral strap 164 and the calcaneus strap 165 may enter the inner boot 142 on either or both of the medial side 141 and the lateral side 143. For example, the calcaneus strap slot 147 and the mid-foot/fore foot strap slot 146 enable the spiral strap 164 and the calcaneus strap 165 to be located in left and/or right orientations for the wearer of the AFO 100. As shown in FIG. 1M, the spiral strap 164 and the calcaneus strap 165 are then routed between the foot of the wearer of the AFO 100 and the interior of the inner boot 142. Accordingly, both the spiral strap 164 and the calcaneus strap 165 are routed around the underside of the wearer of the AFO's 100 foot. Cavities around the perimeter of the calcaneus strap slot 147 and the mid-foot/fore foot strap slot 146 may reduce the profile of the stoppers 162 located on the spiral strap 164 and the calcaneus strap 165, so as to enable the AFO 100 to more comfortably be received within a shoe. In some implementations, the spiral strap 164 and the calcaneus strap 165 may be routed external to the inner boot (i.e., around and/or under the inner boot 142). These straps may all be trimmable to accommodate a variety of anatomical sizes for the patient's wearing these AFOs 100.

Figure 1J:
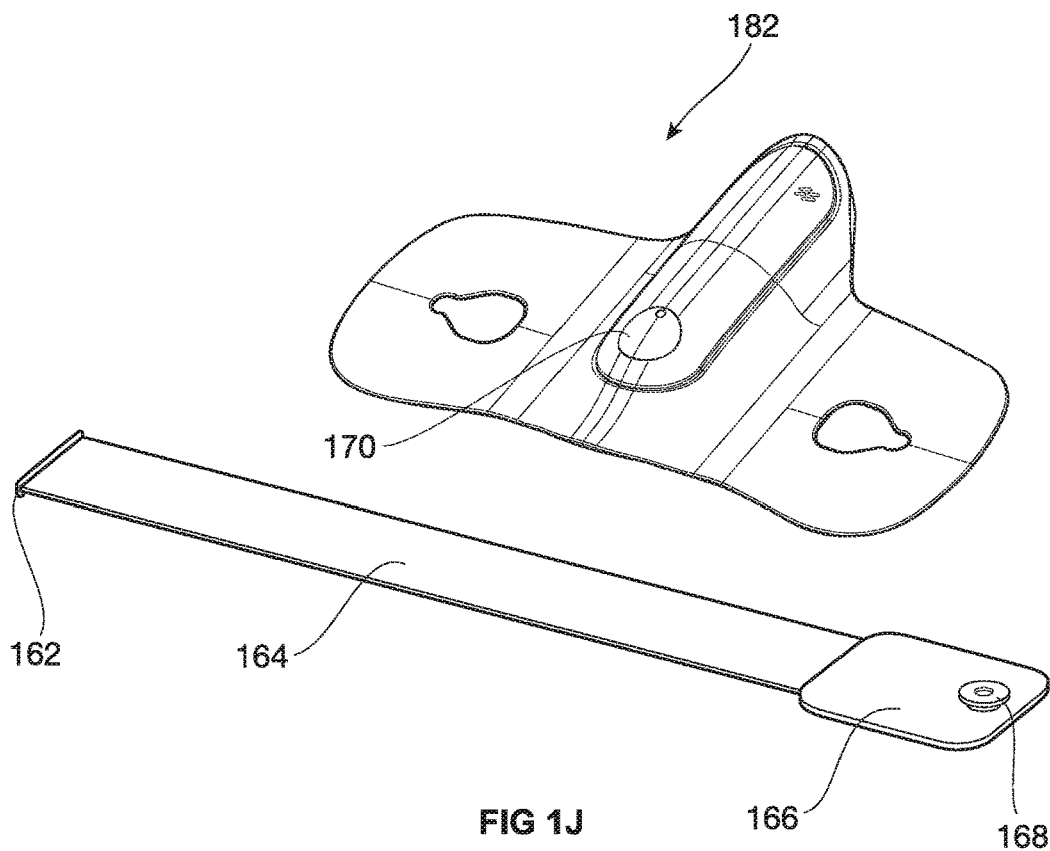
FIG. 1J is a perspective view of the helical strap for use with the AFO of FIG. 1A, in accordance with the principles of the present disclosure.
Figure 1K:
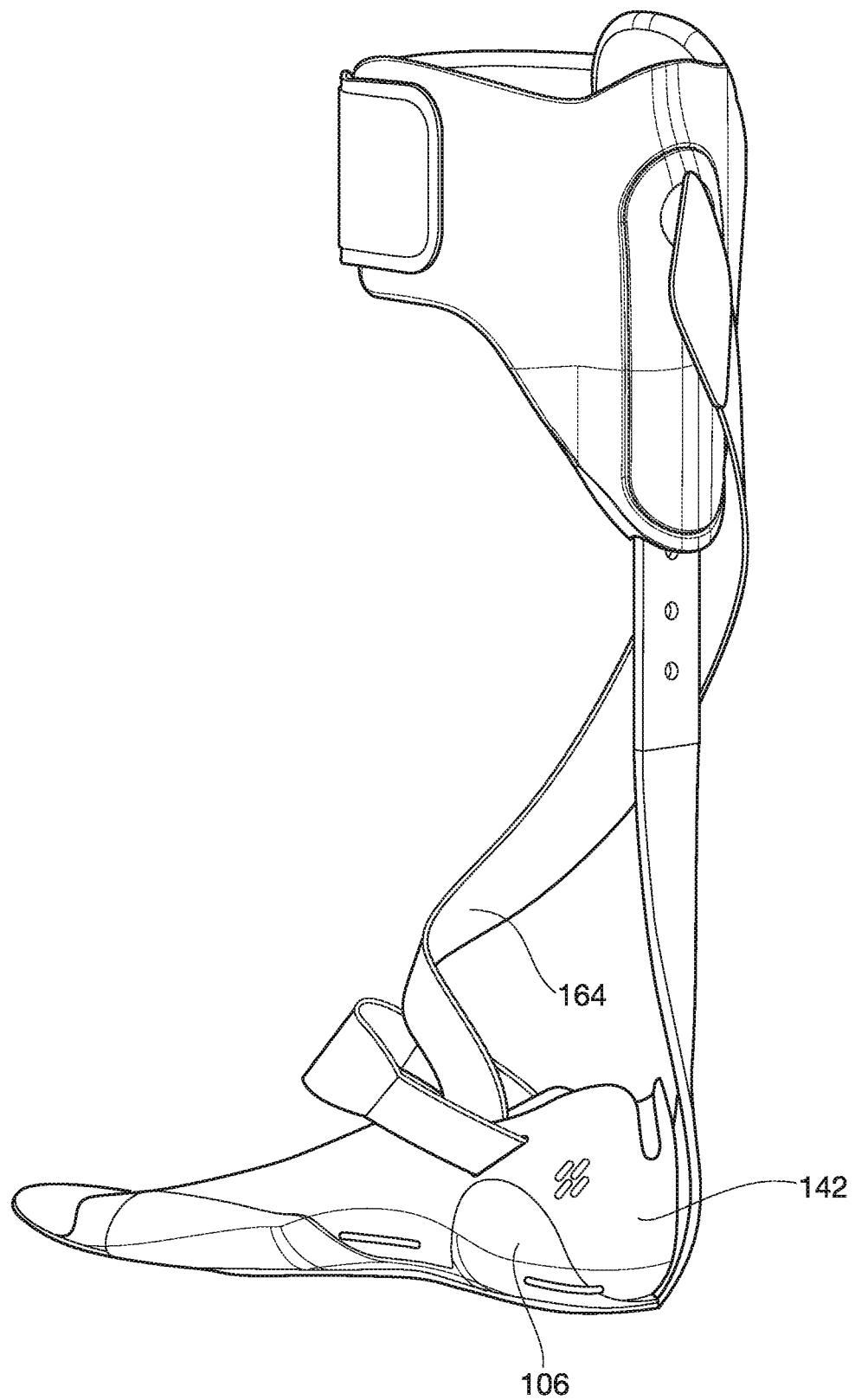
FIG. 1K is a rear perspective view of the AFO of FIG. 1A, in accordance with the principles of the present disclosure.
Figure 1L:
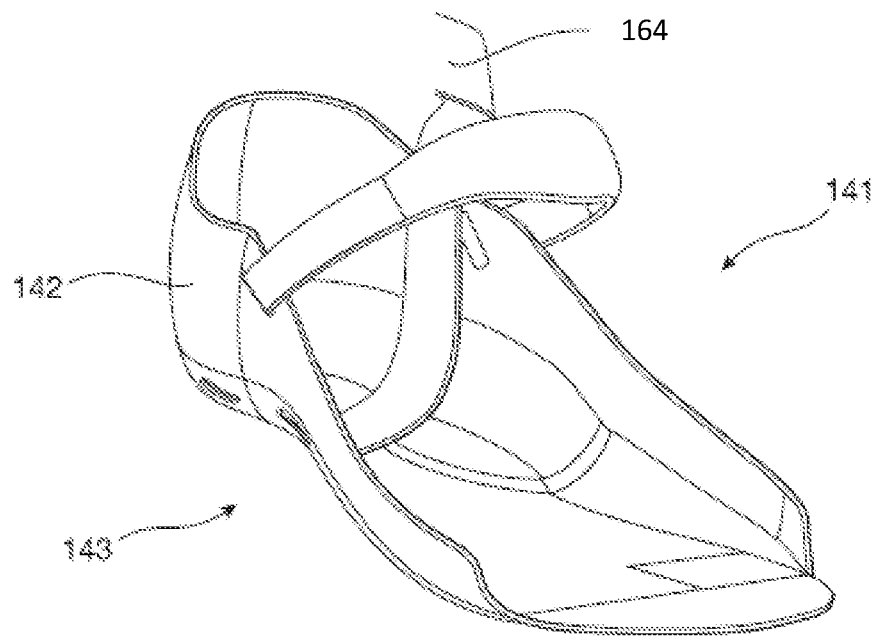
FIG. 1L is a perspective view of the inner boot with helical strap, in accordance with the principles of the present disclosure.
Figure 1M:
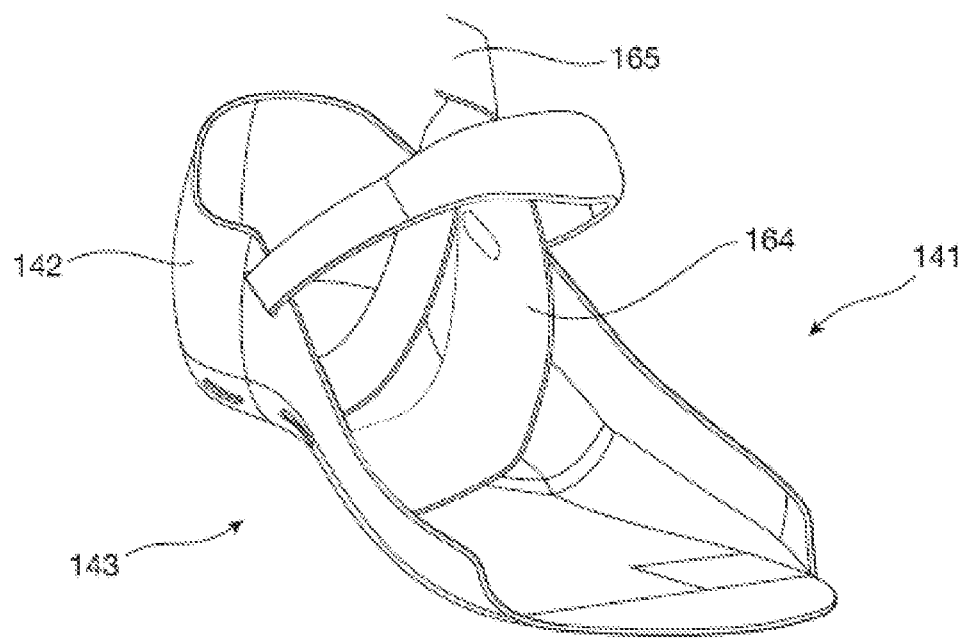
FIG. 1M is a perspective view of the inner boot with helical strap of FIG. 1L with an additional midfoot strap, in accordance with the principles of the present disclosure.
Figure 1N:
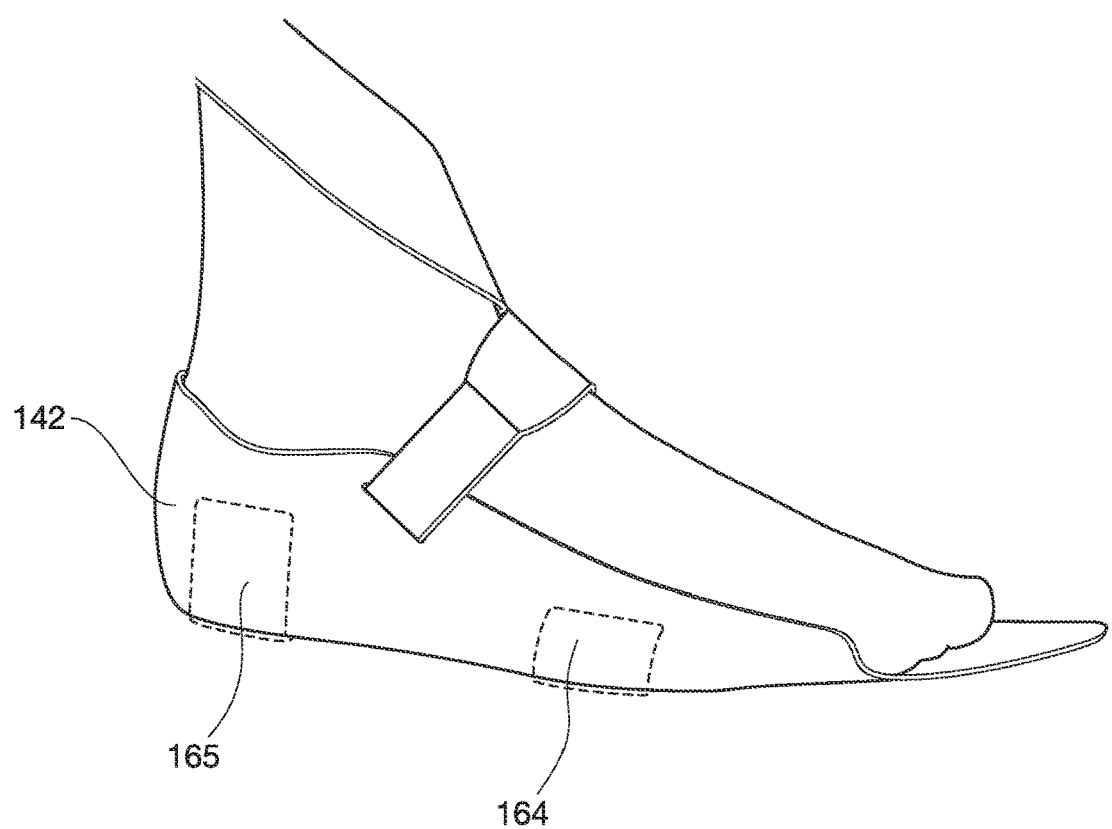
FIG. 1N is a side elevational view of the inner boot from the lateral plane showing placement of the helical strap and midfoot strap underneath the foot, in accordance with the principles of the present disclosure.
Figure 1O:
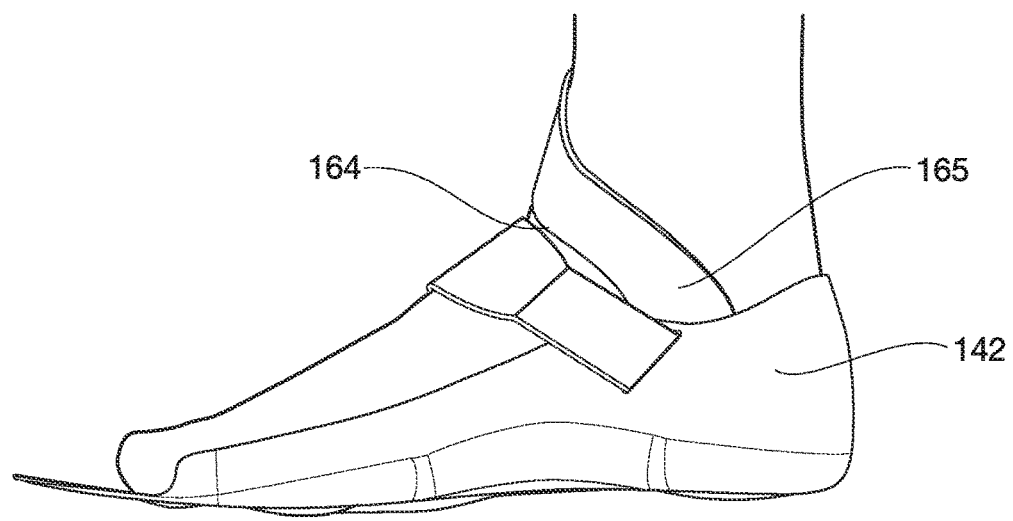
FIG. 1O is a side elevational view of the inner boot from the medial plane showing placement of the helical strap and midfoot strap with respect to a wearer's ankle, in accordance with the principles of the present disclosure.

FIG. 1J illustrates one implementation of the spiral strap 164 that includes a stopper 162 that is configured to be received within either (or both) of the slots 146, 147 located on the inner boot 142. In some implementations, the stopper 162 is attached using a thermoplastic polyurethane (TPU) bonding technique onto the spiral strap 164 as disclosed supra, although other attachment mechanisms such as compression molding, gluing, sewing, riveting, and the like may be utilized in addition to, or alternatively than the aforementioned TPU bonding technique. The spiral strap 164 may include an adjustable strap hook 166 at an opposing end of the support strap 164 in the illustrated embodiment of FIG. 1J. The adjustable strap hook 166 may include a key 168 that is configured to be received within a keyhole located on the back side of the calf piece assembly 180 shown in, for example, FIG. 1F. Similar techniques may be employed to place the stopper 162 onto the calcaneus strap 165 as well as the stopper 152 located on the dorsum strap 150.

Figure 1P:
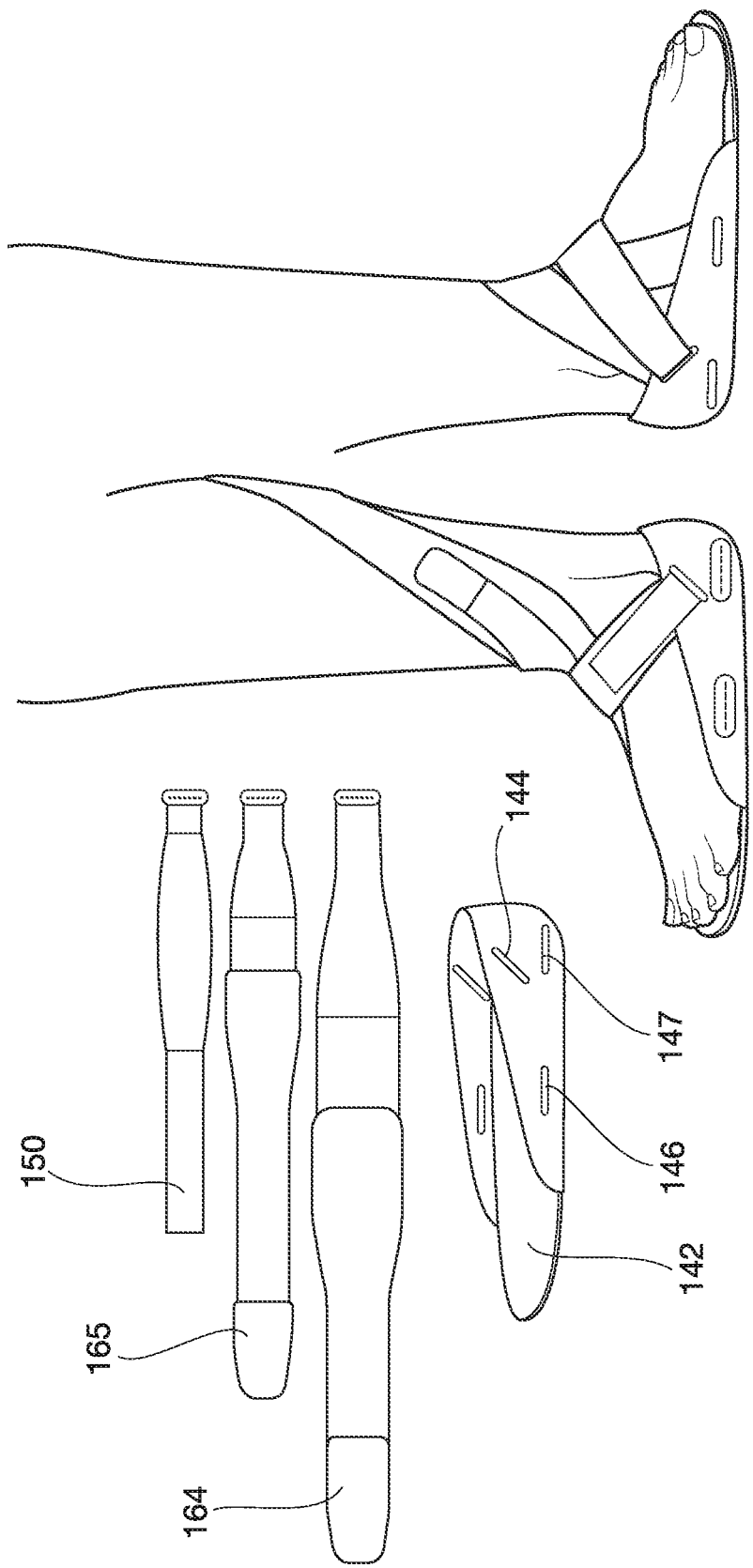
FIG. 1P is an alternative strapping system showing an inner boot, a dorsum strap, a calcaneus strap, and a spiral strap, in accordance with the principles of the present disclosure.
Figure 1Q:
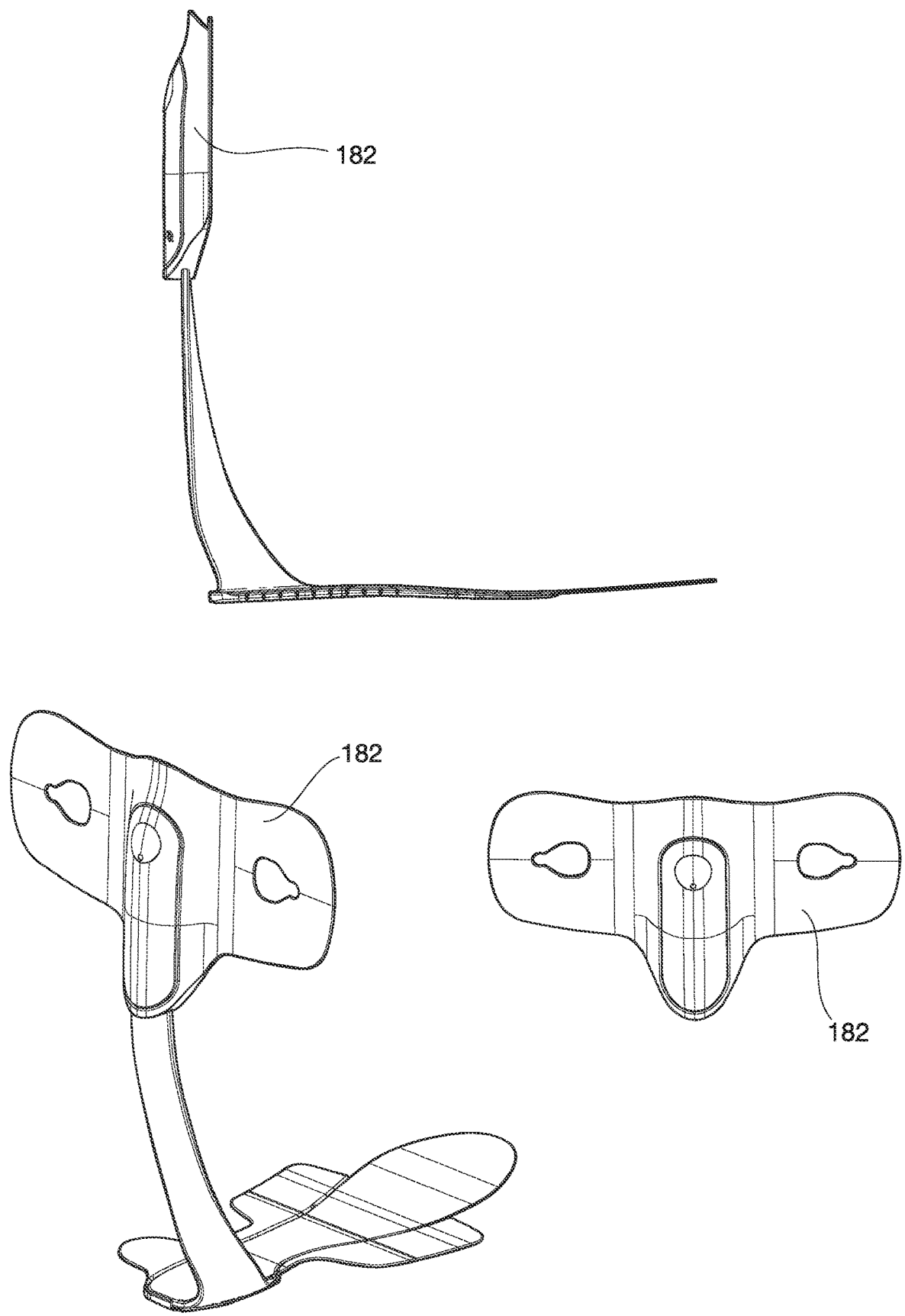
FIG. 1Q illustrate various views of a calf shell, in accordance with the principles of the present disclosure.
Figure 1R:
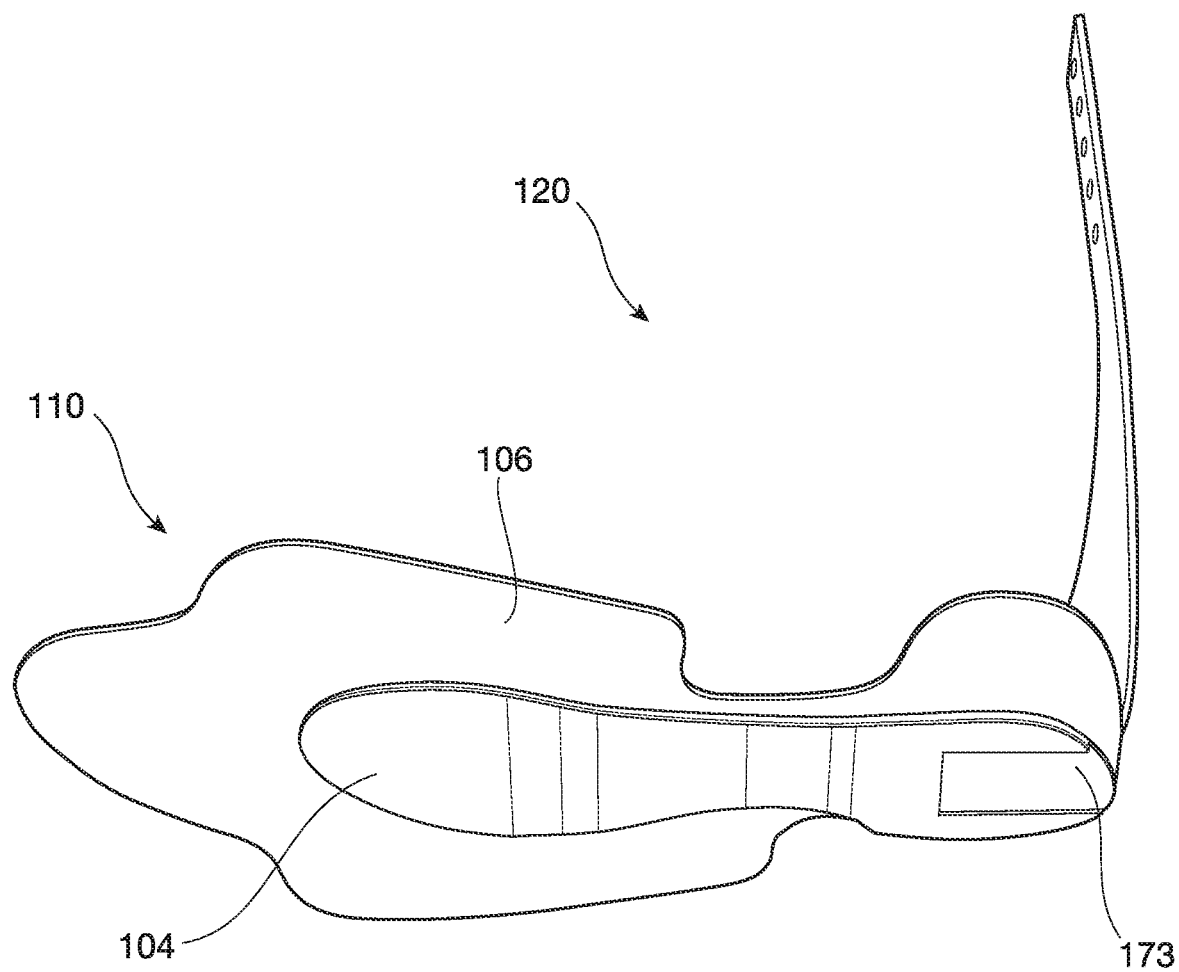
FIGS. 1R through 1T illustrate an attachment methodology for attaching the inner boot to the foot plate, in accordance with the principles of the present disclosure.
Figure 1S:
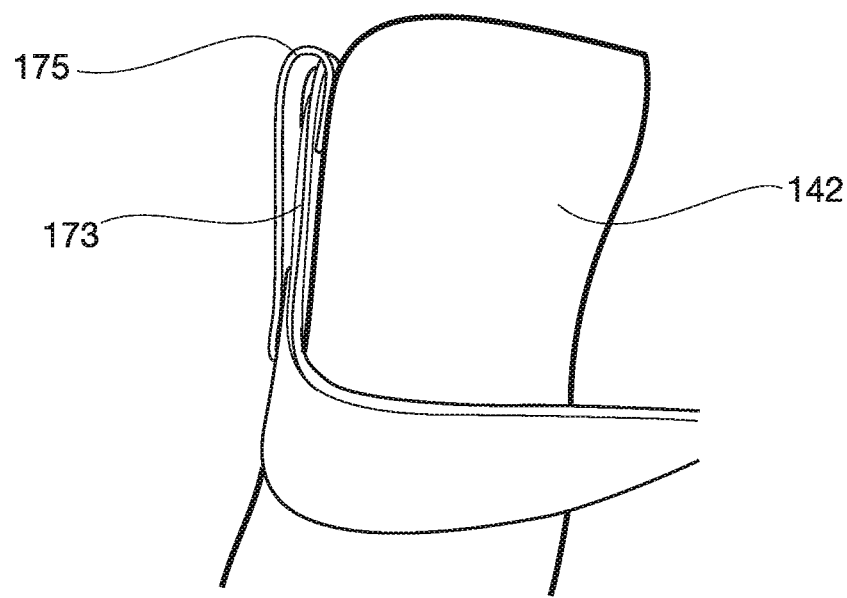
Figure 1T:
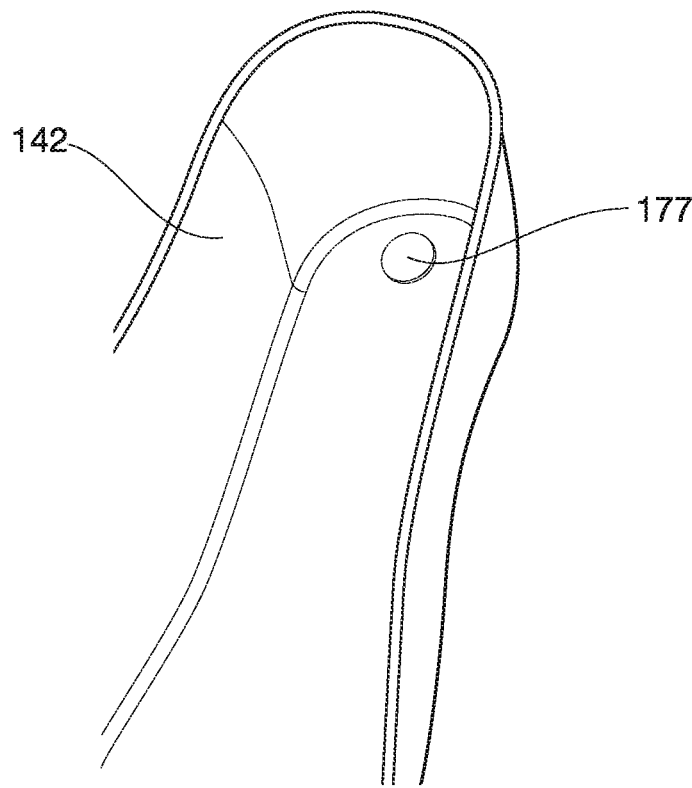
Figure 1U:
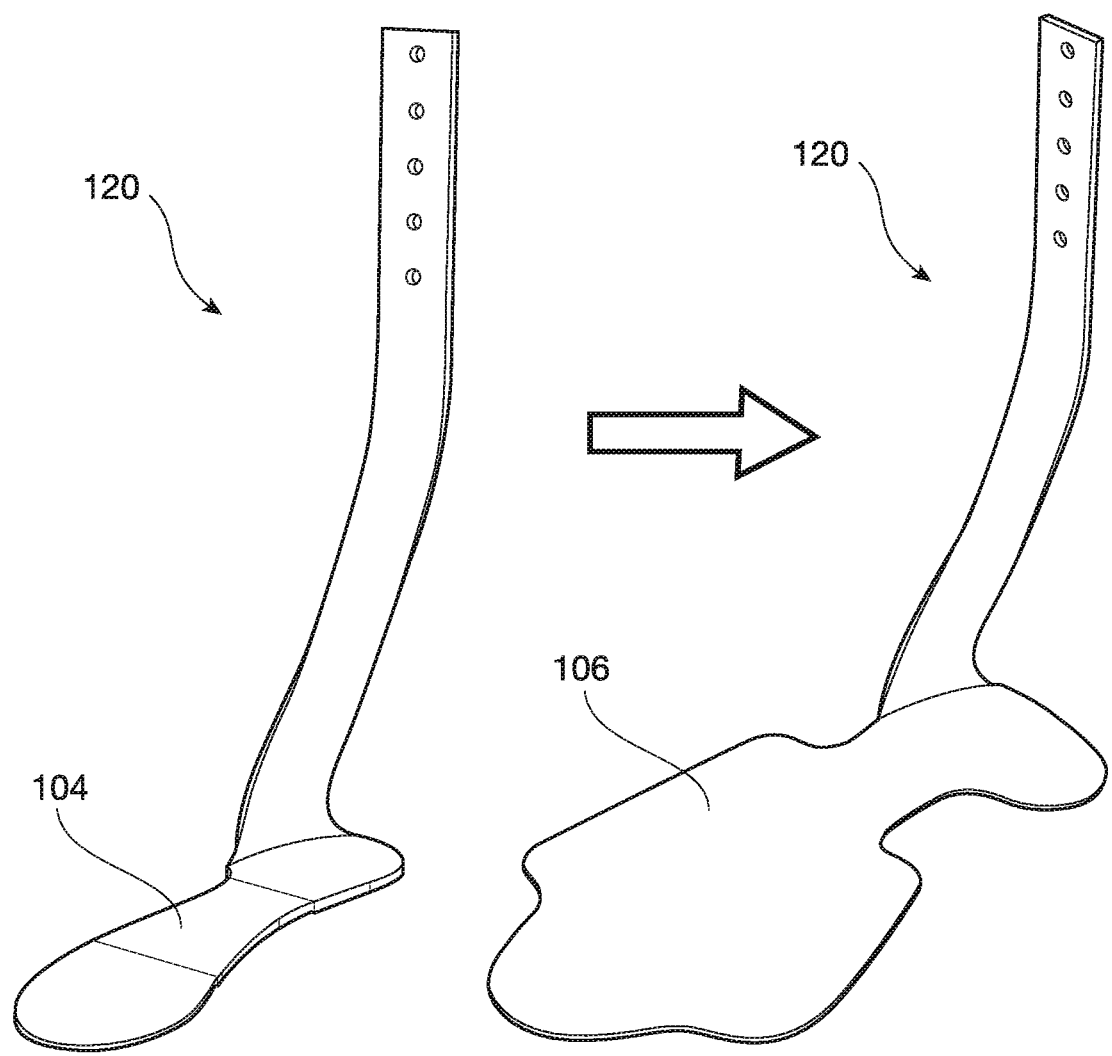
FIG. 1U illustrates the attachment of a formable layer to a carbon fiber foot plate, in accordance with the principles of the present disclosure.
Figure 1V:
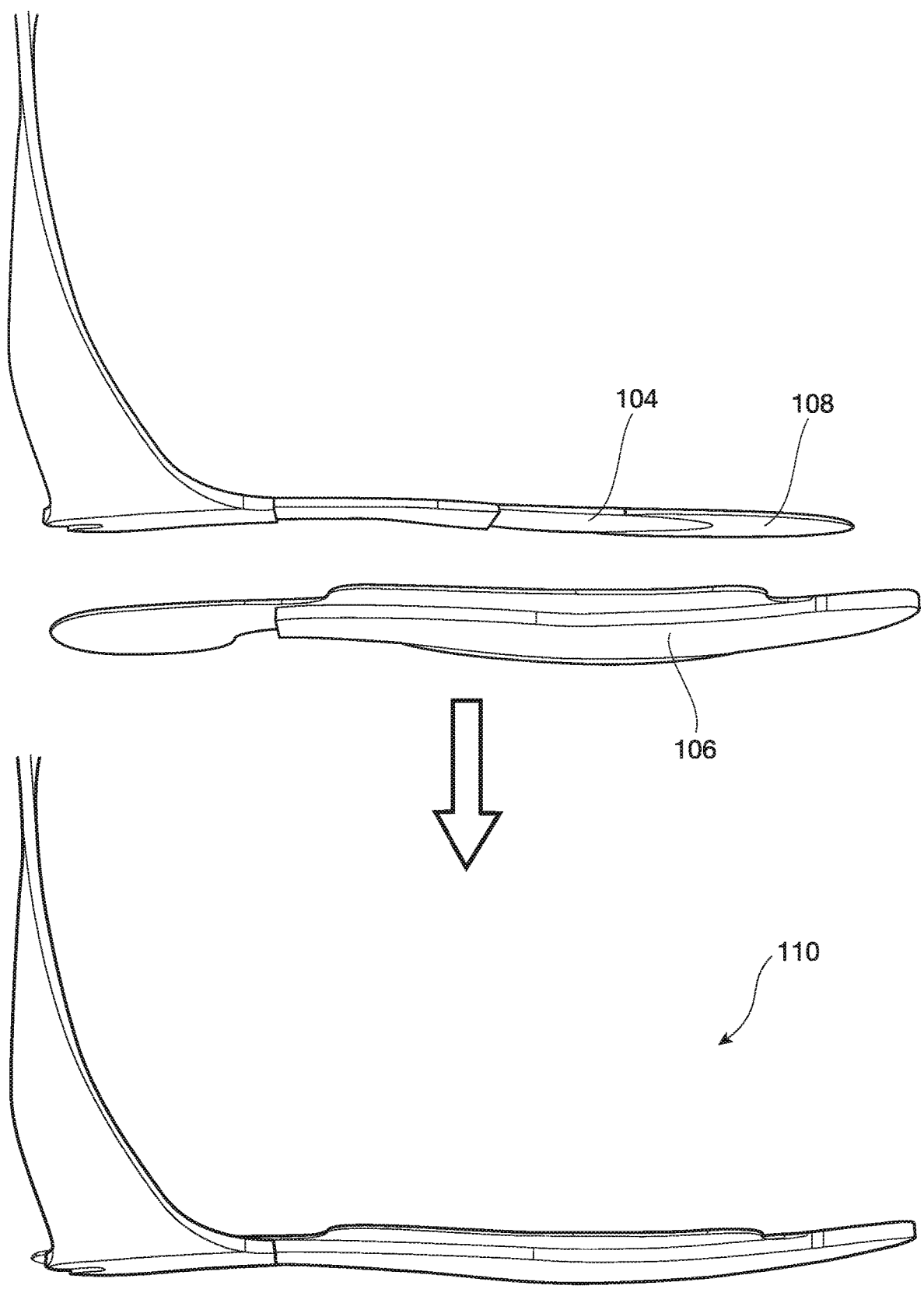
FIG. 1V illustrates the attachment of the formable layer to the carbon fiber foot plate using an over molding technique, in accordance with the principles of the present disclosure.
Figure 1W:
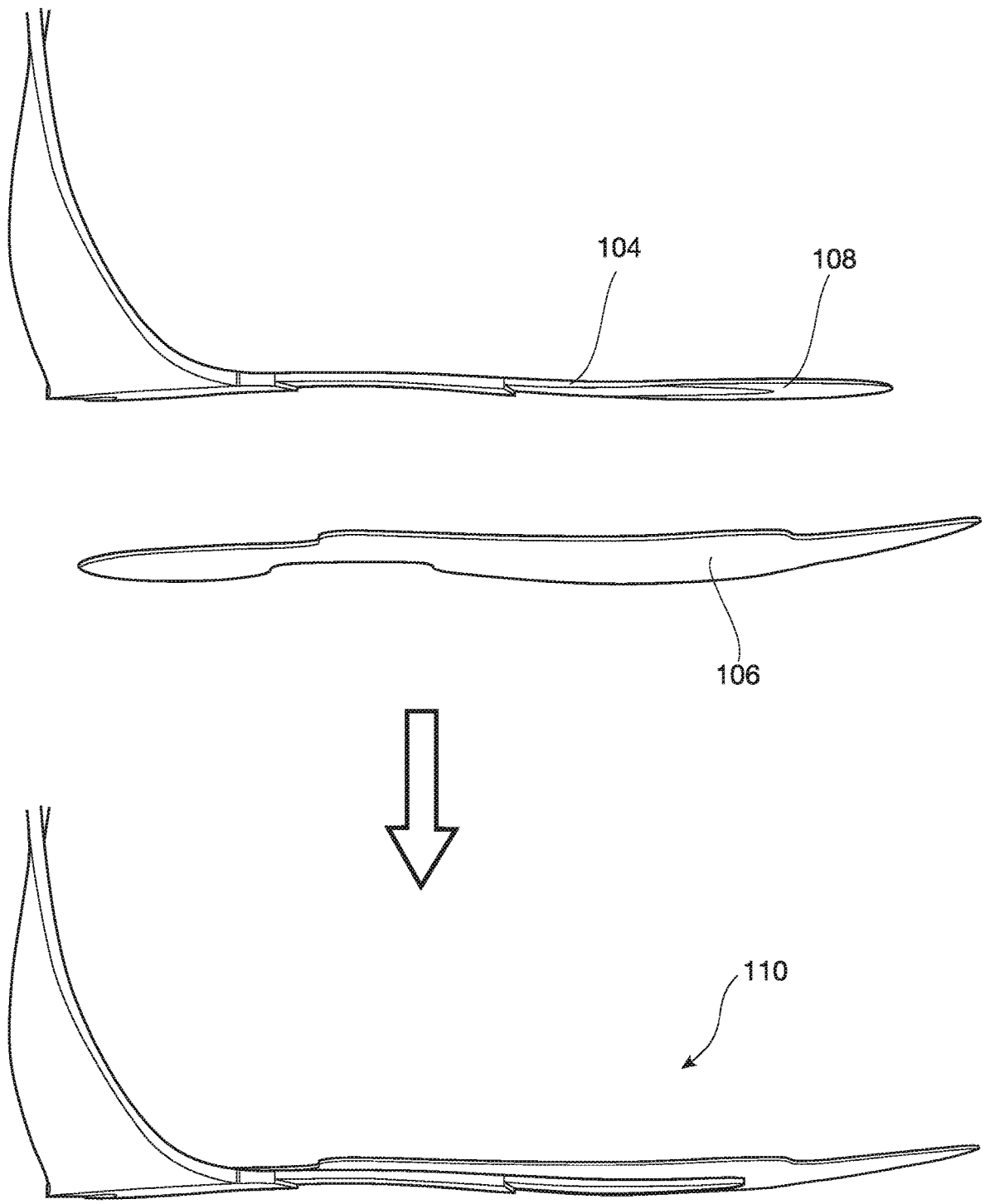
FIG. 1W illustrates the attachment of the formable layer to the carbon fiber foot plate using an adhesive, in accordance with the principles of the present disclosure.

FIG. 1P illustrates a strapping variant to that shown in FIGS. 1G-1I that may be utilized separately from, or in addition to, various features described with respect to FIGS. 1G-1I. As shown in FIG. 1P, the strapping system includes a dorsum strap 150, a calcaneus strap 165, and a spiral strap 164. One primary purpose of the dorsum strap 150 is to keep the heel of the wearer planted inside of the inner boot 142 and prevent the foot of the wearer from moving inside of the inner boot 142. Having slots 146, 147 located on both sides of the inner boot 142 allow for the spiral strap 164 and/or the calcaneus strap 165 to be positioned to address varus and/or valgus deformities. In some implementations, the dorsum slot 147 is positioned at an approximately 45° angle with respect to the bottom of the inner boot 142 and allows for the dorsum strap 150 to provide stability to maintain the calcaneus in place in the inner boot 142. Additional slots may be added in order to change the location of the dorsum strap 150 and/or to add more than one dorsum strap 150 to the underlying strapping system.

FIGS. 1K-1O illustrate various strapping configurations for the AFO 100. FIG. 1L illustrates the spiral strap 164 entering the medial side 141 of the inner boot 142, where it continues underneath the foot of the wearer and attaches to the inner boot 142 on the lateral side 143. By placing the strap 164 between the foot of the wearer and the inner boot 142, the strap is able to properly capture the arch of the foot of the wearer. In some implementations, the strapping configuration may be reversed so that the spiral strap 164 enters the lateral side 143 of the inner boot 142, crosses underneath the foot of the wearer and attaches to the inner boot 142 on the medial side 141. In some implementations, both strapping configurations (i.e., one strap 164 entering the medial side 141 and another strap 164 entering the lateral side 143) may be utilized.

FIG. 1M illustrates another variant to the strapping configuration similar to that shown in FIG. 1L. As illustrated, in addition to the spiral strap 164, a calcaneus strap 165 is shown, where one end of the calcaneus strap 165 is coupled to the spiral strap 164 and the other end of the calcaneus strap 165 is coupled to the inner boot 142 at a position near the calcaneus of the wearer. Similar to that described above with reference to FIG. 1L, the calcaneus strap 165 may enter from the medial side 141 as shown, may enter from the lateral side 143 or may include two calcaneus straps 165 with one entering from the lateral side 143 and one entering from the medial side 141. Additionally, while the spiral strap 164 and the calcaneus strap 165 are illustrated being routed internal to the inner boot 142, it would be readily apparent to one of ordinary skill given the contents of the present disclosure that these straps 164, 165 may be routed external to the inner boot 142 in some implementations.

FIGS. 1N and 1O illustrate the strapping configuration shown in FIG. 1M from a lateral and medial perspective, respectively. Note in FIG. 1O that the spiral strap 164 and the calcaneus strap 165 avoid the ankle of the wearer to reduce abrasion and improve comfort for the wearer. Additionally, FIG. 1N illustrates how the calcaneus strap 165 attaches around the calcaneus of the wearer, while the spiral strap 164 can attach directly opposite of the arch or may be attached closer to the metatarsals to create three solid points of pressure leverage to the foot of the wearer. As but one non-limiting example, when the ankle pronates, the fifth ray shifts upwards and by attaching the spiral strap 164 around the fifth ray, the spiral strap 164 will dynamically pull the fifth ray downwards at the same time the spiral strap 164 pulls the arch of the foot upwards. As shown in FIGS. 1N and 1O, these two straps 164/165 are shown entering the medial side of the foot and attaching to the inner boot 142 on the lateral side of the foot (i.e., configured for a pronated position), though these configurations may be reversed (i.e., enter laterally and connect medially to control a supinated position) or combined in some implementations (i.e., to control both pronated and supinated positions). These and other strapping configurations would be readily apparent to one of ordinary skill given the contents of the present disclosure. Pads may be added in some implementations and may be adjusted and formed to the patient's anatomy in combination with the spiral strap 164 and the calcaneus strap 165. These pads may be manufactured from, for example, foam and/or a thermoplastic and are placed in a strategic area to create the three points of pressure from all planes in the foot to correct the foot from a pronounced position into a neutral position. In other words, the spiral strap 164 and the calcaneus strap 165 in combination with the pads 167 create the most effective loading condition, while minimizing points of abrasion along the foot of the wearer. These and other strapping configurations would be readily apparent to one of ordinary skill given the contents of the present disclosure.

Figures 1, 1X:
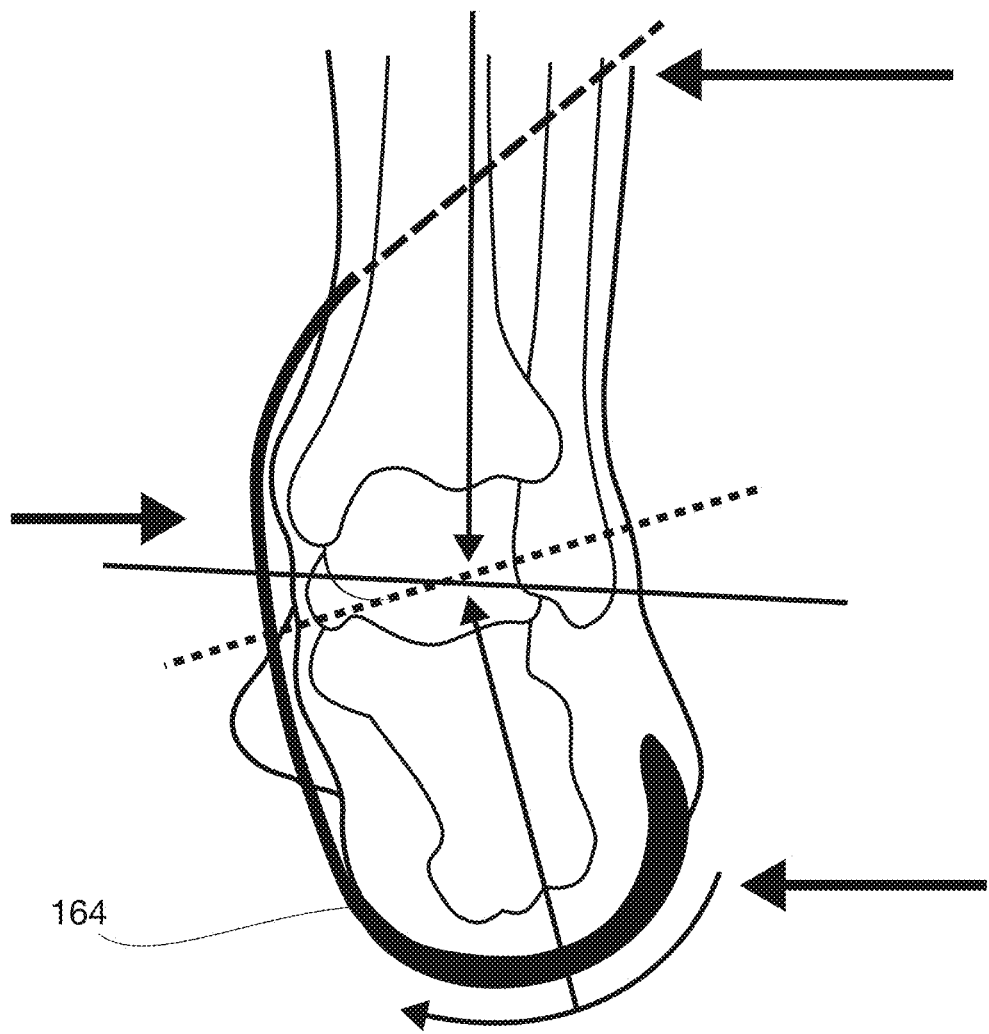
FIG. 1X-1 is a rear elevational view of a wearer's foot illustrating the corrective action of the helical strap and midfoot strap, in accordance with the principles of the present disclosure.
Figures 1, 1X, 2:
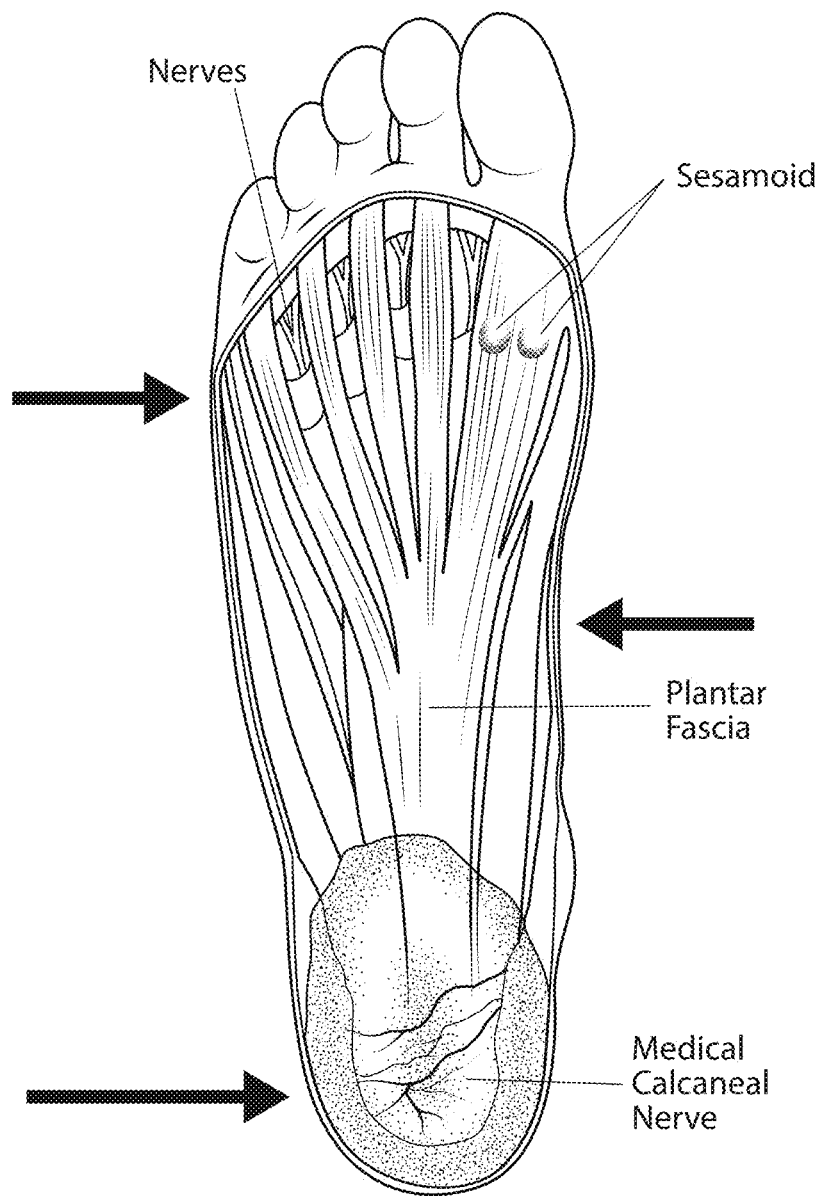
Figures 1, 1X, 2, 3:
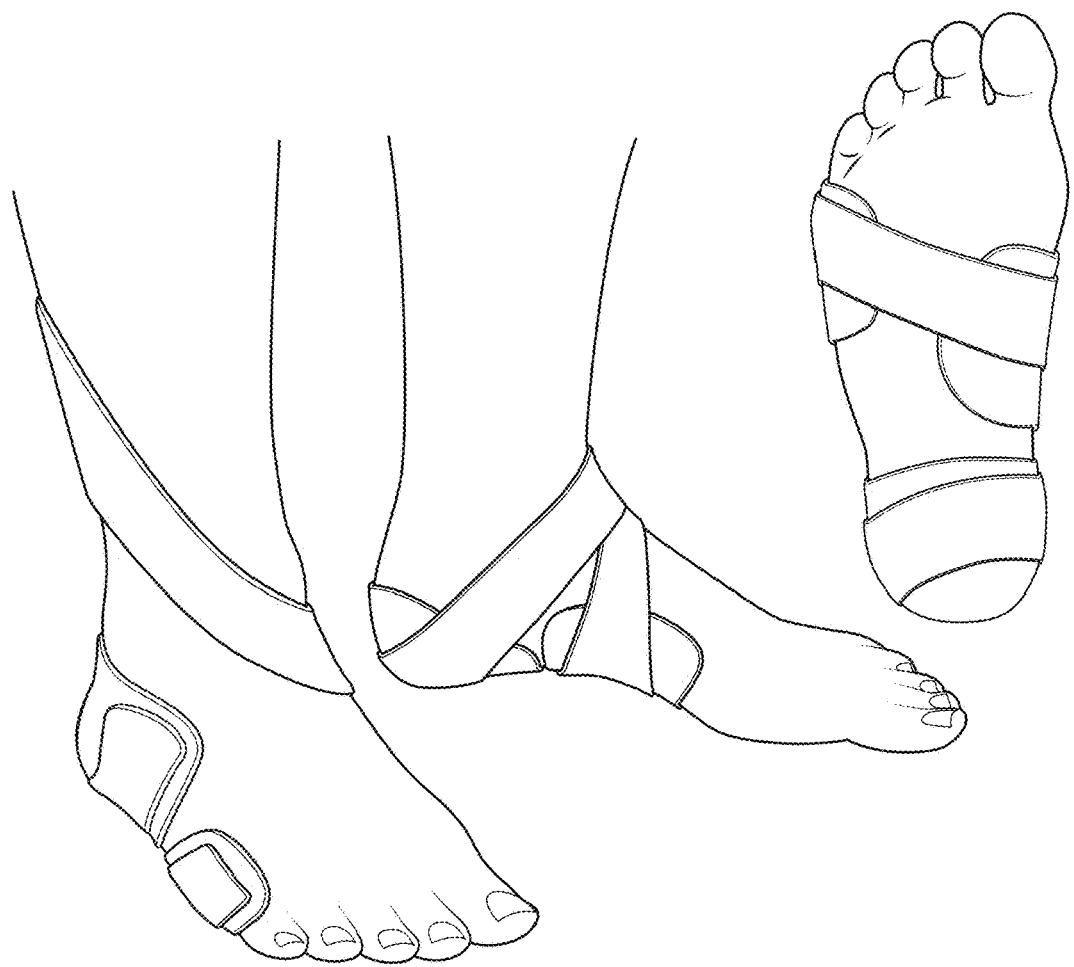
Figures 1, 1X, 2, 3, 4:
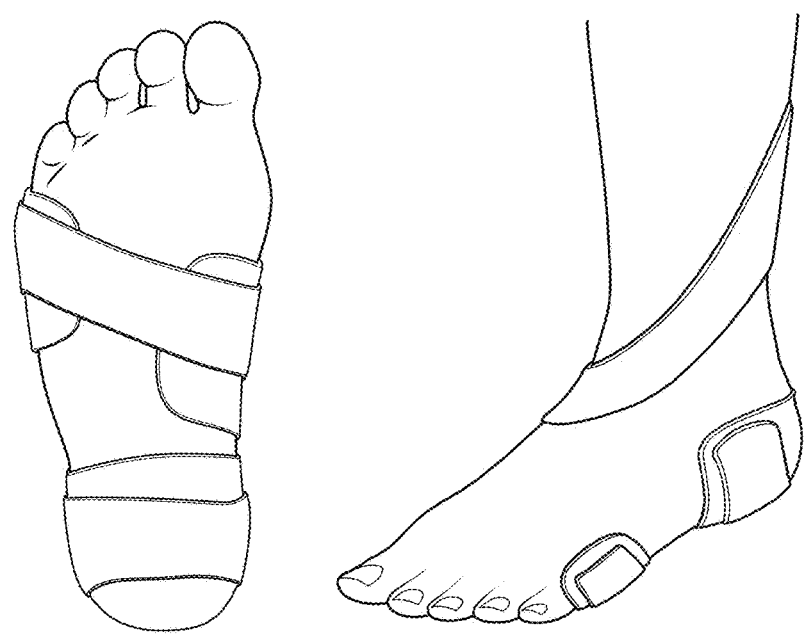
Figures 1, 1X, 2, 3, 4, 5:
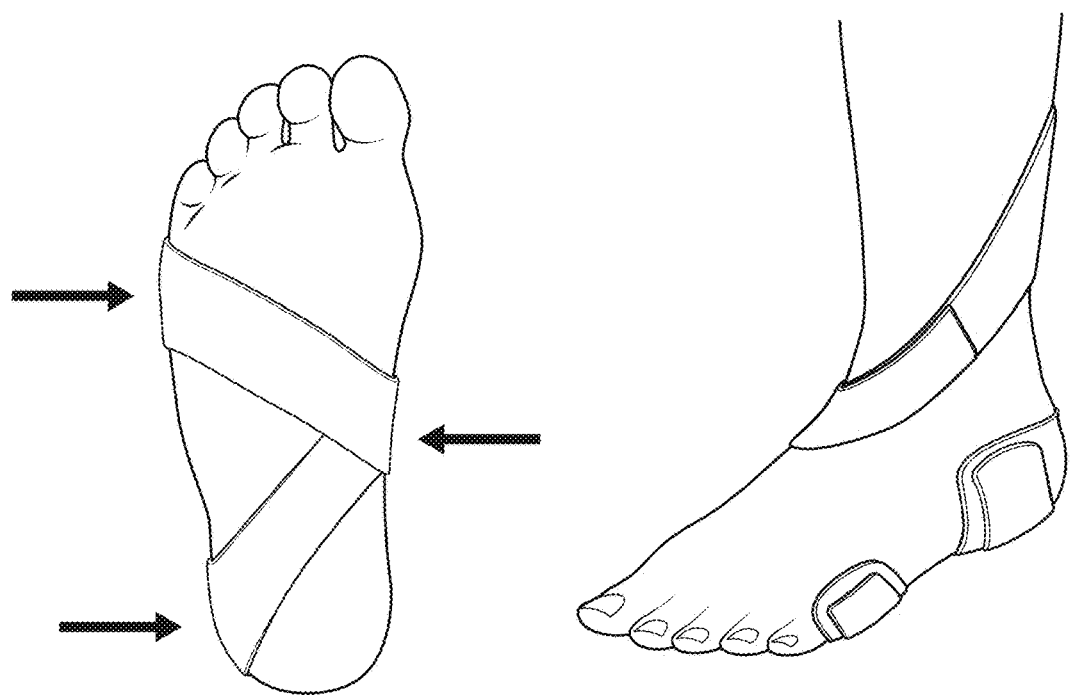
Figures 1, 1X, 2, 3, 4, 5, 6:
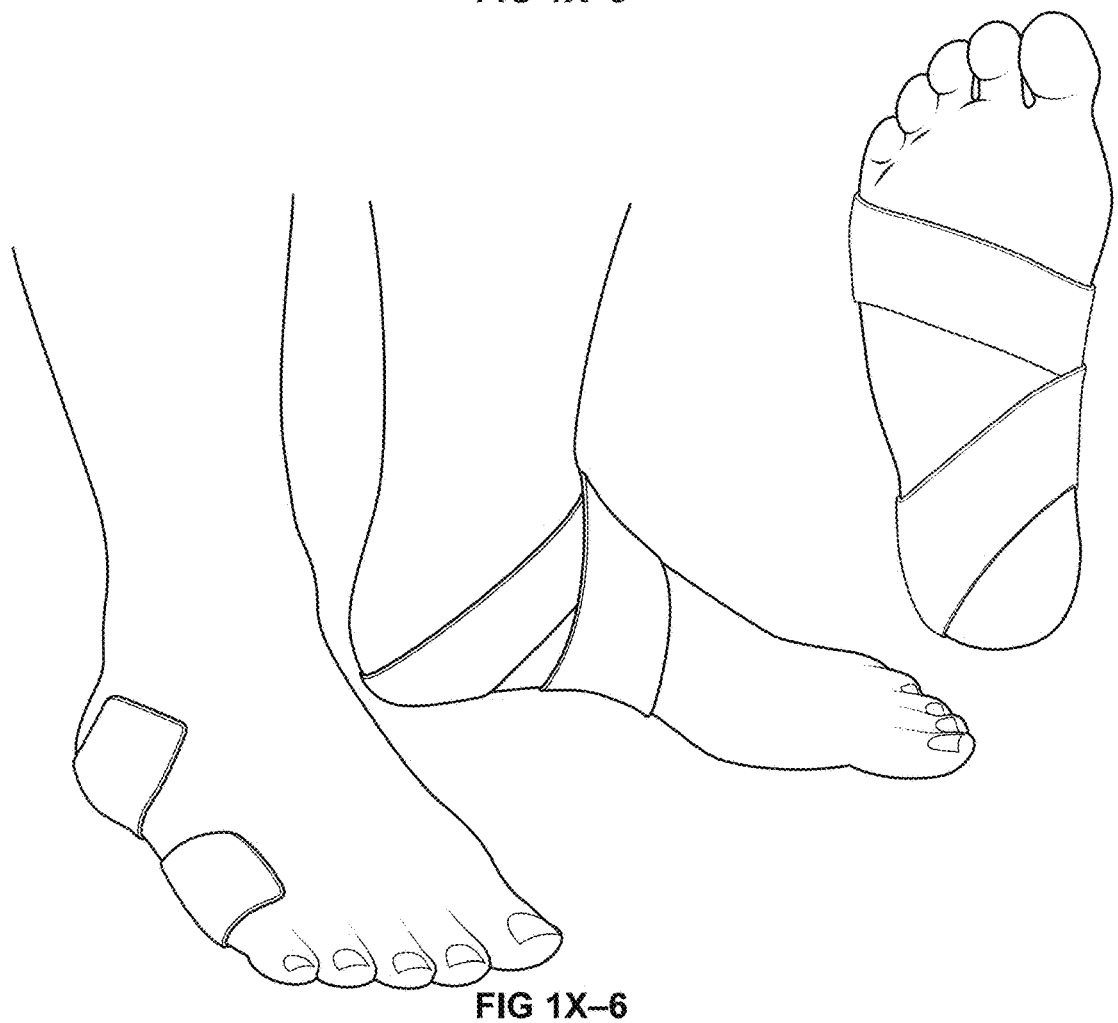

FIG. 1X-1 illustrates a condition in which the foot pronates, and the heel falls out laterally. As illustrated in FIG. 1X-1, by starting the calcaneus portion of the spiral strap 164 on the lateral side around the lateral malleolus of the wearer and traveling underneath the calcaneus of the wearer to come up the medial side of the foot, the spiral strap 164 creates a significant amount (or maximum amount) of leverage to pull the calcaneus into a neutral position. Accordingly, the configuration shown in FIG. 1X-1 creates three points of pressure to correct the pronation shown in FIG. 1X-1. FIG. 1X-2 illustrates the three points of pressure as viewed from the coronal plane of the foot in which the calcaneus will shift out laterally, the mid-foot collapses medially, and the metatarsals on the lateral side of the foot are shifted upwards. By applying the straps 164/165 in such a configuration, a maximum amount of leverage is applied to shift the foot of the wearer into a neutral position.

Referring now to FIGS. 1X-3 and 1X-4, a variant is shown in which pads 167 may be adjusted and formed to the patient's anatomy in combination with the spiral strap 164 and the mid-foot/fore foot strap 165. These pads may be manufactured from, for example, foam and/or a thermoplastic and are placed in a strategic area to create the three points of pressure from all planes in the foot to correct the foot from a pronounced position into a neutral position. In other words, the spiral strap 164 and the mid-foot/fore foot strap 165 in combination with the pads 167 create the most effective loading condition, while minimizing points of abrasion along the foot of the wearer. FIGS. 1X-5 and 1X-6 shown an alternative strapping configuration in which the calcaneus portion of the spiral strap 164 travels straight from the heel of the wearer to the arch of the wearer. These and other strapping configurations would be readily apparent to one of ordinary skill given the contents of the present disclosure.

Figure 2A:
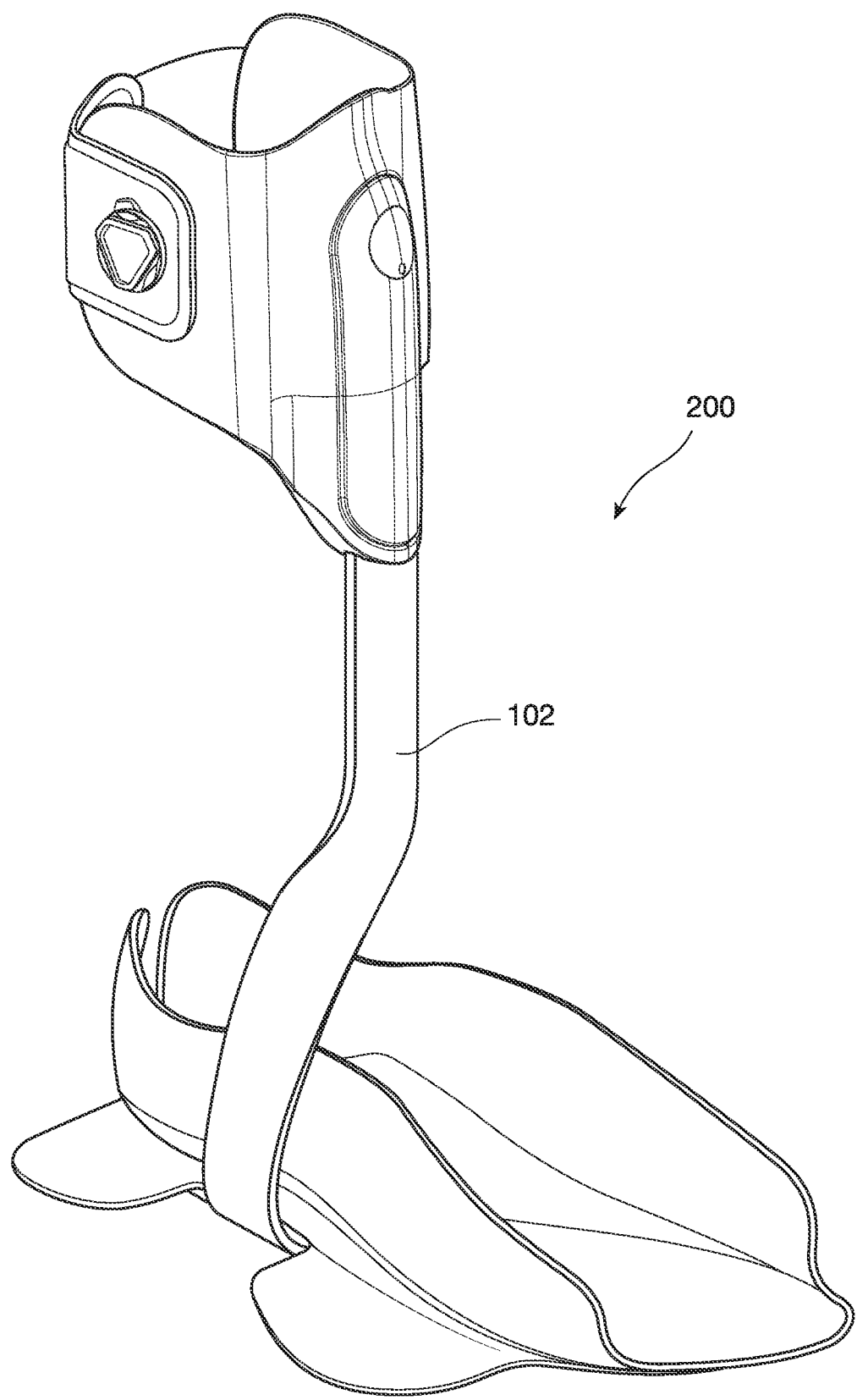
FIG. 2A is a perspective view of an anterior AFO, in accordance with the principles of the present disclosure.
Figure 2B:
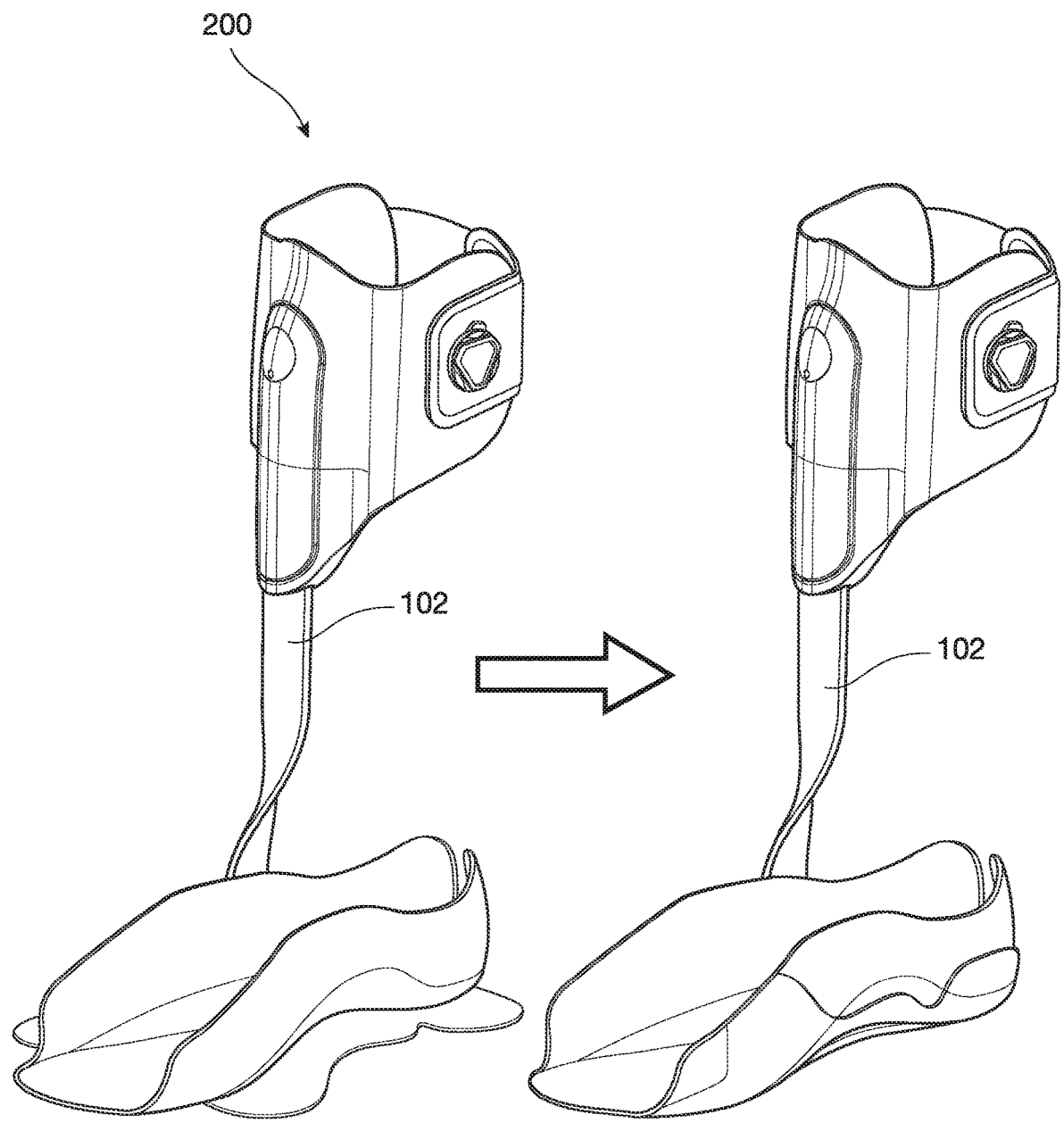
FIG. 2B is a perspective view of the AFO of FIG. 2A illustrating the formability of the footplate around the inner boot, in accordance with the principles of the present disclosure.
Figure 2C:
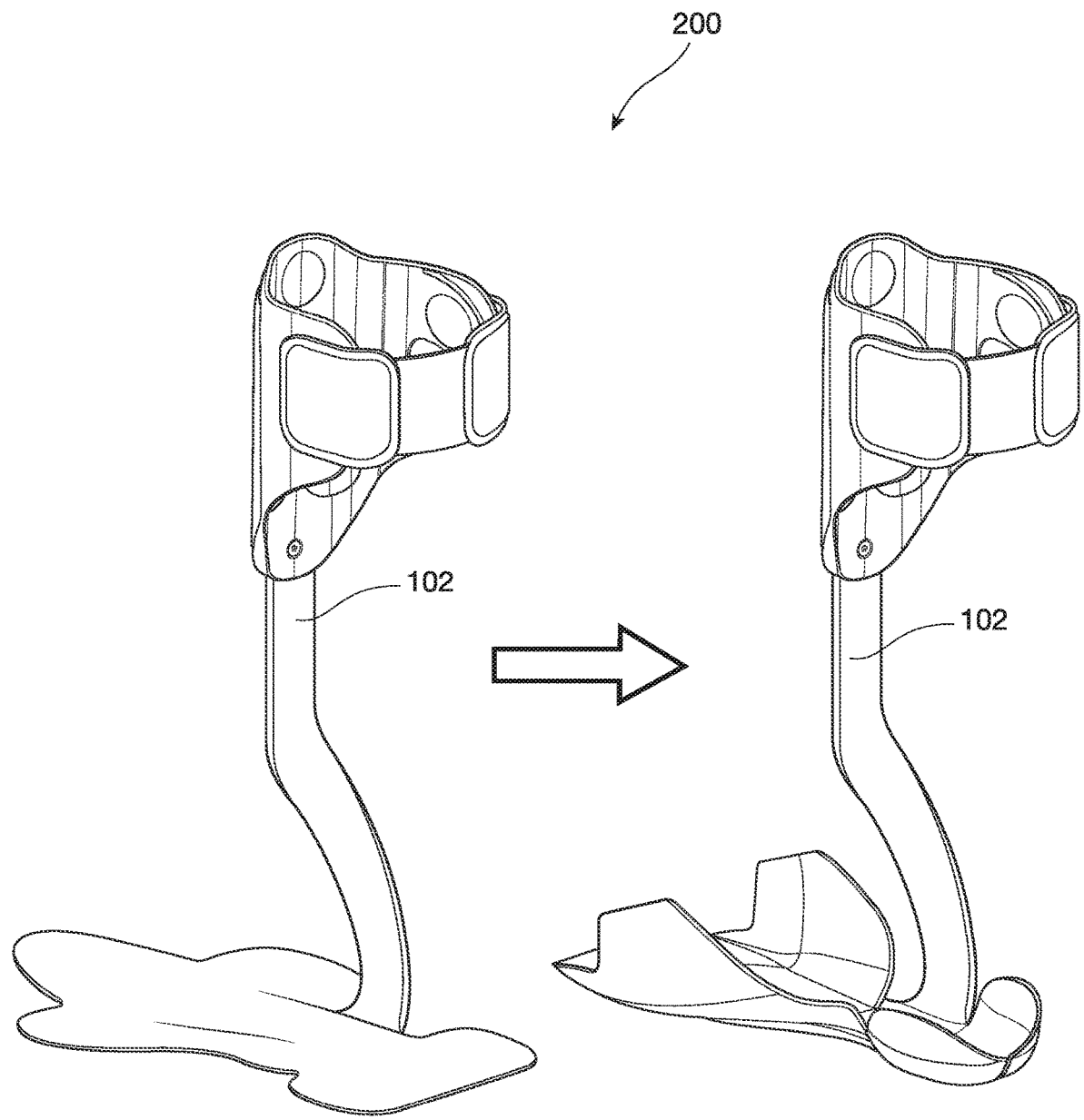
FIG. 2C is a perspective view of the AFO of FIG. 2B with the inner boot removed from view illustrating the formability of the footplate, in accordance with the principles of the present disclosure.
Figure 3A:
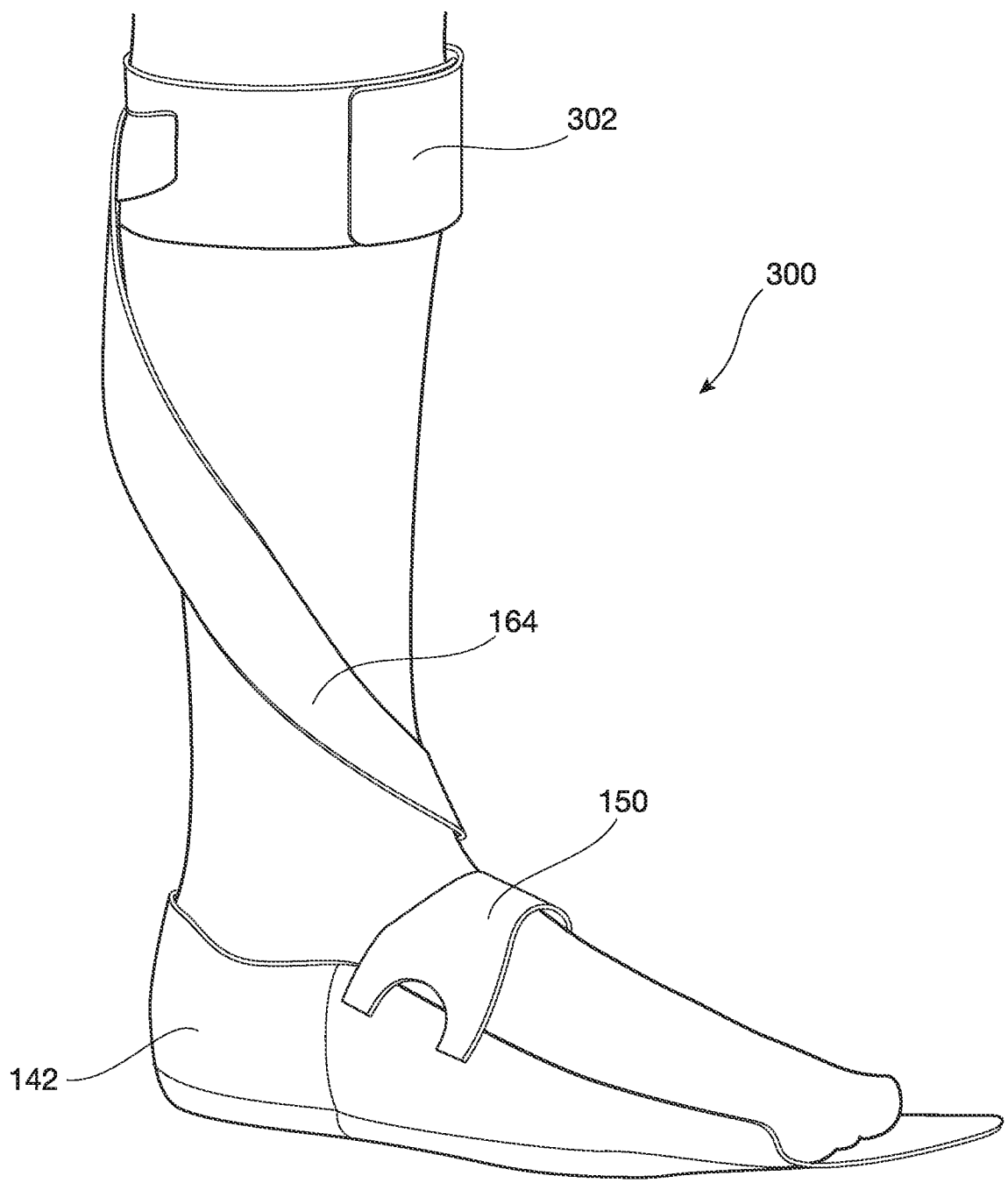
FIG. 3A is an elevational view from the lateral plane illustrating a configuration of the helical strap with calf strap and inner boot, in accordance with the principles of the present disclosure.
Figure 3B:
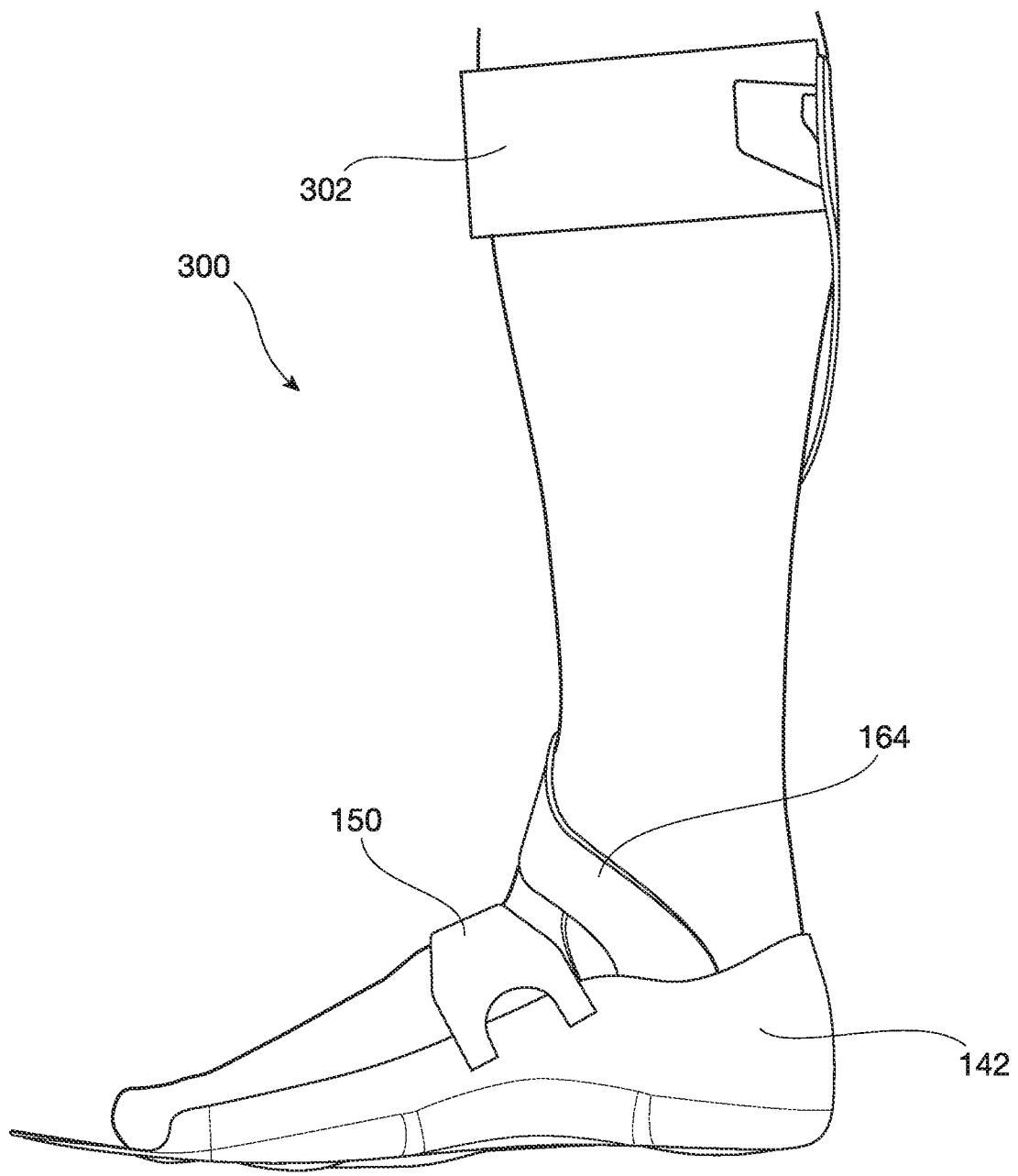
FIG. 3B is an elevational view from the medial plane illustrating the configuration of FIG. 3A, in accordance with the principles of the present disclosure.
Figure 3C:
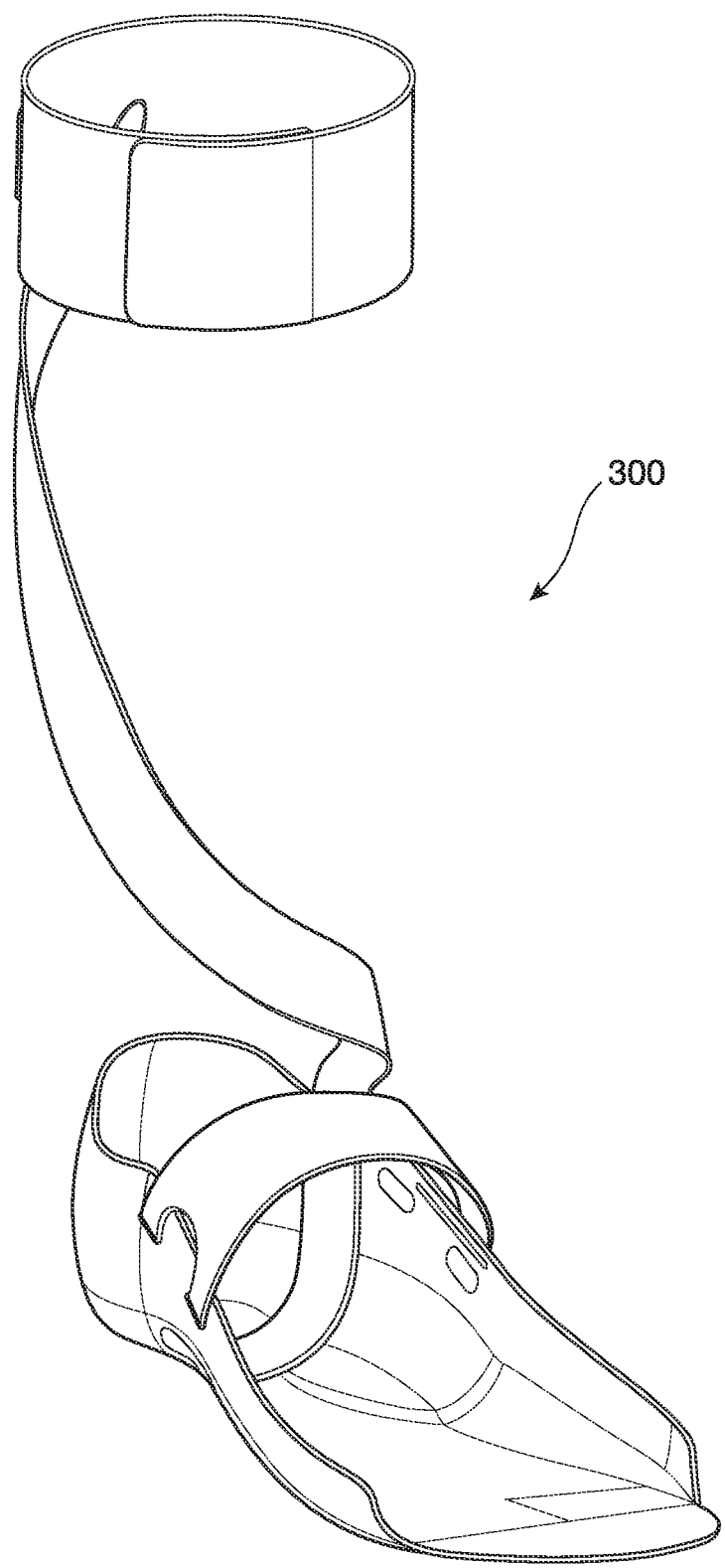
FIG. 3C is a front perspective view of the configuration shown in FIG. 3A, in accordance with the principles of the present disclosure.
Figure 3D:
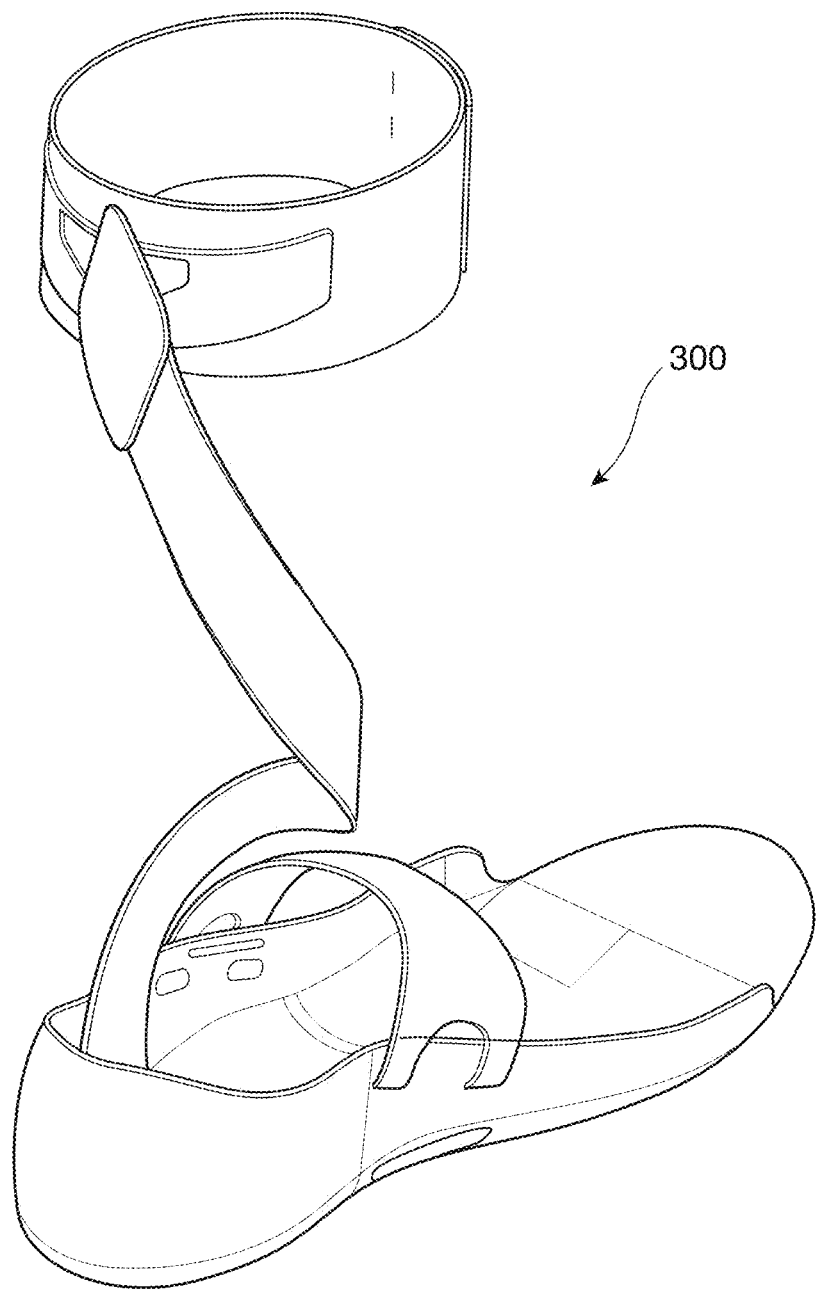
FIG. 3D is a rear perspective view of the configuration shown in FIG. 3A, in accordance with the principles of the present disclosure.
Figure 3E:
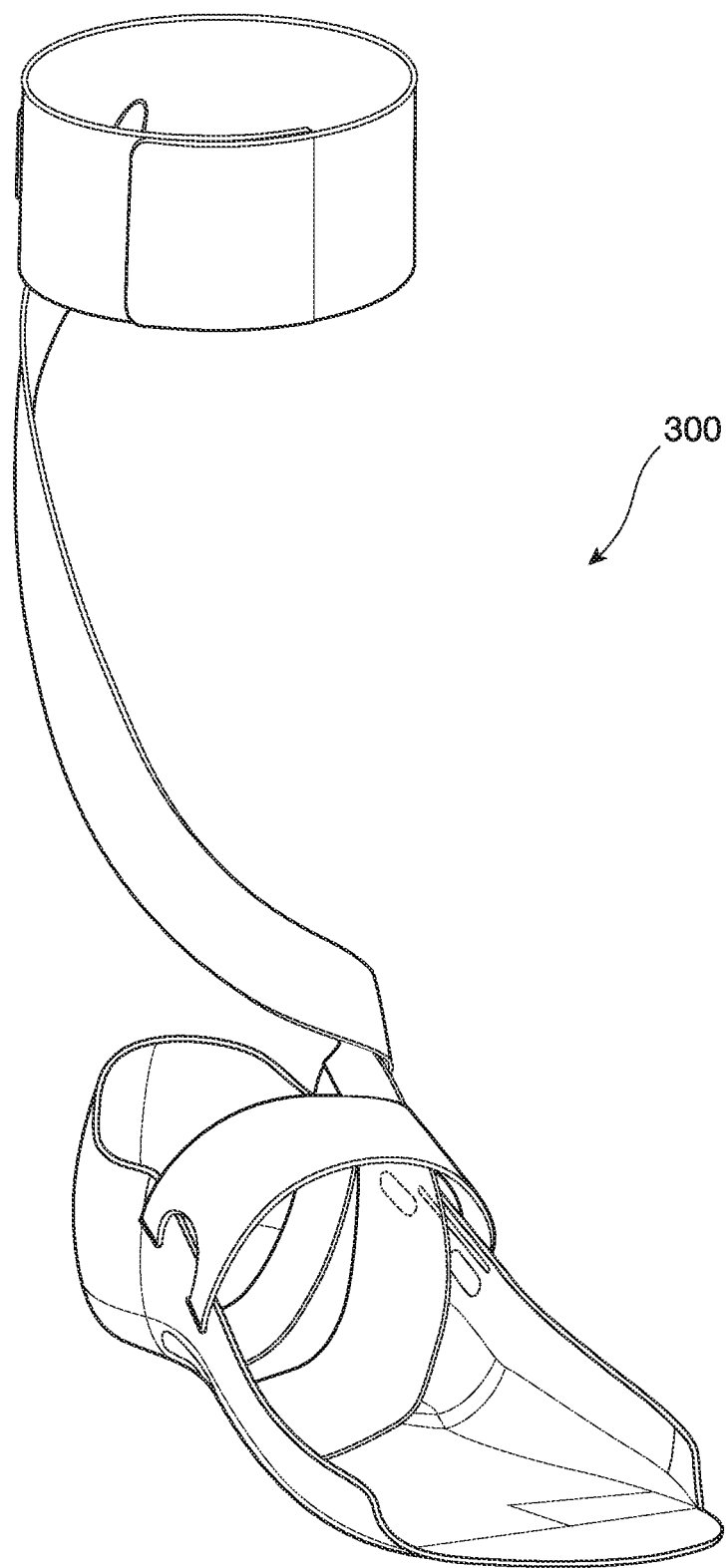
FIG. 3E is a front perspective view of the configuration shown in FIG. 3A with midfoot strap, in accordance with the principles of the present disclosure.
Figure 3F:
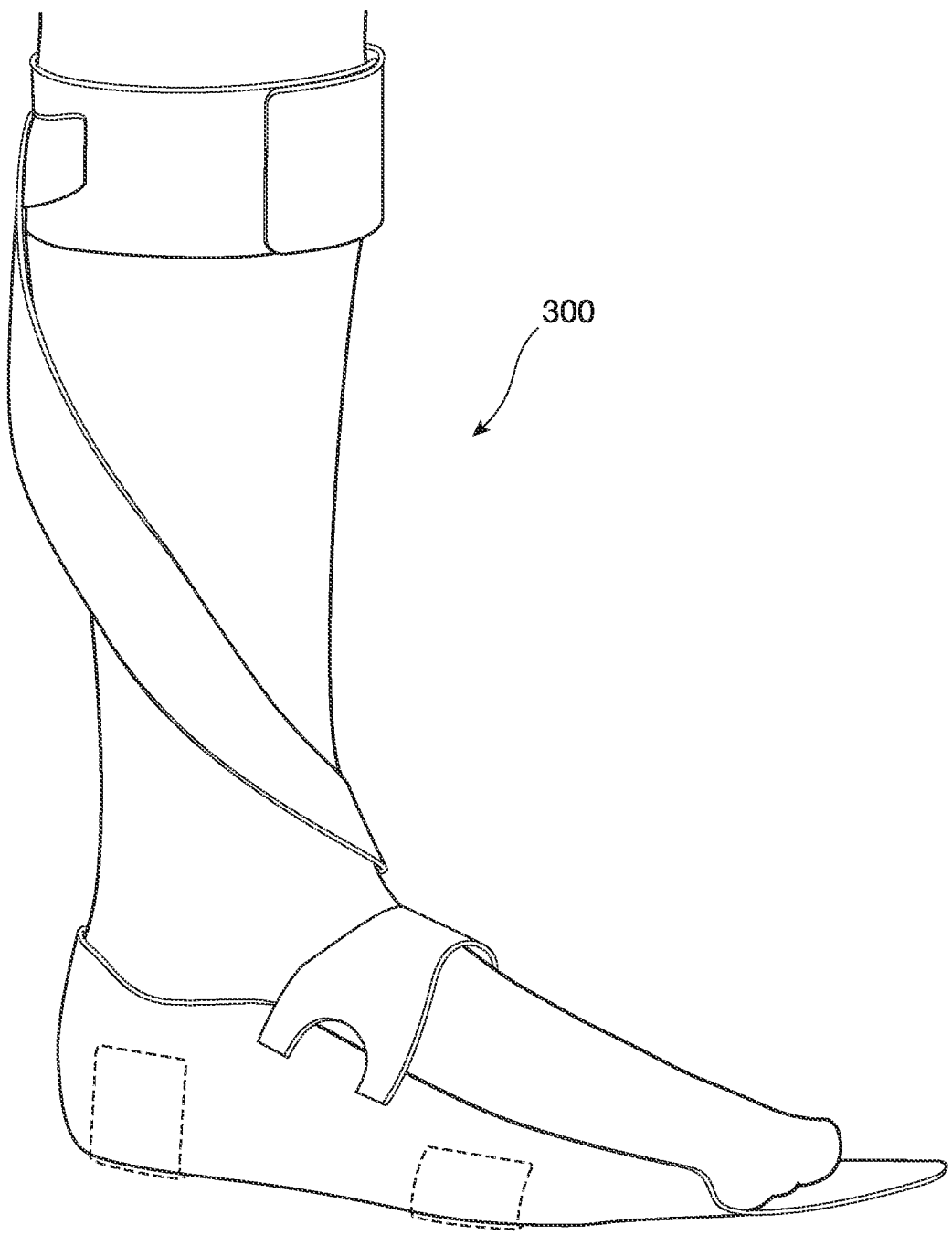
FIG. 3F is an elevational view from the lateral plane illustrating placement of the helical strap and midfoot strap of FIG. 3E, in accordance with the principles of the present disclosure.
Figure 3G:
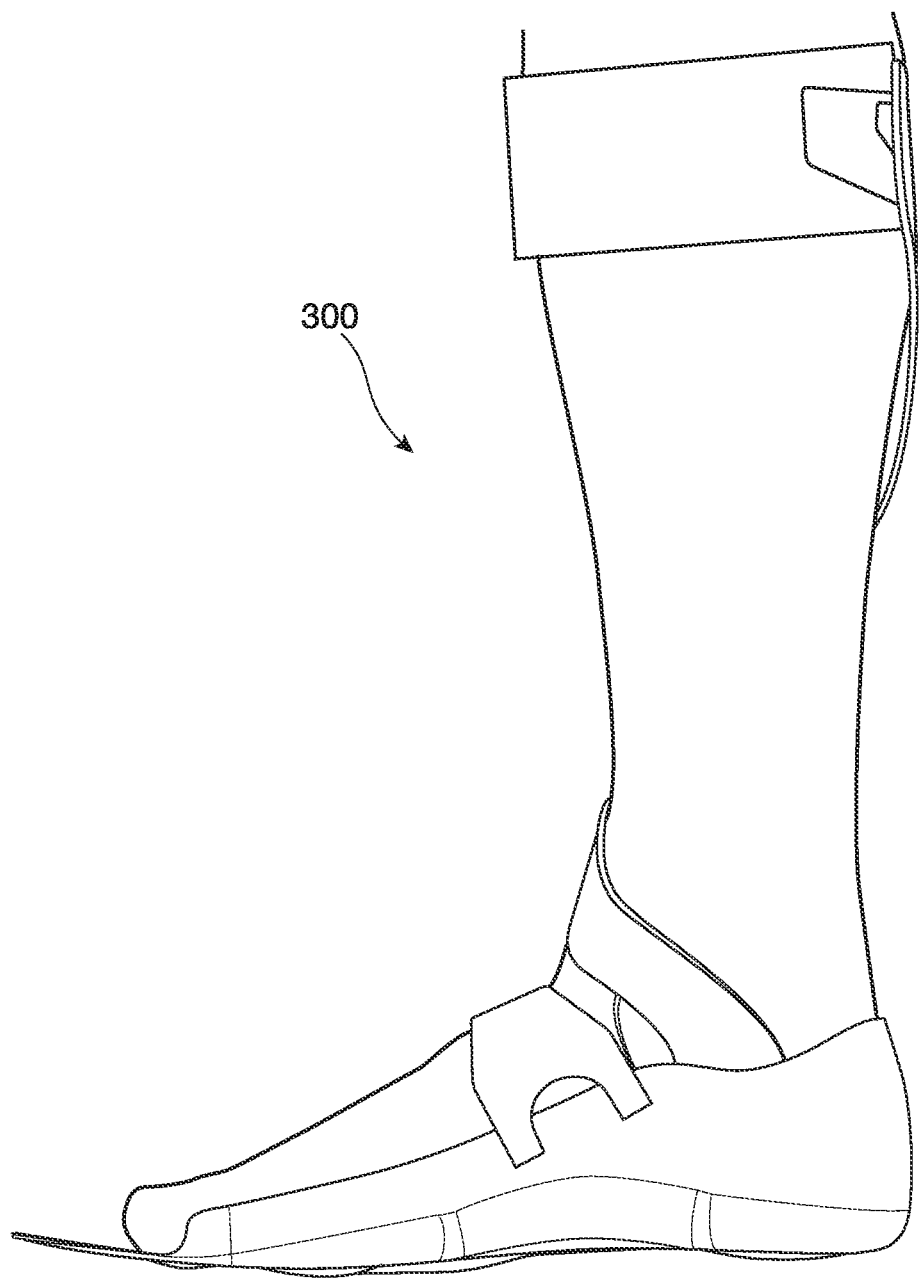
FIG. 3G is an elevational view from the medial plane illustrating placement of the helical strap and midfoot strap of FIG. 3E, in accordance with the principles of the present disclosure.
Figure 3H:
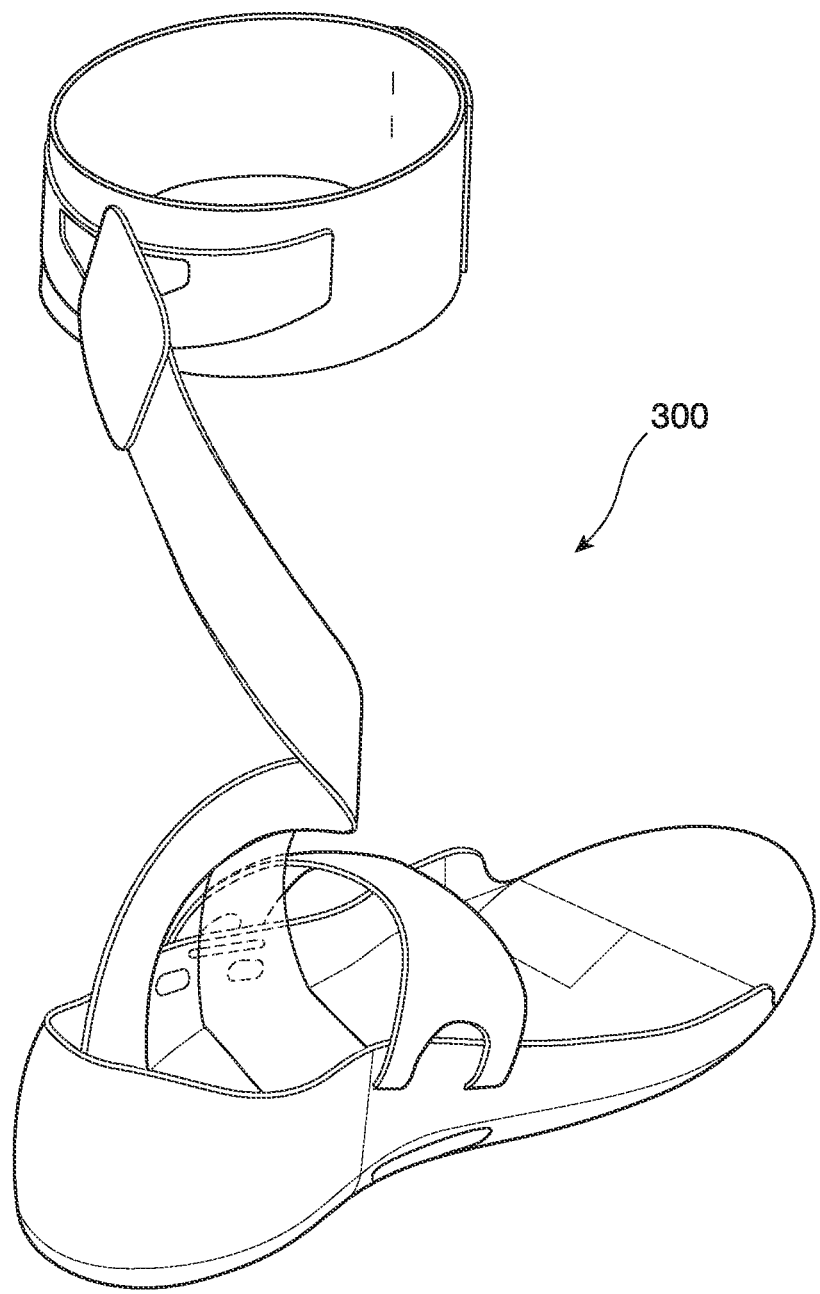
FIG. 3H is a rear perspective view of the configuration shown in FIG. 3E, in accordance with the principles of the present disclosure.
Figure 3I:
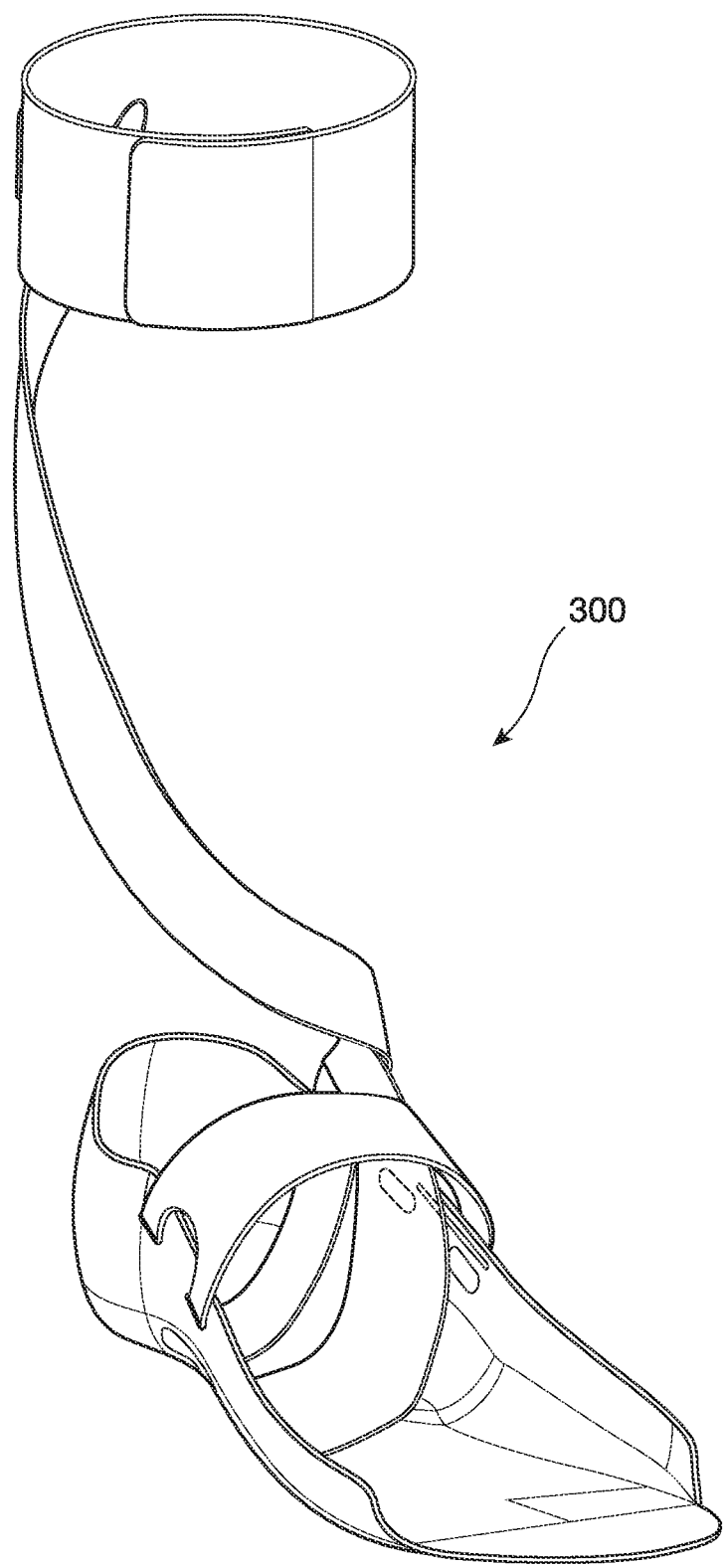
FIG. 3I is a front perspective view of the configuration shown in FIG. 3E, in accordance with the principles of the present disclosure.

FIGS. 2A-2C illustrate a variant where the AFO 200 is now a so-called anterior AFO in which the strut 102 spirals up in front of the lateral malleolus of the wearer and up the front of the tibia. Various features as were described above with respect to FIGS. 1A-1X-6 may be utilized in combination with the anterior AFO 200 shown in FIGS. 2A-2C. FIGS. 3A-3I illustrates a variant support structure 300 in which the inner boot 142 may be utilized in combination with the spiral strap 164 and a calf strap 302 that may be utilized separate from an AFO 100, 200. In the configuration shown, the support structure 300 enables the wearer to have less supportive bracing as shown in FIGS. 1A-2C at home without shoes and provides sagittal and frontal plane support without necessitating the other portions of the AFO shown in FIGS. 1A-2C. The embodiments depicted in FIGS. 3A-3I provide many of the advantages as those described with reference to FIGS. 1A-2C and can be used with or without a carbon fiber frame. These and other variants would be readily apparent to one of ordinary skill given the contents of the present disclosure.

Exemplary Customization Processes—

Figure 4A:
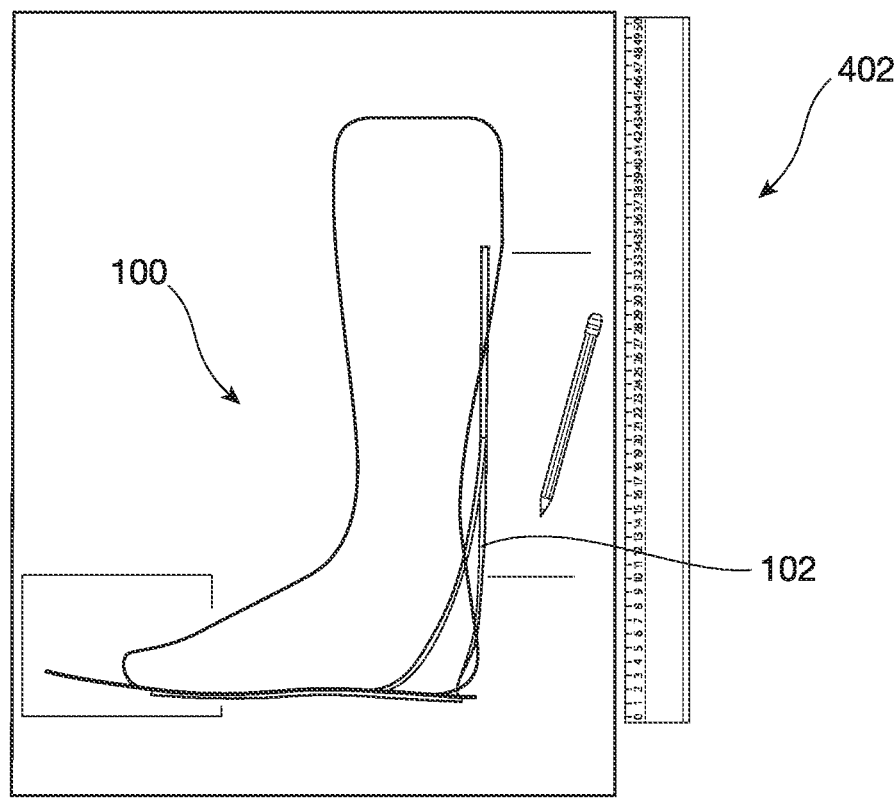
FIG. 4A is an elevational view of an exemplary step for fabricating the AFO of FIG. 1A to the anatomy of a patient, in accordance with the principles of the present disclosure.
Figure 4B:
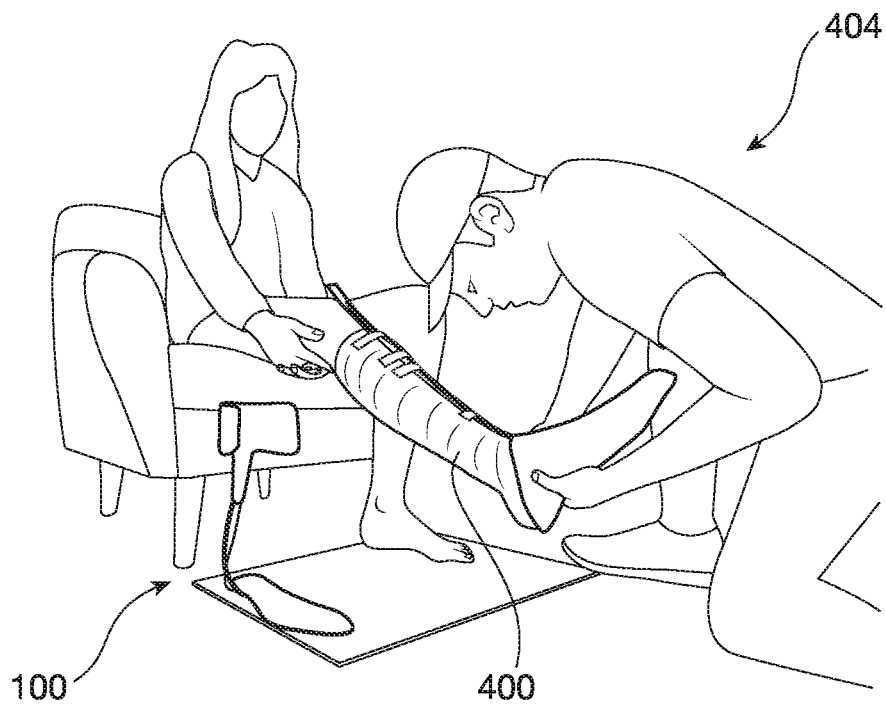
FIG. 4B is a perspective view of an exemplary step for fabricating the AFO of FIG. 1A to the anatomy of a patient, in accordance with the principles of the present disclosure.
Figure 4C:
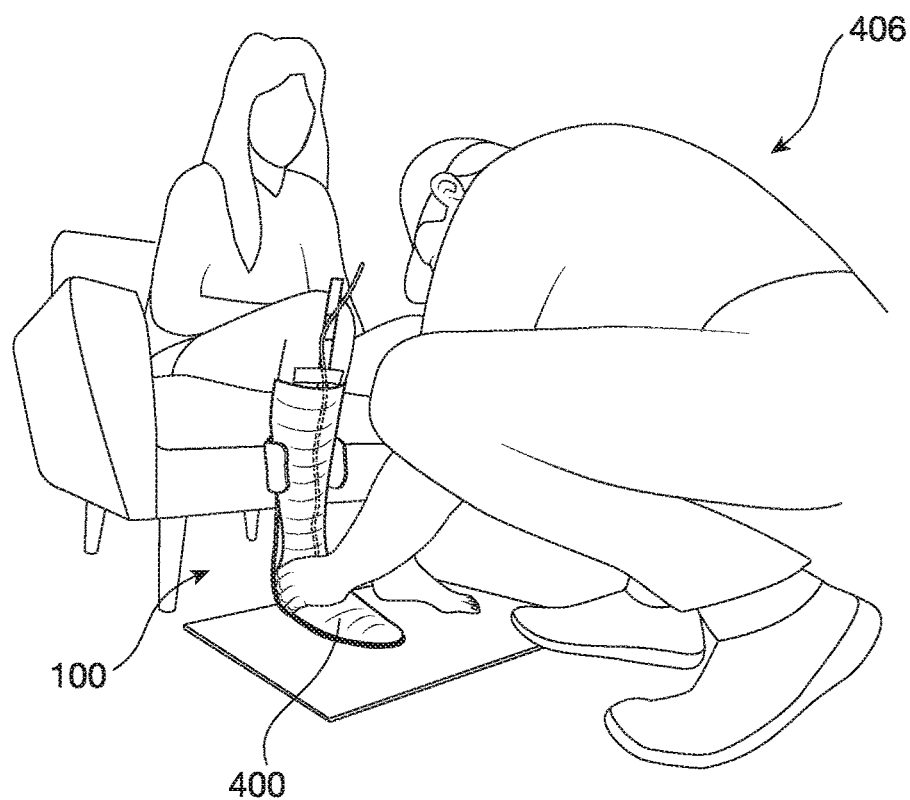
FIG. 4C is a perspective view of an exemplary step for fabricating the AFO of FIG. 1A to the anatomy of a patient, in accordance with the principles of the present disclosure.
Figure 4D:
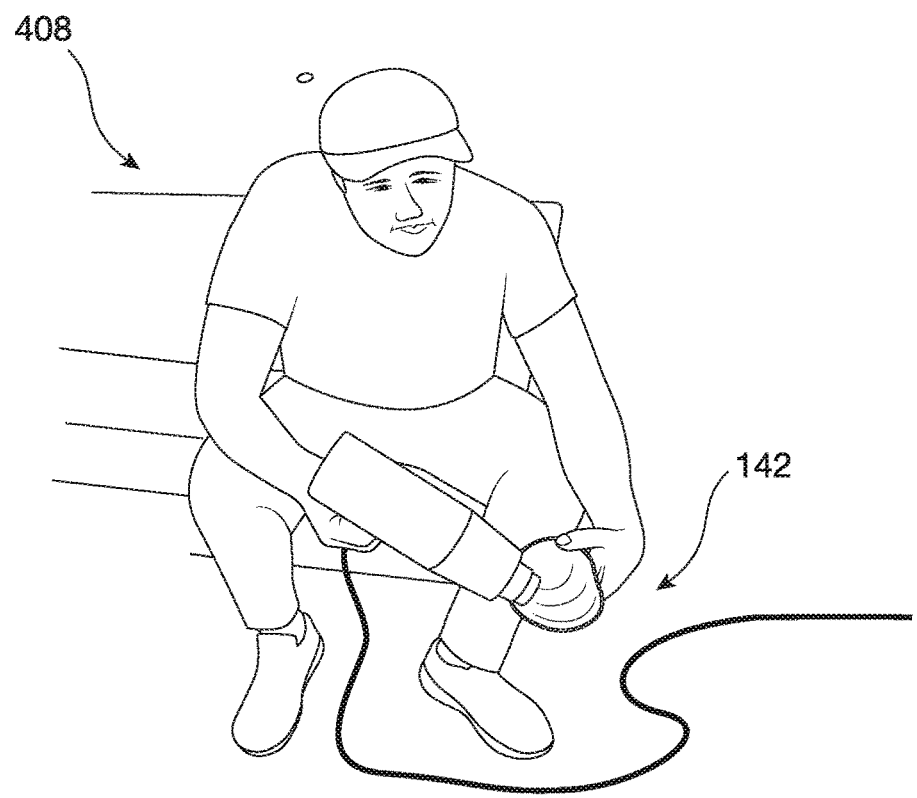
FIG. 4D is a perspective view of an exemplary step for fabricating the AFO of FIG. 1A to the anatomy of a patient, in accordance with the principles of the present disclosure.
Figure 4E:
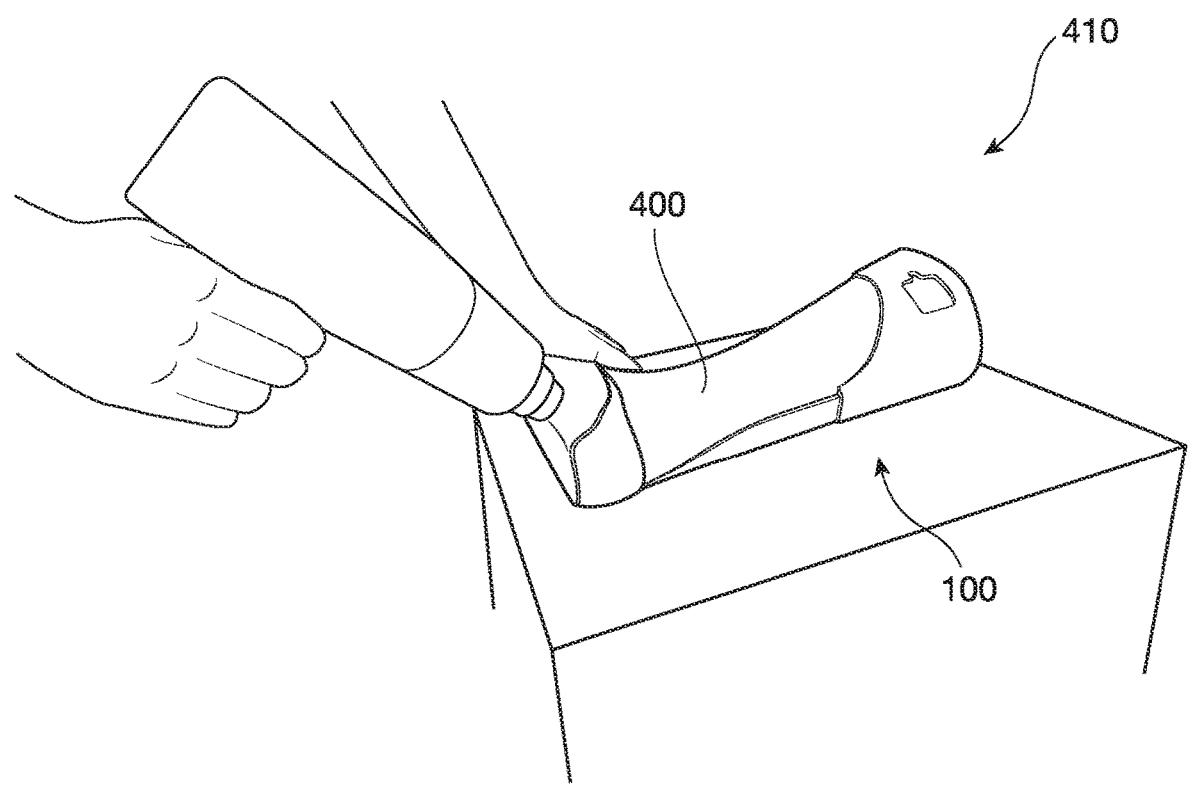
FIG. 4E is a perspective view of an exemplary step for fabricating the AFO of FIG. 1A to the anatomy of a patient, in accordance with the principles of the present disclosure.
Figure 4F:
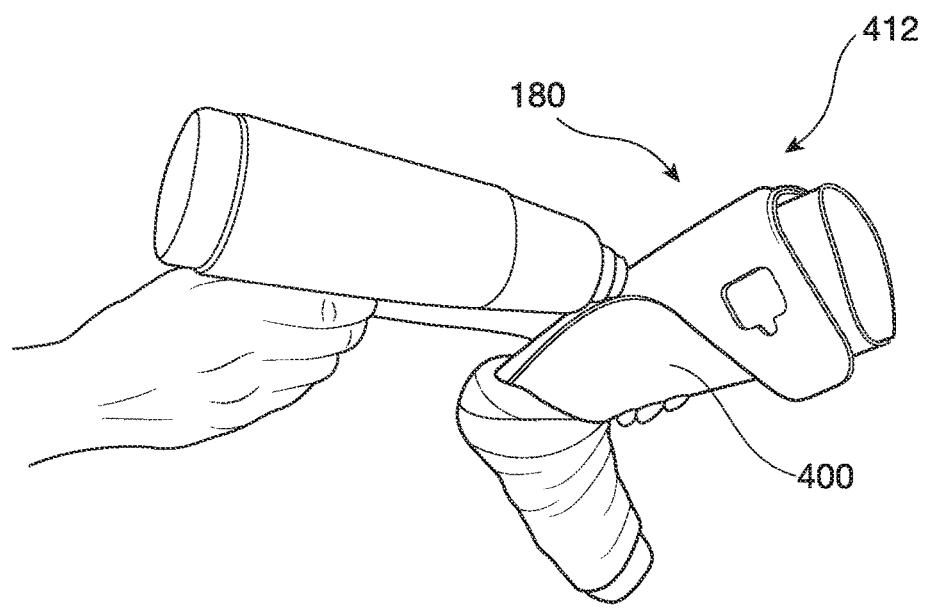
FIG. 4F is a perspective view of an exemplary step for fabricating the AFO of FIG. 1A to the anatomy of a patient, in accordance with the principles of the present disclosure.
Figure 4G:
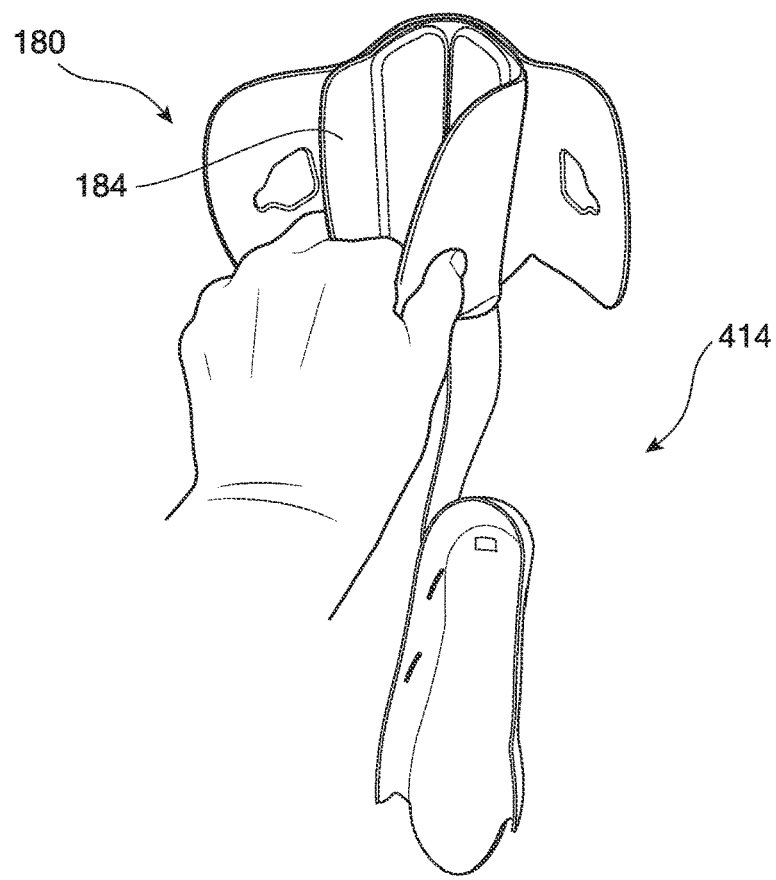
FIG. 4G is a perspective view of an exemplary step for fabricating the AFO of FIG. 1A to the anatomy of a patient, in accordance with the principles of the present disclosure.
Figure 4H:
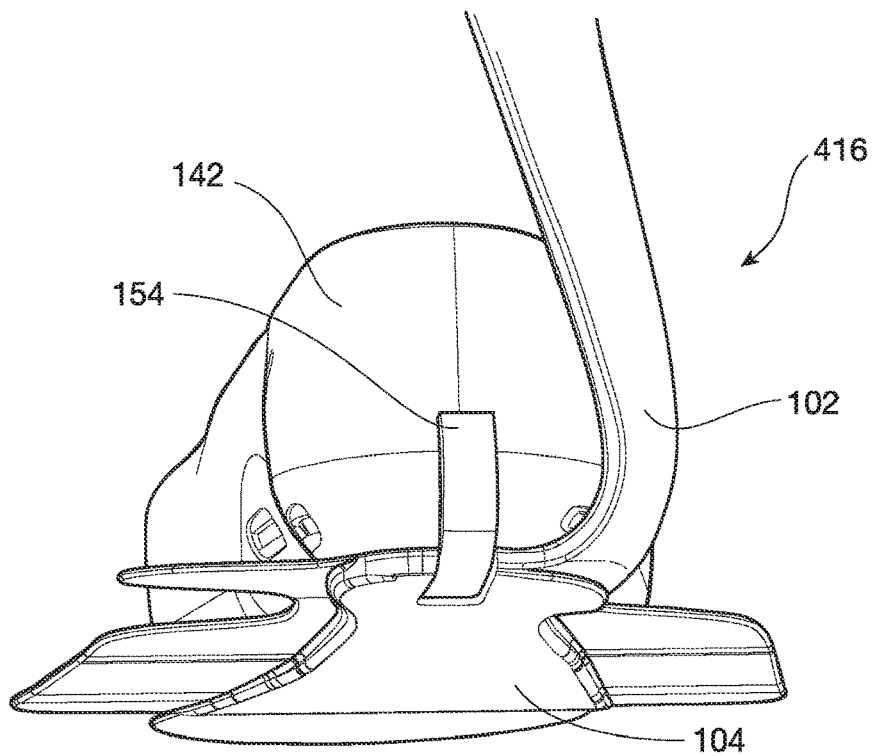
FIG. 4H is a perspective view of an exemplary step for fabricating the AFO of FIG. 1A to the anatomy of a patient, in accordance with the principles of the present disclosure.
Figure 4I:
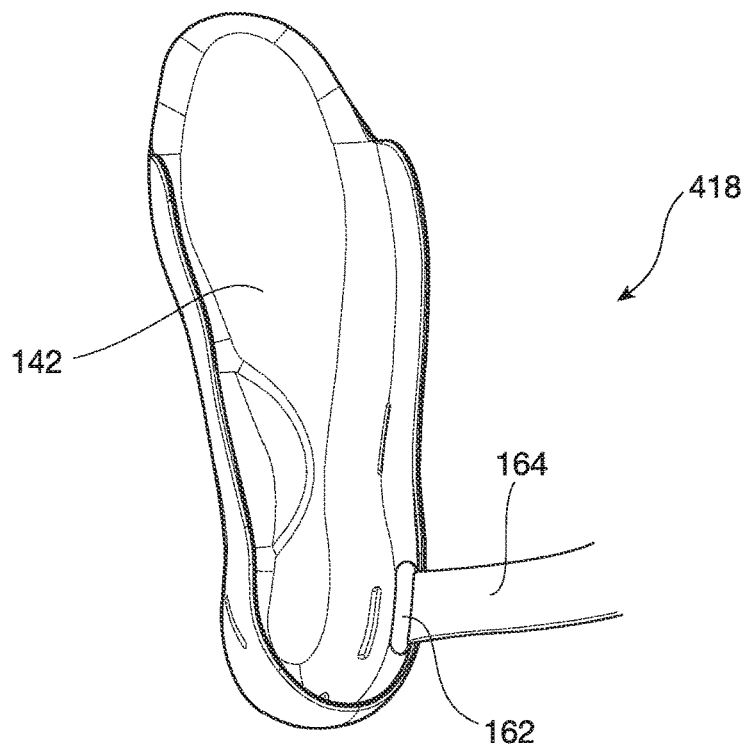
FIG. 4I is a perspective view of an exemplary step for fabricating the AFO of FIG. 1A to the anatomy of a patient, in accordance with the principles of the present disclosure.
Figure 4J:
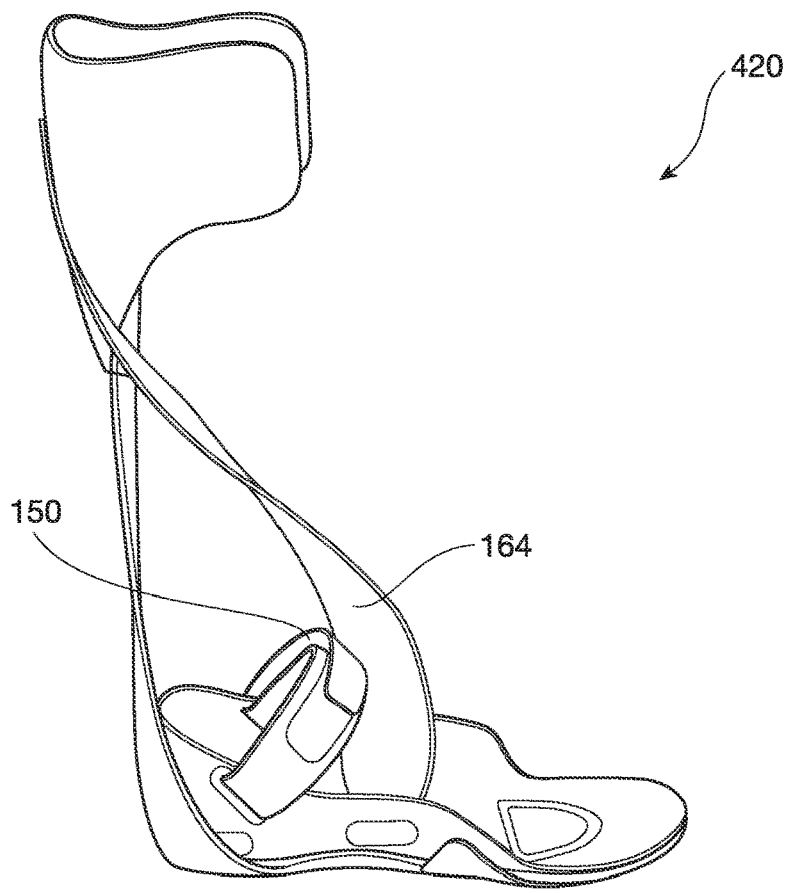
FIG. 4J is a perspective view of an exemplary step for fabricating the AFO of FIG. 1A to the anatomy of a patient, in accordance with the principles of the present disclosure.
Figure 4K:
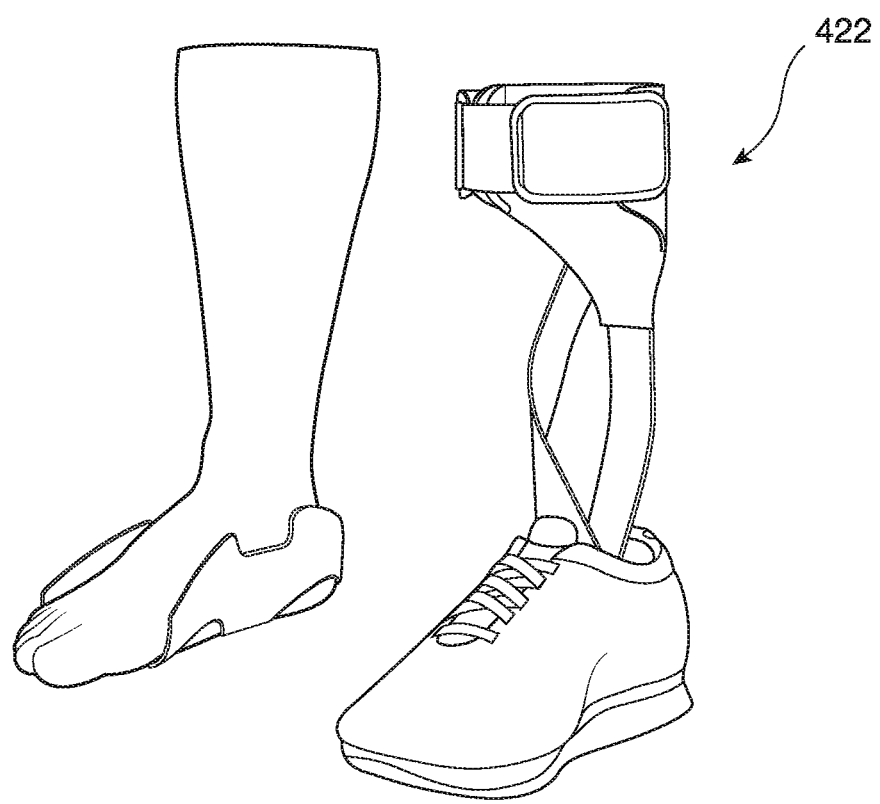
FIG. 4K is a perspective view of a properly sized AFO of FIG. 1A, in accordance with the principles of the present disclosure.
Figure 4L:
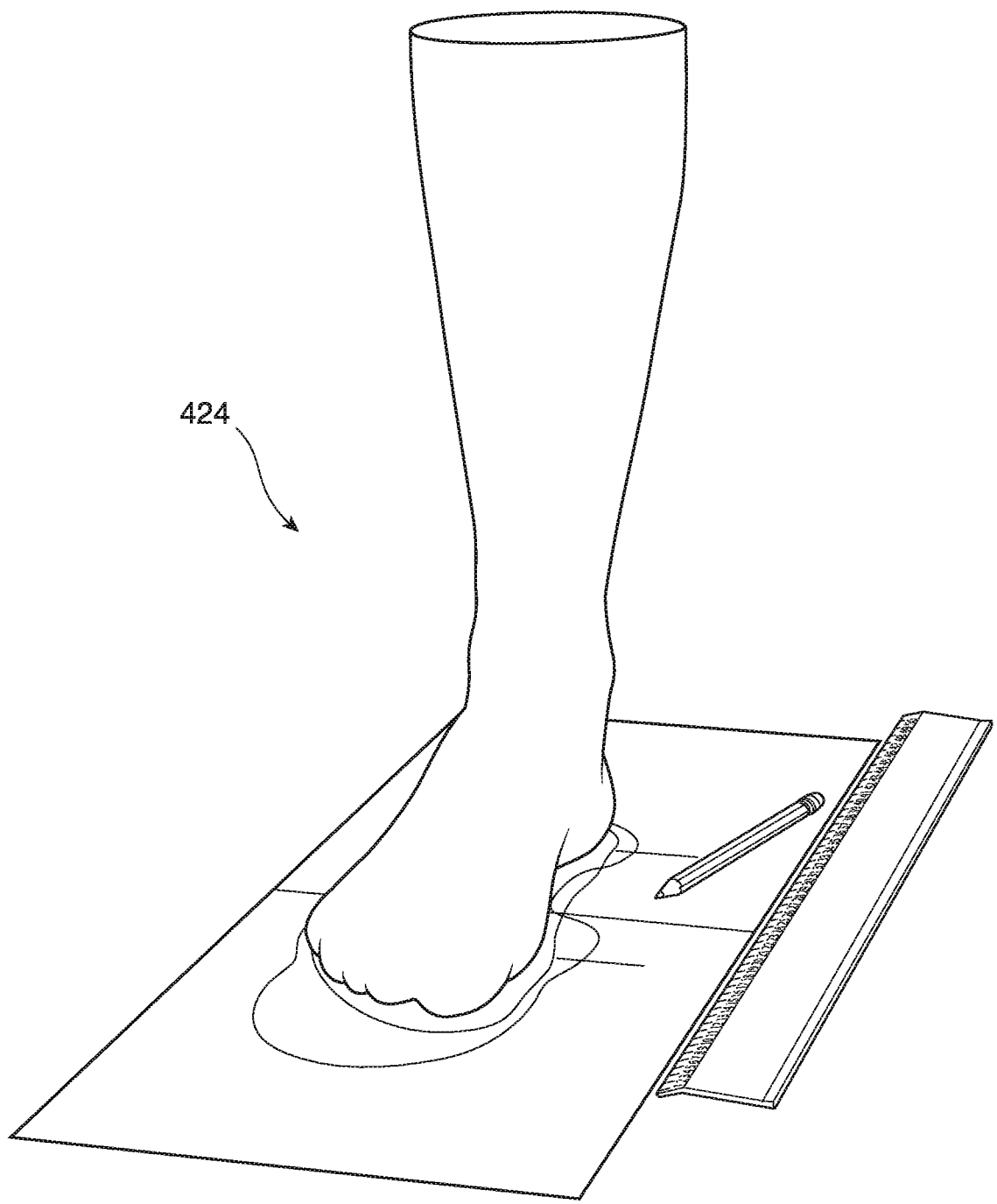
FIG. 4L is a perspective view of an exemplary step for fabricating the AFO of FIG. 1A to the anatomy of a patient, in accordance with the principles of the present disclosure.
Figure 4M:
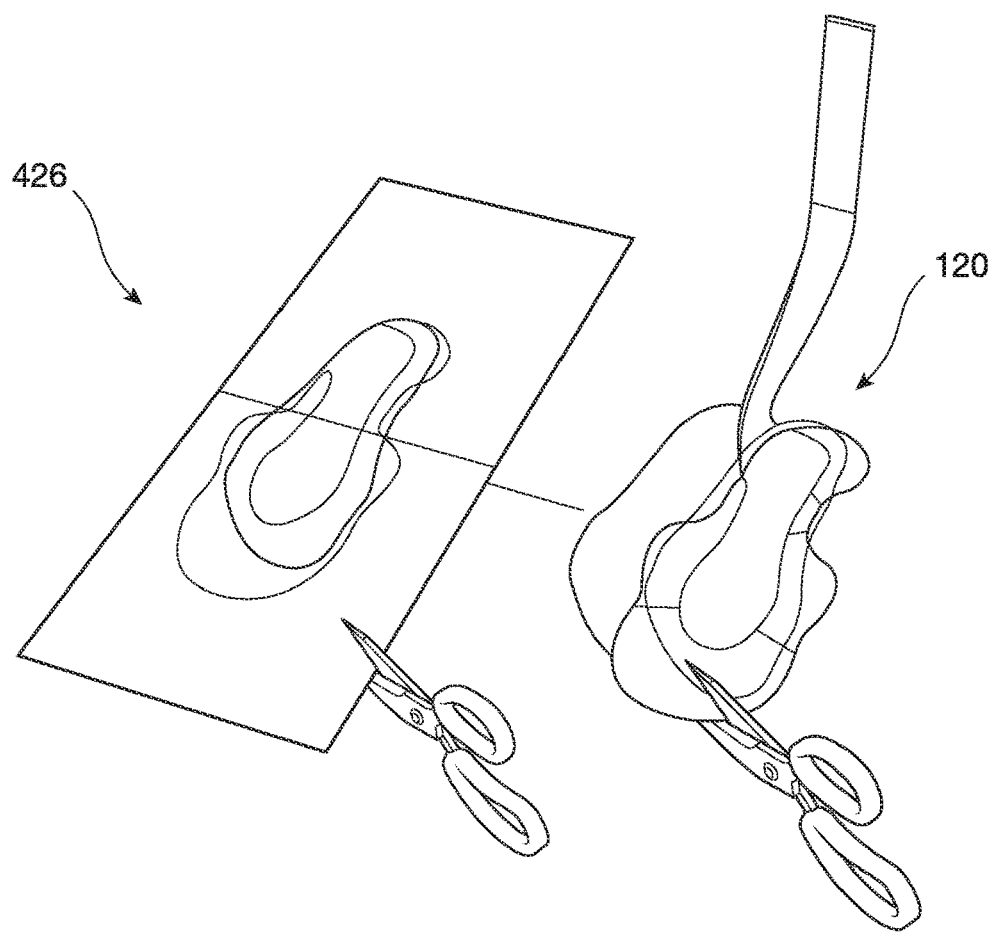
FIG. 4M is a perspective view of an exemplary step for fabricating the AFO of FIG. 1A to the anatomy of a patient, in accordance with the principles of the present disclosure.
Figure 4N:
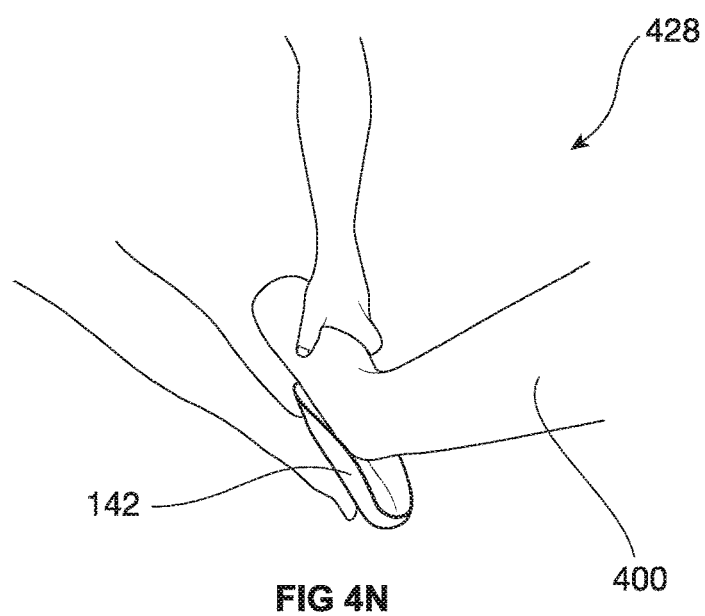
FIG. 4N is a perspective view of an exemplary step for fabricating the AFO of FIG. 1A to the anatomy of a patient, in accordance with the principles of the present disclosure.
Figure 4O:
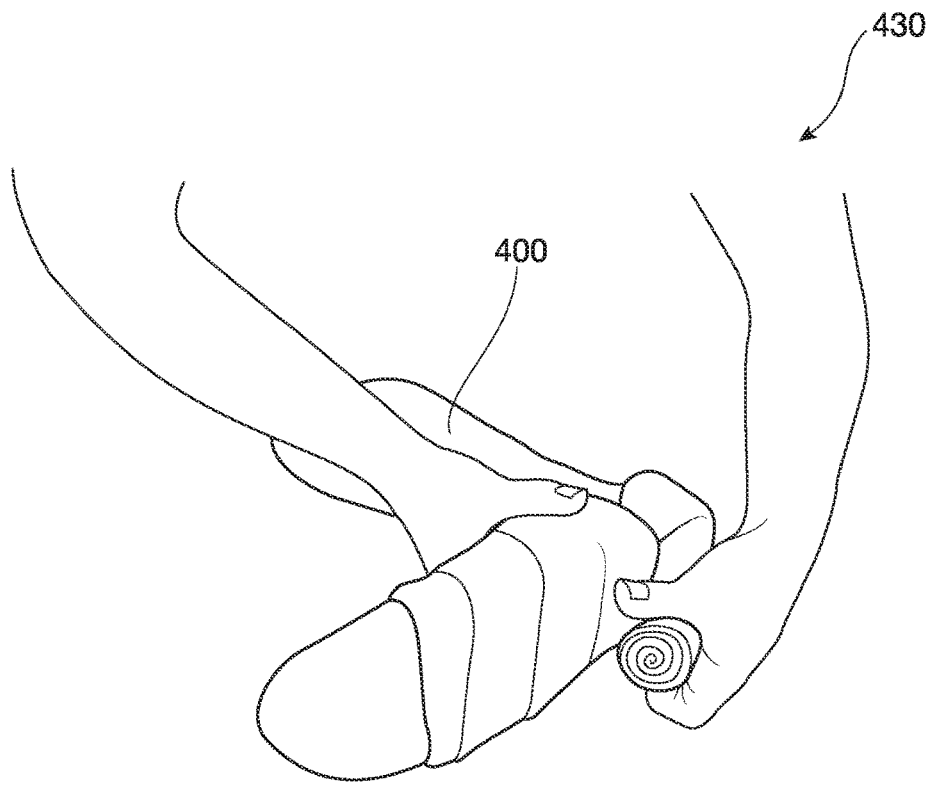
FIG. 4O is a perspective view of an exemplary step for fabricating the AFO of FIG. 1A to the anatomy of a patient, in accordance with the principles of the present disclosure.
Figure 4Q:
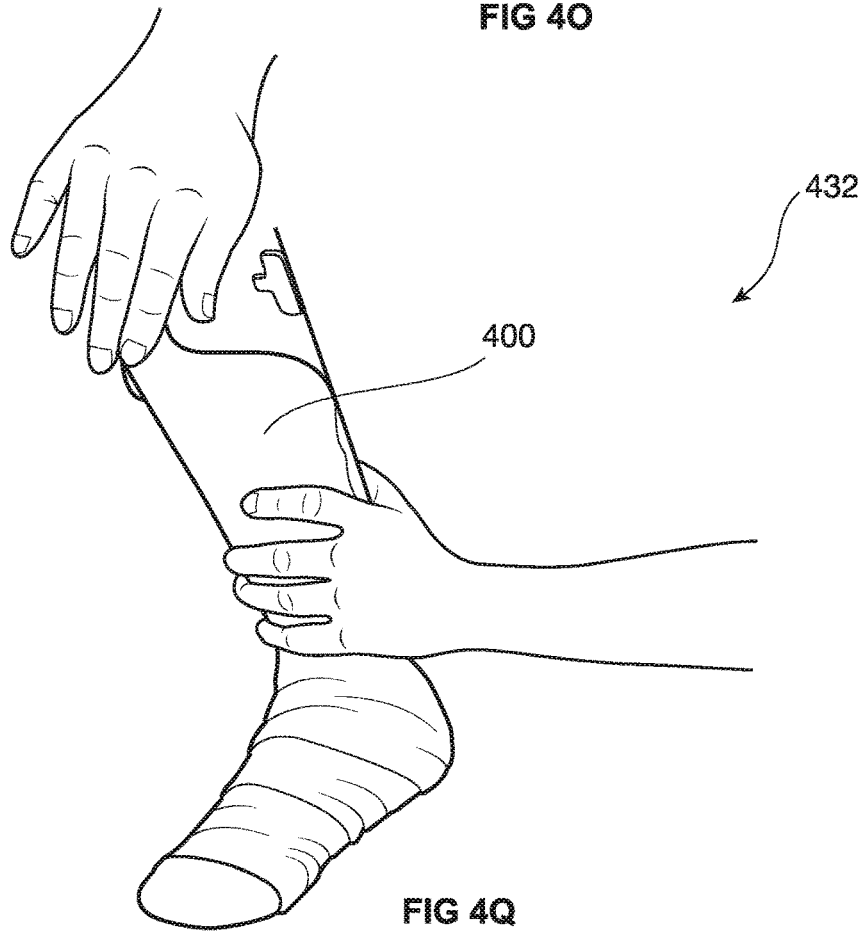
FIG. 4Q is a perspective view of an exemplary step for fabricating the AFO of FIG. 1A to the anatomy of a patient, in accordance with the principles of the present disclosure.
Figure 5A:
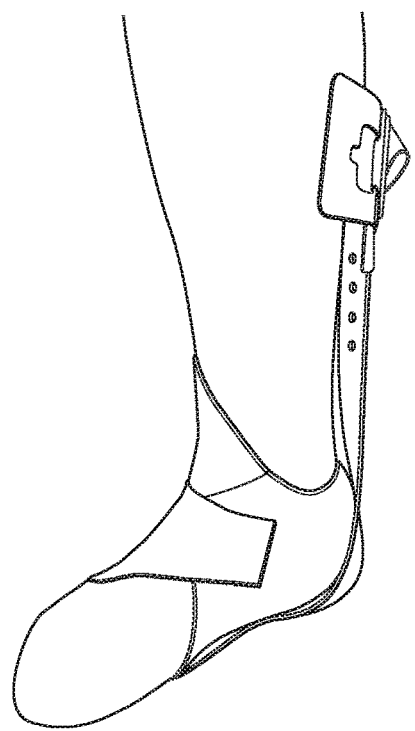
FIGS. 5A-5C illustrate various view for one exemplary inner boot soft good for use with the AFO of FIG. 1A, in accordance with the principles of the present disclosure.
Figure 5B:
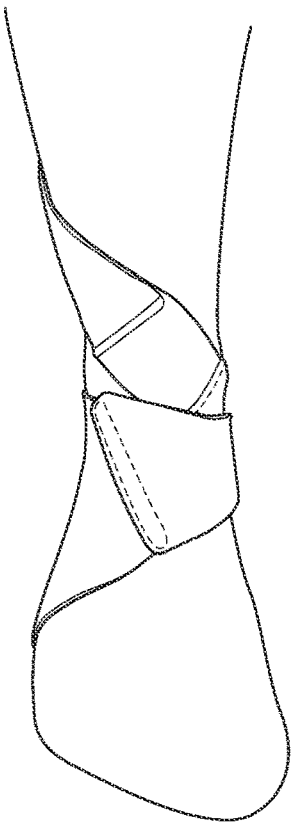
Figure 5C:
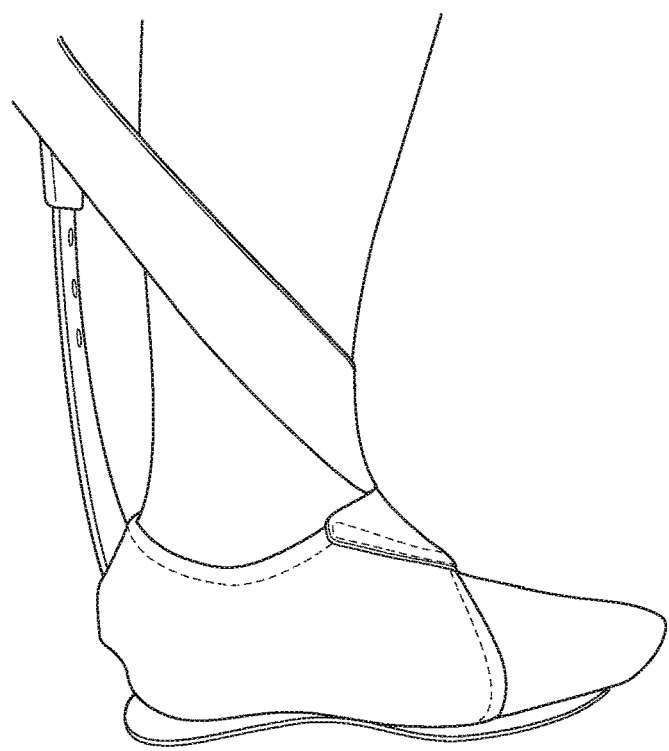
Figure 6A:
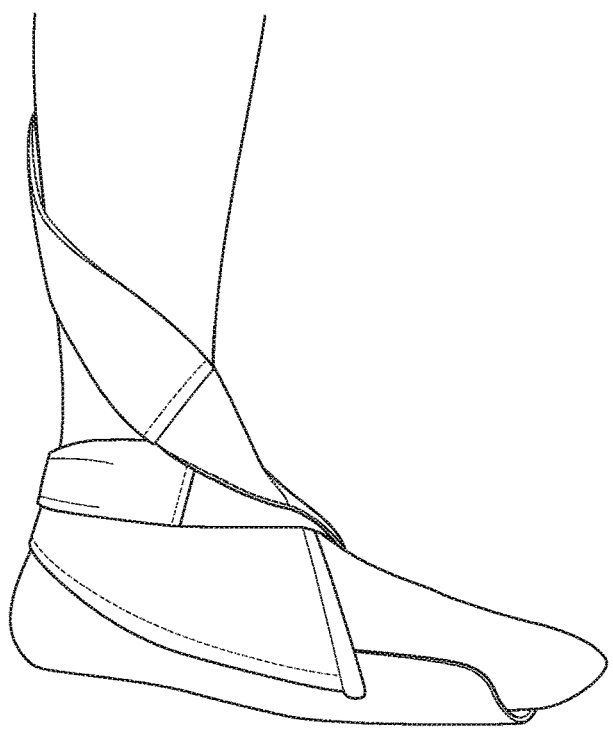
FIGS. 6A-6D illustrate various views for another exemplary inner boot soft good for use with the AFO of FIG. 1A, in accordance with the principles of the present disclosure.
Figure 6B:
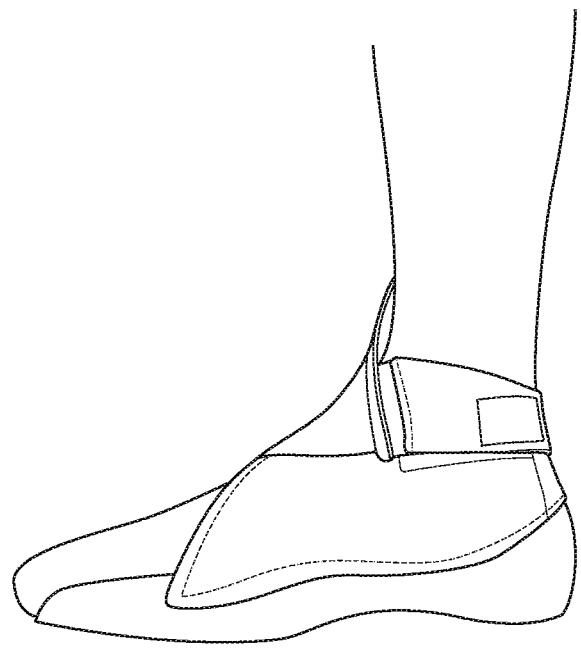
Figure 6C:
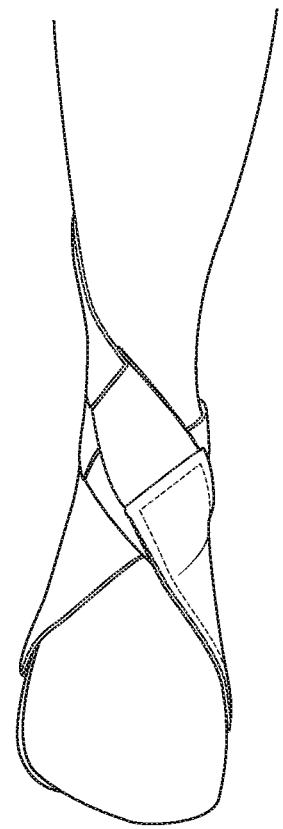
Figure 6D:
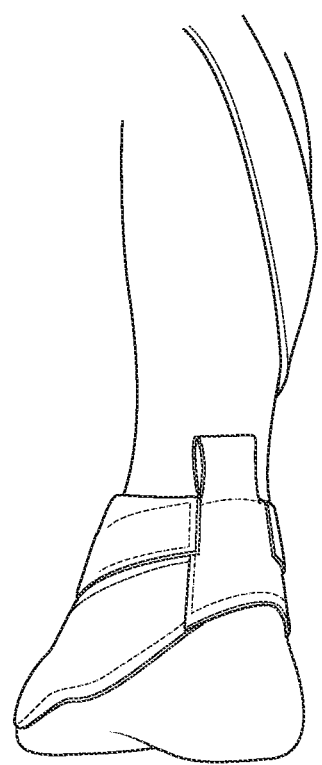
Figure 7A:
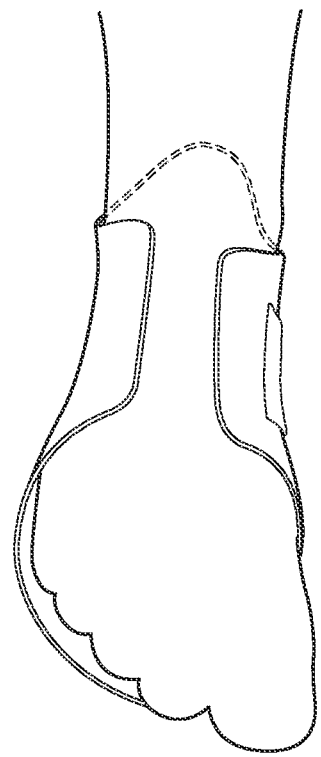
FIGS. 7A and 7B illustrate various views for yet another exemplary inner boot soft good for use with the AFO of FIG. 1A, in accordance with the principles of the present disclosure.
Figure 7B:
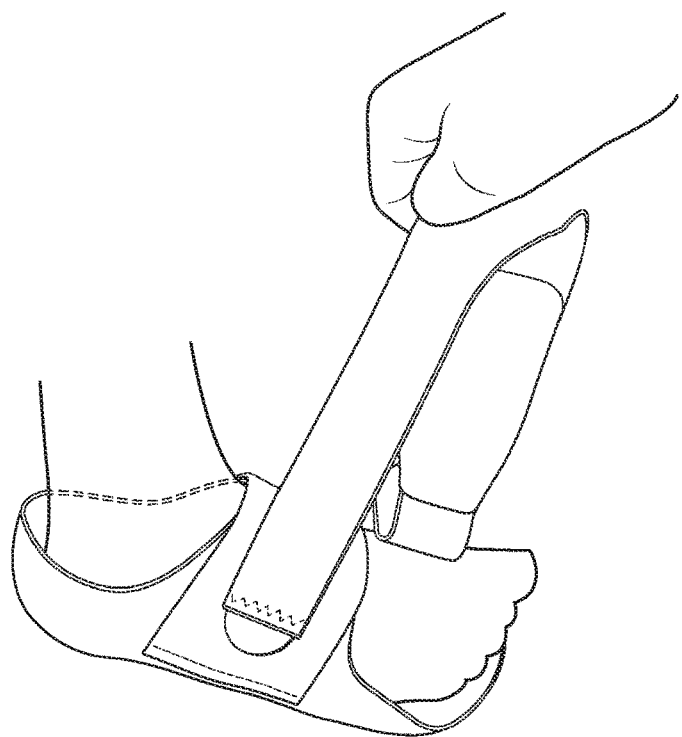
Figure 8A:
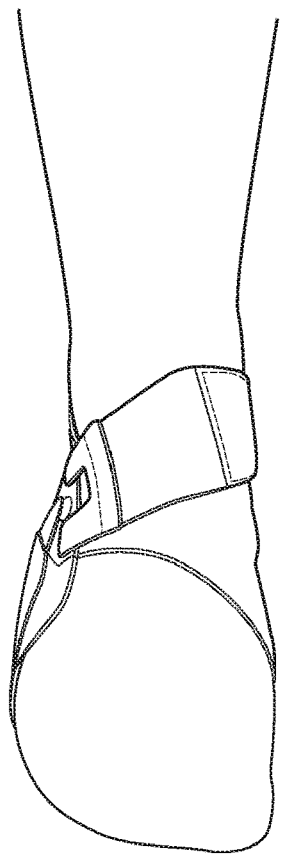
FIGS. 8A-8D illustrate various views for yet another exemplary inner boot soft good for use with the AFO of FIG. 1A, in accordance with the principles of the present disclosure.
Figure 8B:
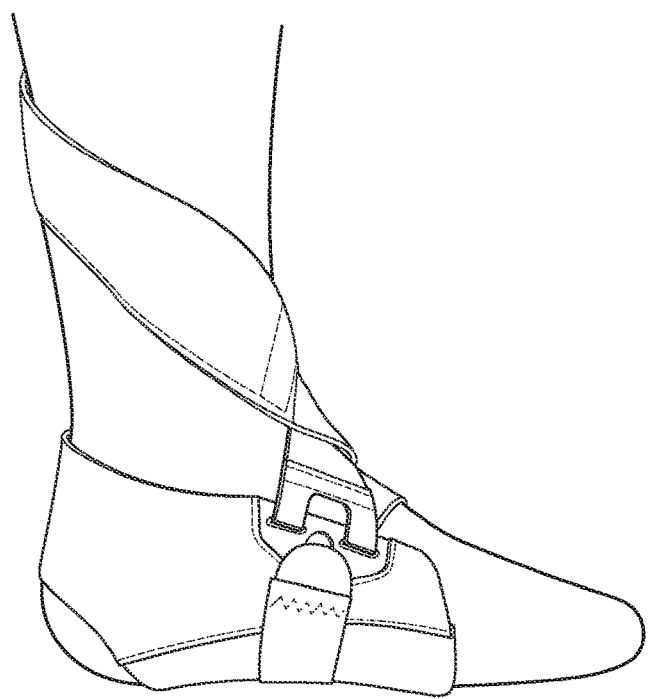
Figure 8C:
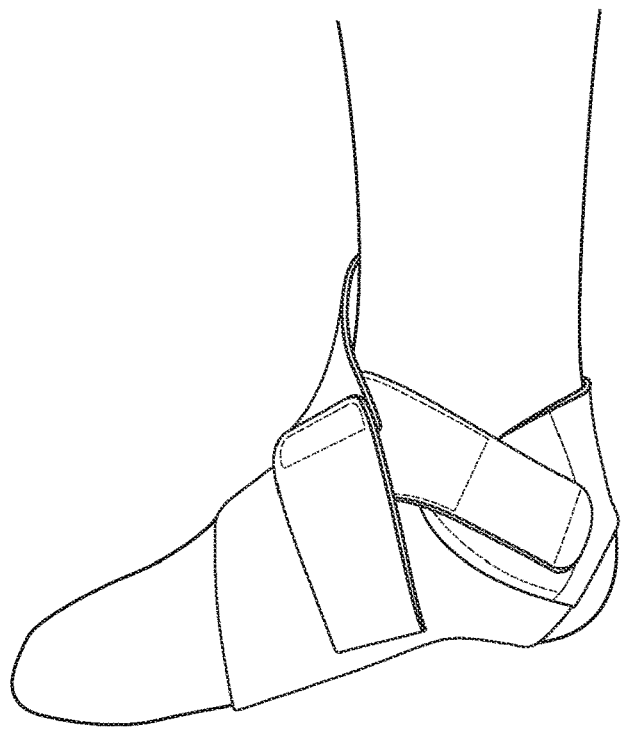
Figure 8D:
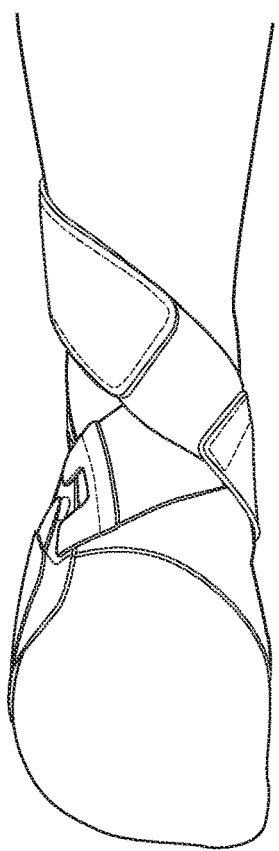
Figure 9A:
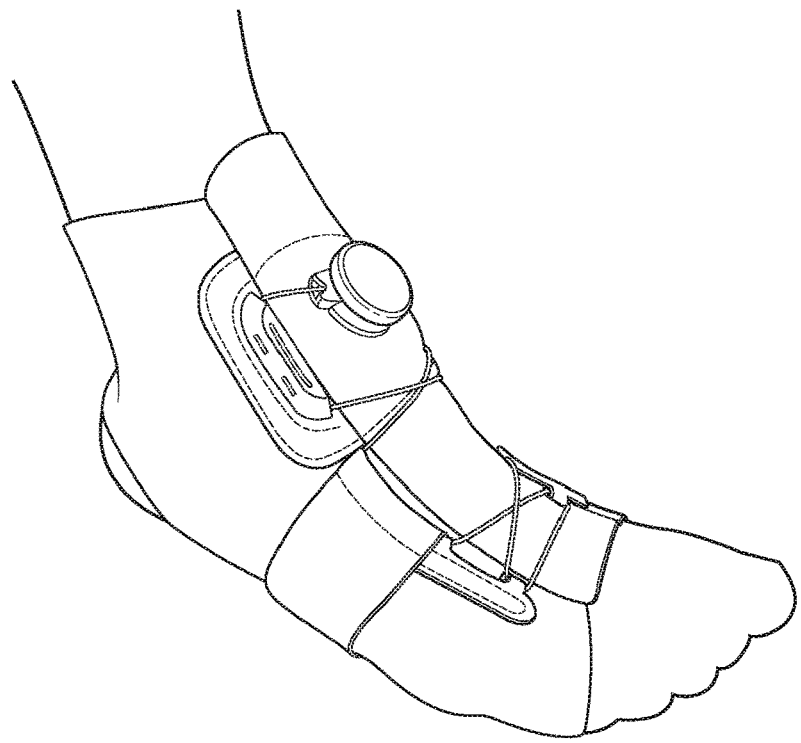
FIGS. 9A-9C illustrate various views for yet another exemplary inner boot soft good for use with the AFO of FIG. 1A, in accordance with the principles of the present disclosure.
Figure 9B:
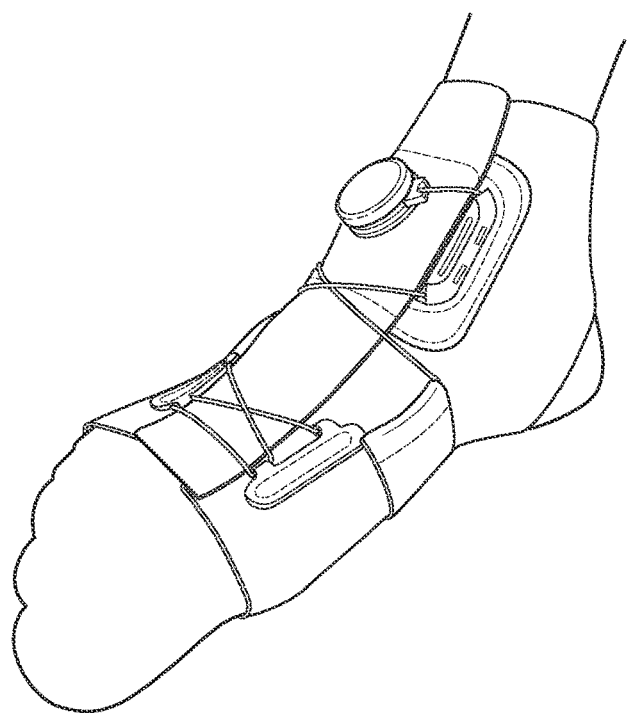
Figure 9C:
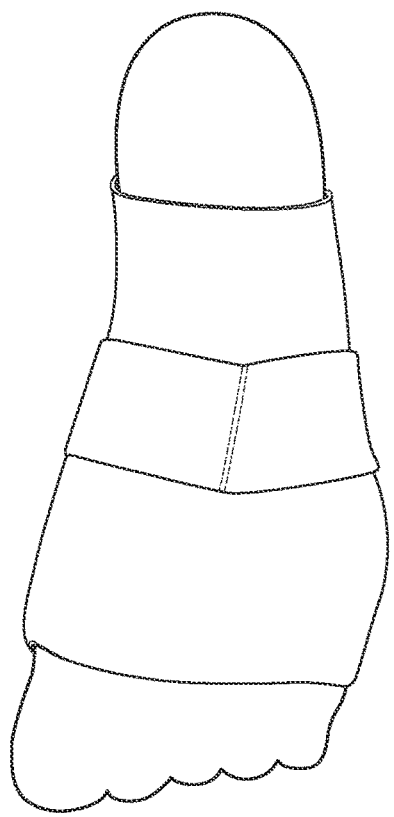
Figure 10:
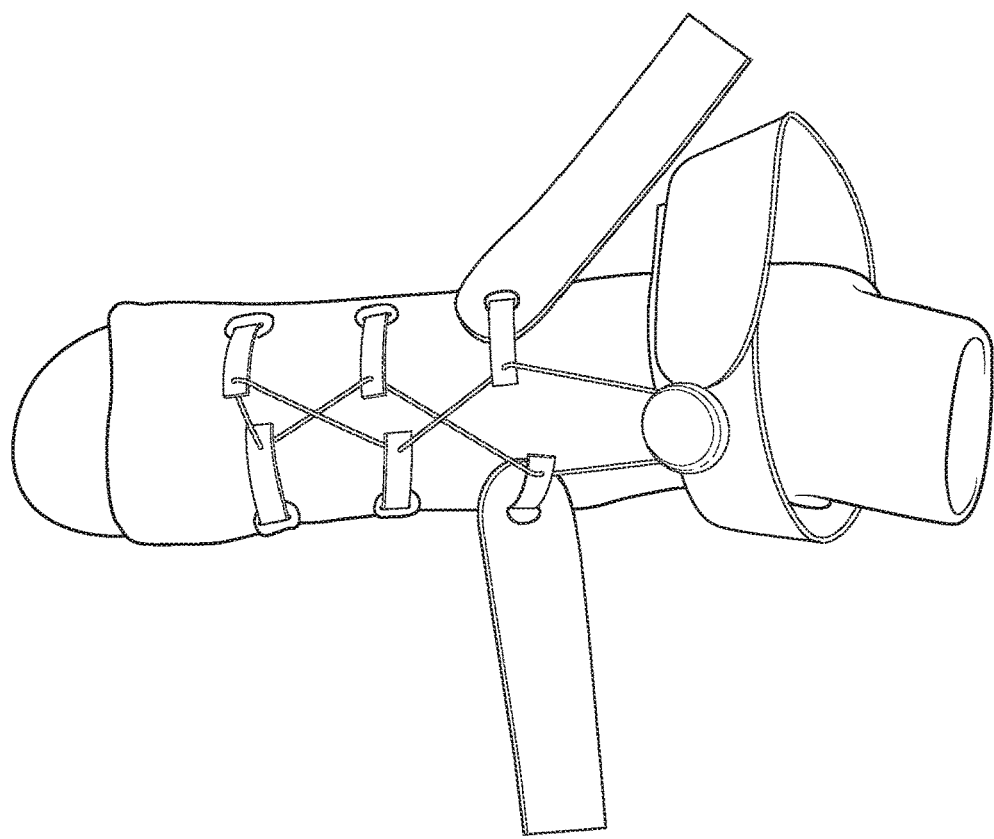
FIG. 10 is a top perspective view illustrating yet another exemplary inner boot soft good for use with the AFO of FIG. 1A, in accordance with the principles of the present disclosure.
Figure 11:
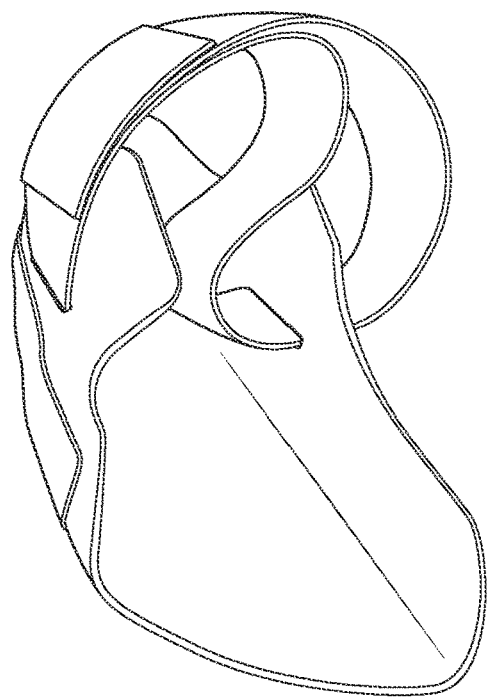
FIG. 11 is a perspective view of another exemplary inner boot for use with the AFO of FIG. 1A, in accordance with the principles of the present disclosure.
Figure 12A:
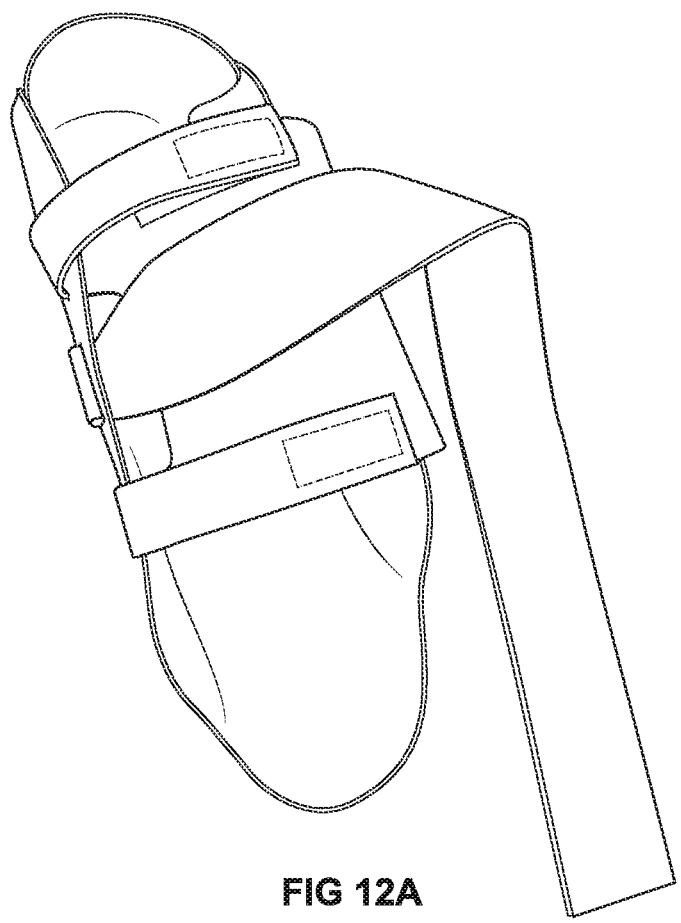
FIGS. 12A and 12B illustrate various views of yet another exemplary inner boot for use with the AFO of FIG. 1A, in accordance with the principles of the present disclosure.
Figure 12B:
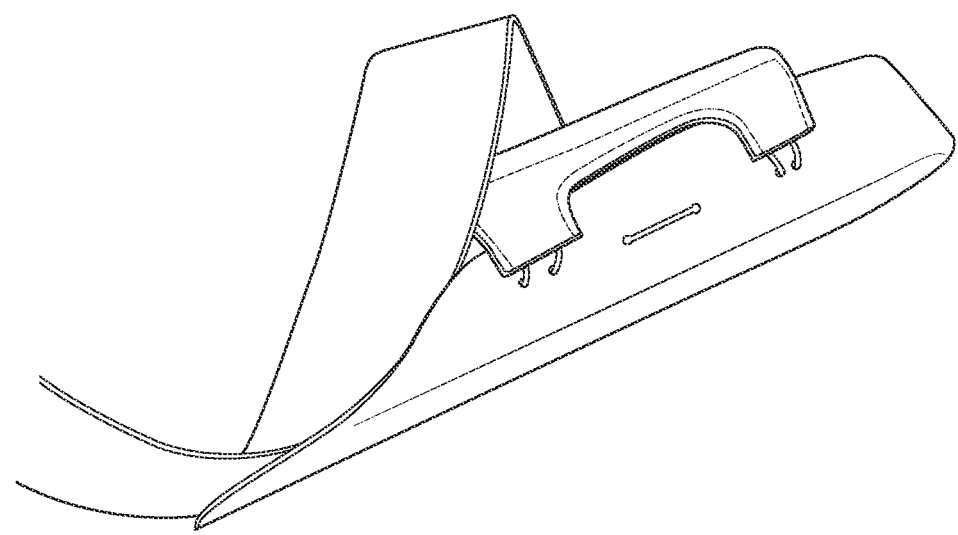
Figure 13A:
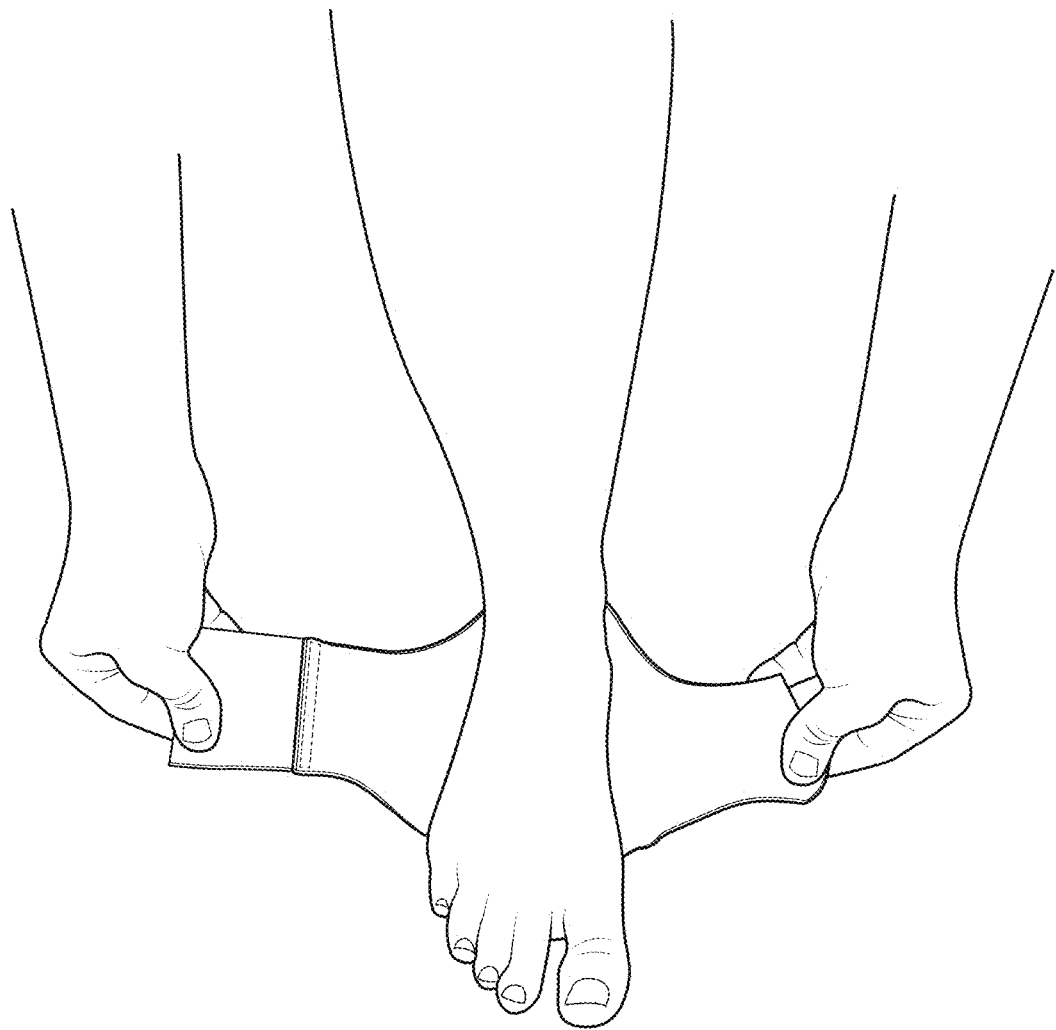
FIGS. 13A-13C illustrate various views of yet another exemplary inner boot soft good for use with the AFO of FIG. 1A, in accordance with the principles of the present disclosure.
Figure 13B:
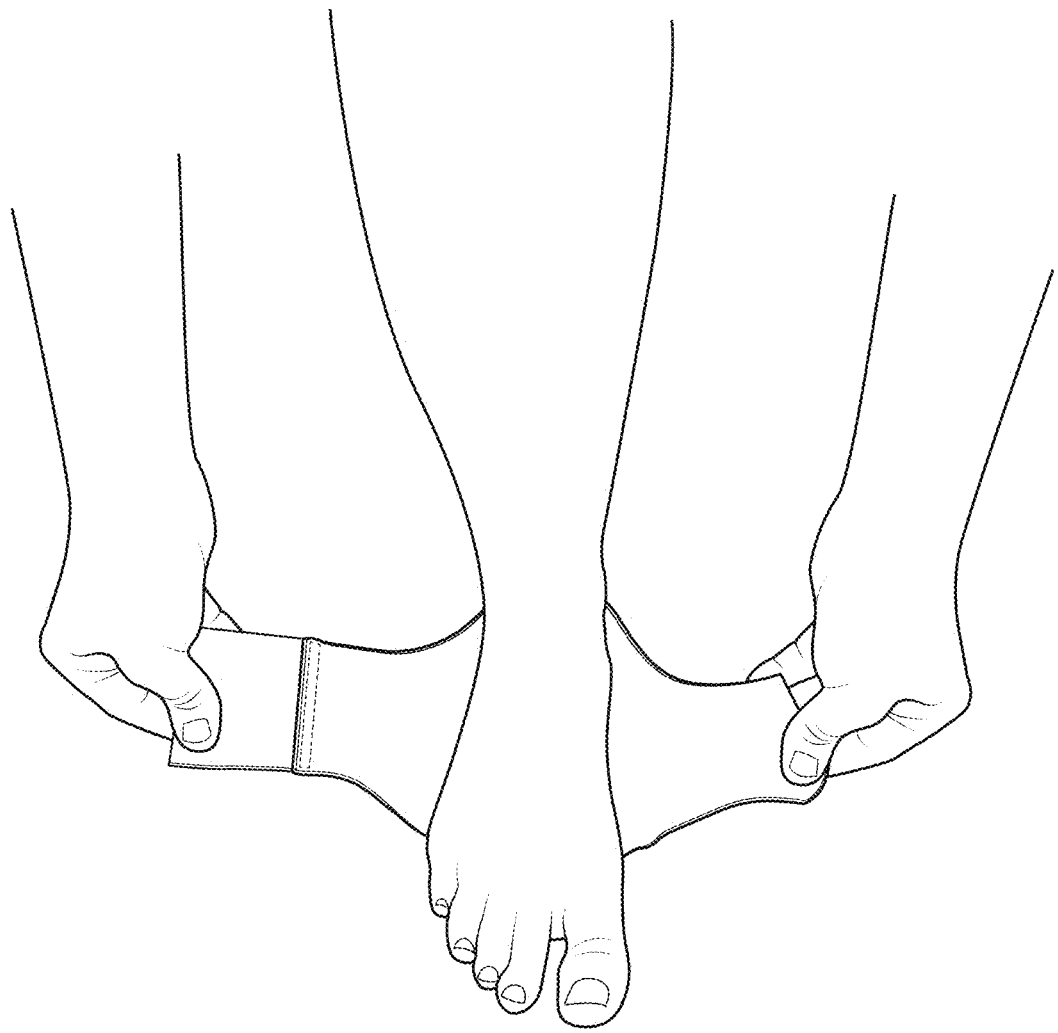
Figure 13C:

Referring now to FIGS. 4A-4Q, exemplary methodologies for customizing the AFO devices 100, 200 described herein are shown and described in detail. While primarily discussed in the context of the AFO 100 shown and described with respect to FIGS. 1A-1X-6, it would be readily apparent to one of ordinary skill given the contents of the present disclosure that certain ones of the following steps of the process may be utilized in combination with the ankle foot support structures also illustrated with respect to FIGS. 2A-3I. The following discussion is also primarily described with a certified orthopedic professional being able to perform the following steps in a clinical setting (as opposed to a manufacturing setting), although it would be readily apparent that alternative individuals or settings may be utilized in alternative variants. Moreover, while embodiments described herein our primarily described in the context of formable polymers that may be activated using, for example, heat and/or formable stays, it would be readily appreciated by one of ordinary skill given the contents of the present disclosure that the methodologies described herein are not so limited. For example, many of the parts described herein could be readily manufactured using three-dimensional (3D) printing technologies. As such, the anatomy for a given wearer of AFO 100, 200, 300 may be determined using 3D scanners where the measurements taken may in turn be used to 3D print, for example, the inner boot 142 and/or the formable layer 106 of the foot plate 104. These and other variants would be readily apparent to one of ordinary skill given the contents of the present disclosure.

One exemplary methodology for the customization of an AFO is shown in FIGS. 4A-4Q, a clinician may have the patient position their leg at an angle of approximately 90 degrees between the patient's thigh and the patient's lower leg. At step 402 shown in FIG. 4A, the clinician may mark the mid belly of the patient's calf which will mark the position of the top of the calf piece assembly 180 for optimal alignment of the AFO 100. The strut may then be trimmed in accordance with the determined correct calf height in some implementations (i.e., in variants in which a given strut is designed to accommodate larger disparities in anatomy between users of the AFO 100). The clinician may also mark bony prominences on the patient where pads may be placed on the patient to provide relief prior to casting the lower leg of the patient. At step 404 shown in FIG. 4B, the clinician may then take a cast of the patient's lower leg and ensure that sufficient casting material has been placed around the foot and calf area of the patient. As the cast hardens, the clinician may adjust and correct the patient's foot in the cast to ensure proper alignment. This adjustment and correction may be critical to ensure that the cast is taken correctly to ensure the AFO 100 functions as intended. As the cast sets, the clinician may place the casted leg onto the frame of the AFO 100 at step 406 shown in FIG. 4C. The strut 102 and foot plate 104 of the AFO 100 may act as a casting board and ensure the foot and leg are casted in the correct position, although in some variants a separate casting board may be utilized. In some implementations, a heel wedge may be placed under the strut during the casting process to accommodate the shoes of the patient or otherwise at the clinician's discretion for other anatomical reasons.

In some implementations, and as shown at step 424 in FIG. 4L, a certified orthopedic professional may have the patient put their foot and insole on tracing paper, where their foot is traced. Various metatarsal and calcaneus locations will also be marked and labeled on the tracing paper. As shown at step 426 in FIG. 4M, the tracing performed above may be cut from the sheet of tracing paper. The cut tracing will be applied to the surface of the foot plate 104 and the foot plate 104 will next be trimmed. The trimming of the foot plate may be accomplished using standard scissors or other cutting tools.

In some implementations, after the cast material sets, the cast may be removed from the patient's leg. For example, the cast may be divided into two (or more) pieces. After removal, the cast is placed back together and the cast is reinforced using, for example, staples, tape and/or other fastening means in order to hold the removed cast together. This cast may then be subsequently used as a patient model and various ones of the AFO components may be molded around this taken cast.

With the cast removed from the patient's leg, the inner boot 142 may be placed around the foot of the cast at step 428 as shown in FIG. 4N. The inner boot 142 walls may be marked to indicate where the inner boot 142 may be trimmed to fit the patient's anatomy and treatment needs. The inner boot side 142 walls are then trimmed in accordance with the markings that have been placed onto the inner boot 142 walls. At step 408 shown in FIG. 4D, heat is then applied to the inner boot using, for example, a heat gun and pressure is then applied to the heated inner boot 142 using, for example, the hands of the clinician to mold the inner boot 142 to the patient's cast. The inner boot 142 may also be heated in an oven, hot water, or other suitable heating methods. The foot plate portion of the inner boot may also be trimmed to match the patient's shoe insole and/or based on the patient's treatment needs. The trimmed portions of the inner boot 142 are then smoothed using, for example, a sanding block, rotary tool, or other suitable tools available to the clinician.

At step 410 shown in FIG. 4E, the molded inner boot 142 and cast are then placed onto the AFO footplate 104. The clinician may then mark the first and fifth metatarsal heads, the outline of the patient's foot and any other areas that will be formed around the patient's anatomy for treatment. The clinician may also draw the size and shape for the metatarsal supports at the front of the footplate. The size and shape of the calcaneus portion of the cast may also be drawn onto the back of the footplate. The footplate may then be trimmed in accordance with these markings and the trimmed footplate is then heated with, for example, a heat gun to mold the footplate around the inner boot 142 that has been placed onto the cast. The trimmed edges of the footplate may then be smoothed using, for example, a sanding block, rotary tool, or other suitable tools available to the clinician.

At step 412 shown in FIG. 4F, the calf cuff may then be fabricated to match the anatomy of the patient. For example, based on the patient's calf circumference measurement, the calf cuff (in its flattened state) may be trimmed and smoothed using, for example, a sanding block, rotary tool, or other suitable tools available to the clinician. The calf cuff may then be slid onto the strut and slid to the appropriate marking that was marked that corresponds to the mid belly of the patient's calf that was previously placed onto the cast. The calf cuff is then secured to the strut using, for example, the aforementioned fastening mechanism with the calf cuff placed at the appropriate height. The calf cuff is then heated using, for example, a heat gun and the calf cuff is then molded around the cast. The calf strap is then attached to the calf cuff and subsequently tightened around the cast to hold the calf cuff in place. The excess calf strap is then trimmed to remove excess material so that the calf strap properly conforms to the patient's cast. The calf strap is then loosened and then re-fastened to ensure appropriate adjustments have been made. The AFO is subsequently removed from the cast. At step 414 shown in FIG. 4G, subsequent to AFO removal from the cast, the liner(s) are attached to the inside of the calf cuff ensuring that all edges of the calf cuff are sufficiently padded for patient comfort. The liner(s) may be repositioned by moving the attachment points between the calf cuff and liner(s) as needed to ensure proper alignment. At steps 430 and 432 shown in FIGS. 4O and 4Q, a clinician may also use elastic bands or wrapping to hold components to the cast during the forming process. They may heat and form the inner boot, the foot plate and the calf cuff first and then remove the cast and trim and smooth all edges.

At step 416 shown in FIG. 4H, the inner boot 142 may then be attached to the foot plate 104 of the AFO 100. Webbing may be fed through the inner boot slots towards the posterior portion of the inner boot. The webbing may then be routed around the posterior end of the foot plate 104 and secured to the underside of the footplate using, for example, hook and loop fasteners, a pressure sensitive adhesive (PSA), or other suitable attachment means. If necessary, the strap that secures the inner boot to the footplate may be trimmed as necessary to accommodate the size of the patient's foot or to accommodate the addition of a heel wedge to the assembly. With the inner boot attached to the AFO, the AFO may then be placed onto the cast and the inner boot is aligned to the footplate based on the patient's anatomy and treatment needs using the aforementioned fastening mechanisms.

At step 418 shown in FIG. 4I, the dorsum strap may then be attached to the inner boot by placing the dorsum strap through the slot located on the inner boot so that, for example, the stopper (e.g., TPU edge) of the dorsum strap is located on the inside surface of the inner boot. The dorsum strap may then be tightened around the patient's cast and excess strap material on the dorsum strap may then be trimmed. A tab cover may be placed over the trimmed edge of the dorsum strap to assist the patient with donning and doffing of the AFO 100. For example, the tab cover may be attached to the dorsum strap using hook and loop fasteners, adhesives, sewing, or other suitable attachment mechanisms.

At step 420 shown in FIG. 4J, the spiral strap 164 and/or calcaneus strap 165 may then be fed through the slots 146/147 on the inner boot 142 and then tightened. Excess material on the spiral strap 164 and/or calcaneus strap may then be trimmed, and a tab cover may be applied to cover the trimmed edges. The tab covers may also assist the patient with donning and doffing of the AFO 100. The AFO 100 has now been customized to the anatomy of the patient and is now ready for use at step 422 as shown in FIG. 4K.

Exemplary Soft Goods for use with the Exemplary Ankle Foot Support Structures—

Referring now to FIGS. 5A-13C, various soft goods that can be utilized in combination with the aforementioned ankle foot support structures are shown. These soft goods may be added to provide for additional support for the ankle and foot, and/or may be added to provide for additional comfort for the wearer of the ankle support structure. Various ones of the soft goods shown in FIGS. 5A-13C may incorporate polymers such as, for example, thermoplastic to provide additional rigidity and support to the soft goods shown in FIGS. 5A-13C.

Where certain elements of these implementations can be partially or fully implemented using known components, only those portions of such known components that are necessary for an understanding of the present disclosure are described, and detailed descriptions of other portions of such known components are omitted so as not to obscure the disclosure.

In the present specification, an implementation showing a singular component should not be considered limiting; rather, the disclosure is intended to encompass other implementations including a plurality of the same component, and vice versa, unless explicitly stated otherwise herein.

Further, the present disclosure encompasses present and future known equivalents to the components referred to herein by way of illustration.

It will be recognized that while certain aspects of the technology are described in terms of a specific sequence of steps of a method, these descriptions are only illustrative of the broader methods of the disclosure and may be modified as required by the particular application. Certain steps may be rendered unnecessary or optional under certain circumstances. Additionally, certain steps or functionality may be added to the disclosed implementations, or the order of performance of two or more steps permuted. All such variations are considered to be encompassed within the disclosure disclosed and claimed herein.

While the above detailed description has shown, described, and pointed out novel features of the disclosure as applied to various implementations, it will be understood that various omissions, substitutions, and changes in the form and details of the device or process illustrated may be made by those skilled in the art without departing from the disclosure. The foregoing description is of the best mode presently contemplated of carrying out the principles of the disclosure. This description is in no way meant to be limiting, but rather should be taken as illustrative of the general principles of the technology. The scope of the disclosure should be determined with reference to the claims.

What is claimed:

1. An ankle foot orthosis (AFO), comprising:
   a carbon fiber strut that includes a carbon fiber foot plate;
   a formable layer that is coupled with the carbon fiber foot plate, the formable layer being formable from an initial shape to a formed shape;
   an inner boot, where the formable layer being formed into the formed shape is configured to be formed around geometry of portions of the inner boot;

a moldable calf piece that is configured to be attached to the carbon fiber strut;

a spiral strap that is coupled between the moldable calf piece and the inner boot;

a calcaneus strap that is coupled between the spiral strap and the inner boot;

wherein the inner boot comprises a mid-foot/fore foot strap slot and a calcaneus strap slot, the calcaneus strap slot being positioned posterior from the mid-foot/fore foot strap slot on the inner boot;

wherein the spiral strap enters the inner boot on a first side of the inner boot, travels along an interior surface of the inner boot, and is coupled with the mid-foot/fore foot strap slot on a second side of the inner boot, the second side of the inner boot being on an opposing side of the inner boot from the first side of the inner boot; and wherein the calcaneus strap enters the inner boot on the first side of the inner boot, travels along the interior surface of the inner boot, and is coupled with the calcaneus strap slot on the second side of the inner boot.

2. The AFO of claim 1, further comprising a dorsum strap comprised of webbing material, the dorsum strap being received within two dorsum strap slots disposed on the inner boot.

3. The AFO of claim 2, wherein the two dorsum strap slots are disposed at an angle greater than zero degrees (0°) and less than ninety degrees (90°) with respect to a bottom plane of the inner boot.

4. The AFO of claim 3, wherein the dorsum strap has a stopper disposed at one end of the dorsum strap, the stopper configured to be received on the interior surface of the inner boot adjacent one of the two dorsum strap slots.

5. The AFO of claim 4, wherein the stopper is oriented orthogonal to the webbing material of the dorsum strap, the webbing material comprising two layers of webbing material, one layer of the two layers being oriented in a first direction of the stopper, a second layer of the two layers being oriented in a second direction of the stopper, the second direction being opposite from the first direction.

6. The AFO of claim 3, wherein the spiral strap is comprised of webbing material.

7. The AFO of claim 1, wherein the spiral strap is comprised of webbing material.

8. The AFO of claim 7, wherein the spiral strap comprises a stopper at an end portion of the spiral strap, the stopper being received on an external surface of the inner boot, the spiral strap being fed through the mid-foot/fore foot strap slot disposed in the inner boot.

9. The AFO of claim 8, wherein the inner boot further comprises a recess positioned around the mid-foot/fore foot strap slot disposed in the inner boot, the recess configured to receive the stopper of the spiral strap.

10. The AFO of claim 8, wherein the stopper is oriented orthogonal to the webbing material of the spiral strap, the webbing material comprising two layers of webbing material, one layer of the two layers being oriented in a first direction of the stopper, a second layer of the two layers being oriented in a second direction of the stopper, the second direction being opposite from the first direction.

11. The AFO of claim 1, wherein the inner boot comprises a posterior slot, the posterior slot being disposed at a posterior portion of the inner boot; and a back strap that has a first end attached to the interior surface of the inner boot, the back strap being routed through the posterior slot, the back strap being routed around a posterior edge of the carbon fiber foot plate, and a second end of the back strap being coupled with an underside of the carbon fiber foot plate.

12. The AFO of claim 11, wherein the second end of the back strap is received within a recess that is disposed on the underside of the carbon fiber foot plate.

\* \* \* \* \*